United States Patent
McDonald et al.

(10) Patent No.: US 10,421,973 B2
(45) Date of Patent: Sep. 24, 2019

(54) CHEMICALLY INDUCIBLE CUCUMBER MOSAIC VIRUS PROTEIN EXPRESSION SYSTEM

(71) Applicant: **TH

(56) References Cited

OTHER PUBLICATIONS

Griffiths et al., "The Reactivity and Oxidation Pathway of Cysteine 232 in Recombinant Human alpha 1-Antitrypsin", The Journal of Biological Chemistry, vol. 277, No. 28, 2002, pp. 25486-25492.
Hamilton et al., "A binary-BAC System for Plant Transformation with High-Molecular-weight DNA", Gene, vol. 200, 1997, pp. 107-116.
Huang et al., "Expression and Purification of Functional Human Alpha-1-Antitrypsin from Cultured Plant Cells", Biotechnology Progress, vol. 15, 2001, pp. 126-133.
Huntington et al., "Structure of a Serpin-Protease Complex Shows Inhibition by Deformation", Letters to Nature, vol. 407, Oct. 19, 2000, pp. 923-992.
International Search Report and Written Opinion received for PCT Patent Application No. PCT/US2007/020712, dated Sep. 23, 2008, 3 pages.
Joo et al., "Enhanced Production of hGM-CSF by Medium Exchange in Transgenic Oryza Sativa L. Suspension Cultures", Enzyme and Microbial Technology, vol. 39, 2006, pp. 486-489.
Kolarich et al., "Comprehensive Glycol-Proteomic Analysis of Human alpha 1-antitrypsin and its charge isoforms", Proteomics, vol. 6, 2006, pp. 3369-3380.
Kwon et al., "Differential Roles of the 5% Untranslated Regions of Cucumber Mosaic Virus RNAs 1, 2, 3 and 4 in Translational Competition", Virus Research, vol. 66, 2000, 175-185.
Lei et al., "Recombination with Coat Protein Transgene in a Complementation System Based on Cucumber Mosaic Virus (CMV)", Science in China, vol. 44, No. 3, Jun. 2001, pp. 263-273.
Ma et al., "The Production of Recombinant Pharmaceutical Proteins in Plants", Nature Reviews: Genetics, vol. 4, Oct. 2003, pp. 794-805.
Manske et al., "Development and Assessment of a Potato virus X-based expression system with improved biosafety", Environmental Biosafety Research, vol. 4, 2005, pp. 45-57.
McBride et al., "Improved Binary Vectors for Agrobacterium-Mediated Plant Transformation," Plant Molecular Biology, vol. 14, 1990, pp. 269-276.
Moore et al., "Transactivated and chemically inducible gene expression in plants", The Plant Journal, vol. 45, 2006, pp. 651-683.
Mori et al., "Inducible High-Level mRNA Amplification System by Viral Replicase in transgenic Plants", The Plant Journal, vol. 27, No. 1, 2001, pp. 79-86.
Mori et al., "mRNA Amplification System BY Viral Replicase in Transgenic Plants", FEBS, vol. 336, No. 1, Dec. 1993, pp. 171-174.
Non Final Office Action received for U.S. Appl. No. 12/442,395, dated Nov. 18, 2014, 10 pages.
Non Final Office Action received for U.S. Appl. No. 12/442,395, dated Jun. 10, 2013, 9 pages.
Non Final Office Action received for U.S. Appl. No. 12/442,395, dated Nov. 21, 2012, 13 pages.
Non-Final Office Action received for U.S. Appl. No. 12/442,395, dated Apr. 15, 2016, 7 pages.
Notice of Allowance received for U.S. Appl. No. 12/442,395, dated Nov. 15, 2016, 5 pages.
Nykiforuk, "Transgenic Expression and Recovery of Biologically Active Recombinant Human Insulin From Arabidopsis Thaliana Seeds", Plant Biotechnology Journal, vol. 4, 2006, pp. 77-85.
Quadt et al., "Formation of Brome Mosaic Virus RNA-Dependent RNA Polymerase in Yeast Requires Coexpression of Viral Proteins and Viral RNA", Proc. Natl. Acad. Sci. USA Biochemistry, vol. 92, May 1995, pp. 4892-4896.
Rabindran et al., "Assessment of Recombinants that Arise from the Use of a TMV-Based Transient Expression Vector", Virology, vol. 284, 2001, pp. 182-189.
Ray et al., "A Second Functional RNA Domain in the 5 UTR of the Tomato Bushy Stunt Virus Genome: Intra- and Interdomain Interactions Mediate Viral RNA Replication", RNA, vol. 9, No. 10, 2003, pp. 1223-1245.
Restriction Requirement received for U.S. Appl. No. 12/442,395, dated Jun. 15, 2012.
Rezaian et al., "Nucleotide sequence of cucumber-mosaic-virus RNA 2 reveals a translation product significantly homologous to corresponding proteins of other viruses", European Journal of Biochemistry, vol. 143, 1984, pp. 277-284.
Savka et al., "Tobacco Etch Virus Leader Sequence Enhances Inducible Indoleacetic Acid-Lysine Synthetase Activity in Transgenic Plants", Plant Physiology Biochemistry, vol. 39, 2001, pp. 631-641.
Schiermeyer et al., "Production of Desmodus Rotundus Salivary Plasminogen Activator 01 (DSPA 01) in Tobacco is Hampered by Proteolysis", Biotechnology and Bioengineering, vol. 89, No. 7, Mar. 30, 2005, pp. 848-858.
Shivprasad et al., "Heterologous Sequences Greatly Affect Foreign Gene Expression in Tobacco Mosaic Virus-Based Vectors", Virology, vol. 255, 1999, pp. 312-323.
Sun et al., "The *Arabidopsis* AtIPT8/PGA22 Gene Encodes an Isopentenyl Transferase that is Involved in de Novo Cytokinin Biosynthesis", Plant Physiology, vol. 131, Jan. 2003, pp. 167-176.
Tavva et al., "Development of a Methoxyfenozide-Responsive Gene Switch for Applications in Plants", The Plant Journal, vol. 45, 2006, pp. 457-469.
Terashima et al., "Production of Functional Human c I-Antitrypsin by Plant Cell Culture", Applied Microbiology Biotechnology, vol. 52, 1999, pp. 516-523.
Trexler et al., "A Cyclical Semi continuous Process for Production of Human c t-Antitrypsin Using Metabolically Induced Plant Cell Suspension Cultures", Biotechnology Progress, vol. 2, 2005, pp. 321-328.
Trexler et al., "Bioreactor Production of Human c t-Antitrypsin Using Metabolically Regulated Plant Cell Cultures", Biotechnology Progress, vol. 18, 2002, pp. 501-508.
Turpen et al., "Transfection of Whole Plants from Wounds Inoculated with Agrobacterium Tumefactions Containing cDNA of Tobacco Mosaic Virus", Journal of Biological Methods, vol. 42, 1993, pp. 227-240.
Voinnet et al., "An Enhanced Transient Expression System in Plants Based on Suppression of Gene Silencing by the p19 Protein of Tomato Bushy Stunt Virus", The Plant Journal, vol. 33, 2003, pp. 949-956.
Wilczynska et al., "Structural Insights into Serpin-Protease Complexes Reveal the Inhibitory Mechanism of Serpins", Nature Structural Biology, vol. 4, No. 5, May 1997, pp. 354-357.
Wilson et al., "Position Effects on Eukaryotic Gene Expression", Annual Review of Cell Biology, vol. 6, 1990, pp. 679-714.
Zuo et al., "The Wuschel Gene Promotes Vegetative-to-Embryonic Transition in *Arabidopsis*", The Plant Journal, vol. 30, No. 3, May 2002, pp. 349-359.

* cited by examiner

CHEMICALLY INDUCIBLE CUCUMBER MOSAIC VIRUS PROTEIN EXPRESSION SYSTEM

CROSS-REFERENCES TO RELATED APPLICATIONS

This application is a divisional of U.S. patent application Ser. No. 12/442,395, filed on Nov. 10, 2009, which is a U.S. National Phase patent application of PCT/US2007/020712, filed Sep. 24, 2007, which claims the benefit of U.S. Provisional Application No. 60/846,704, filed on Sep. 22, 2006, each of which are hereby incorporated herein by reference in their entireties.

GOVERNMENT INTEREST

This invention was made with Government support under Grant (or Contract) No. BES-0214527 awarded by the National Science Foundation and NSF REU. The US Government has certain rights in the invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 514112002910SEQLISTING.txt, date recorded: Feb. 9, 2017, size: 3 KB).

FIELD OF THE INVENTION

This invention is in the field of plant breeding and plant molecular biology. In particular, this invention relates to a novel chemically inducible plant expression system that allows controllable, high level expression of foreign genes in plant hosts.

BACKGROUND OF THE INVENTION

Plants offer enormous potential for production of recombinant forms of therapeutics and diagnostics for humans and animal applications, for example, human blood proteins, antibodies, vaccines, and the like. Plants have the ability to perform complex post-translational modifications and are intrinsically safe since they do not propagate mammalian viruses or pathogens. Plants also offer a lower cost alternative and are easier to scale-up compared to traditional mammalian cell culture production methods (Goldstein and Thomas, 2004; Ma et al., 2003). Thus, the potential for plant expression systems to serve as large scale production methods of therapeutic and diagnostic proteins, including the production of enzymes is compelling. Transient production approaches utilizing agroinfiltration or plant viral infection of plant tissue are particularly promising for short production timelines due to the relatively short time needed to go from gene to product, and the ability to use available agricultural biomass for rapid, large scale production (Fischer et al., 1999). Despite the ease and short turnaround time for transient production, use of recombinant plant viruses has been hindered by various shortcomings, including low infection efficiency, the risks associated with the release of the competent recombinant virus vectors into the environment (Manske and Schiemann, 2005), limitations on the size of the transgene, and transgene instability (Rabindran and Dawson, 2001; Shivprasad et al., 1999).

*Agrobacterium*-mediated infection to deliver viral amplicons was first reported in 1993 (Turpen et al., 1993). Gleba et al. (2005) described a plant virus based expression technology, termed "magnifection", wherein whole plants are vacuum infiltrated with *A. tumefaciens* containing a binary vector capable of expressing recombinant viral RNA replicons able to move from cell-to-cell, multiply, and express amplified levels of transgenes carried by the viral replicon. Gils et al. have shown high level production of correctly processed, biologically active human growth hormone using transient agroinfiltration of *N. benthamiana* leaves with multiple constructs that allow the in planta assembly of TMV viral replicons (Gils et al., 2005). Production of heterologous proteins utilizing constitutively-expressed viral amplicons has also been investigated in stably transformed plants, however, low recombinant viral levels, and low product titers resulting from post-transcriptional gene silencing (PTGS) have been continuously problematic (Angell and Baulcombe, 1997; Mori et al., 1993). In order to address this issue, Mori et al. (2001) constructed a chemically inducible Brome mosaic virus (BMV)-based amplicon utilizing the dexamethasone (DEX) glucocorticoid-inducible transcription system (Aoyama and Chua, 1997) for production of human gamma interferon in transgenic *Nicotiana benthamiana*. A similar approach was used for protein expression using a plant DNA virus amplicon (Zhang and Mason, 2006).

However, low recombinant viral levels, and low product titers resulting from post-transcriptional gene silencing continue to be a problem. Thus, with increasing threats of global pandemics and bioterrorism, there is a critical need for new bio-manufacturing technologies that allow rapid, large scale and cost-effective production of diagnostic, therapeutic and prophylactic compounds that can be used for detection, treatment or vaccination following such an event. The invention addresses this need.

There is also an increasing need for renewable and more environmentally friendly alternatives and supplements to fossil fuels and the efficient, low cost and scalable production of enzymes that are involved in the biosynthesis of such fuels. While bioethanol and biodiesel are rapidly expanding as renewable, more environmentally friendly alternatives to fossil fuel derived gasoline and diesel, new technologies that allow, for example, energy efficient and cost efficient degradation of lignocellosic biomass would represent a major breakthrough. Although there have been advances in improving the activity of enzymes involved in the degradation of lignocellulosic biomass, design of engineered cellulase mixtures, development of more productive host strains, and utilization of inexpensive medium components, the high cost of producing, recovering and formulating cellulase enzymes using traditional fungal or bacterial fermentation continues to impact the economics of ethanol production from lignocellulosic biomass. Microbial fermentations require large energy inputs due to agitation, aeration, temperature control and in some cases cell disruption and enzyme recovery, as well as high capital equipment costs for fermentors and downstream processing unit operations. The application of cellulases often requires pretreatment of lignocellulosic biomass to facilitate accessibility of the enzymes to the complex substrate, again requiring additional energy inputs and/or costly treatment of acid/base wastes. Thus, a new approach for controlled, in planta production of enzymes involved in lignocellulosic degradation using chemically inducible, transient, high level expression of cellulase enzymes produced in plants is highly desirable and the invention addresses this need.

SUMMARY OF THE INVENTION

The invention relates to a novel Cucumber mosaic virus (CMV) inducible viral amplicon (CMViva) expression system that allows for tightly regulated chemically-inducible expression of heterologous genes in plant hosts. Transient production of recombinant $\alpha_1$-antitrypsin (rAAT), a human blood protein, is shown in *Nicotiana benthamiana* leaves. High production levels are obtained by co-infiltrating leaves with *Agrobacterium tumefaciens* cells containing CMViva carrying the AAT gene and *A. tumefaciens* cells carrying a binary vector constitutively expressing the gene silencing suppressor p19 for example, from Tomato bushy stunt virus. Accumulation of up to thirty-fold more rAAT can be observed in leaves (24 mg per 100 g leaf tissue) when compared with the expression levels observed using the constitutive CaMV 35S promoter. Significantly, 70% of the rAAT produced using the CMViva expression system is found to be biologically active, i.e., a 170-fold increase in functional protein compared with the CaMV 35S expression system.

One aspect of the invention provides a plant expression system including a cucumber mosaic virus inducible viral amplicon for the expression of a heterologous gene in a plant or plant cell. The expression system may further include a cDNA coding for the cucumber mosaic virus which is operably linked to the heterologous gene. In one embodiment, the heterologous gene codes for a human blood protein. The expression system disclosed herein may be present in a transgenic plant or transgenic plant cell suspension culture in which the expression cassette has been stably incorporated into the plant genome and therefore inheritable by progeny.

Another aspect of the invention provides a method for producing a heterologous protein. The method may include: a) contacting a living plant, recently harvested tissue from a living plant, or plant cells with a bacterial cell containing the expression system described herein; b) exposing the plant, excised plant tissue, or plant cells to the chemical inducer; c) growing and/or incubating the contacted plant, excised plant, or plant cells for a time period sufficient to produce the heterologous protein; and d) harvesting the heterologous protein from the plant, excised plant tissue, plant cells or plant cell suspension culture broth. In a further embodiment, the method may include co-infiltrating the plant, excised plant tissue, or plant cells with a bacterial cell that contains the expression system and a bacterial cell that carries a binary vector constitutively expressing a gene silencing suppressor. In another embodiment, the bacterial cell includes *Agrobacterium tumefaciens* or the like. In yet another embodiment, the gene silencing suppressor is p19. In a further embodiment, the heterologous protein is a human protein. In yet a further embodiment, the heterologous protein is a cell wall modifying or degrading enzyme.

In one format, the invention relates to a cucumber mosaic virus inducible viral amplicon (CMViva) for the expression of heterologous genes in plants. In another format, the CMViva expression system can be a single binary plasmid containing the heterologous gene replacing the Coat Protein gene of the cucumber mosaic virus. In another format, the CMViva expression system can include two binary plasmids, wherein the first plasmid contains the cDNA encoding the CMV1a and CMV2a replicase genes, and the second plasmid contains the heterologous gene. The CMViva system is tightly regulated and inducible by the addition of estradiol.

One aspect of the invention provides the CMViva expression system that is tightly regulated and chemically inducible by the addition of a chemical such as, for example, mammalian steroid hormones such as estradiol. Regulation and induction of the system are conferred by the insertion of cDNAs of the estradiol inducible expression system XVE and a LEX operator operably linked to the CMV replicase gene. The binding of estradiol to the constitutively expressed XVE chimeric protein initiates a translocation and binding of the dimerized XVE chimeric protein to the LEX operator, whereby the binding of the LEX operator initiates the expression of the CMV replicase gene. The expression of the CMV replicase gene subsequently initiates the expression process of the heterologous gene. In another embodiment, steroidal or nonsteroidal agonist of insect hormones can be substituted for mammalian steroid hormones. For example, the insect ecdysone receptor gene switch reported by Tavva et al. 2006 could be used in place of the XVE/LEX operator.

Another aspect of the invention provides a method for producing a heterologous protein in a plant or plant cells by contacting the plant or plant cells with a bacterial cell, namely *Agrobacterium tumefaciens*, containing the expression system. The system may be stably integrated into the plant genome or transiently expressed. After introduction of the bacterial cells and exposure to the chemical inducer, the plants or plant cells may be grown, cultured, or incubated for a sufficient time period after which the heterologous protein is produced and harvested. Production of the heterologous protein is enhanced by introducing or co-infiltrating a plasmid containing the suppressor protein with the plasmid(s) containing expression system.

The heterologous gene can encode for other proteins, RNAs, or enzymes.

BRIEF DESCRIPTION OF THE TABLES AND DRAWINGS

The present invention is best understood when read in conjunction with the accompanying tables and figures. It is understood, however, that the invention is not limited to the specific embodiments disclosed in the tables or figures.

Table 1 depicts the list of primers used for amplification of DNA of various genes by PCR.

Table 2 depicts the comparison of *N. benthamiana* growth and rAAT production in bioreactors using different expression systems.

Table 3 depicts the comparison of recombinant AAT production using CMViva system by transient expression in *N. benthamiana* leaves with and without co-infiltration with the p19 gene silencing suppressor, and the comparison of transgenic *N. benthamiana* cell culture in a bioreactor (without p19 expression).

Table 4 depicts the comparison of recombinant human AAT production yield and quality using CMViva system by transient expression in *N. benthamiana* leaves and transgenic *N. benthamiana* cell culture in a bioreactor. a TSP=total soluble protein; b FW=Fresh tissue weight.

FIG. 1A depicts the CMViva expression system (modified from Mori; see Mori et al., 2001). This figure shows conceptually how the CMViva system works for the regulated, high level production of foreign proteins (e.g., AAT) in plant cells that have either been stably transformed or agroinfiltrated with *A. tumefaciens* containing the pCMV-SPAAT vector (see FIG. 2 below). In the absence of estradiol (E), only steps labeled with I occur and no product (AAT protein) is produced. Once estradiol is added, steps labeled with II occur as well as the steps labeled with I. First estradiol is taken up by the cells (step II 6); it binds to the constitutively expressed XVE chimeric protein (step II 7) creating a dimer (step II 8) that translocates to the nucleus and binds to the LexA operator (step II 9) allowing transcription of the CMV RNA1 cDNA (step II 10). The CMV RNA1 is transported out of the nucleus, and the ORF1A is translated (step II 12) to generate CMV 1a protein. Functional replicase is produced (step II 13) from CMV 1a, CMV 2a and host factors (H). Functional replicase enables replication of RNA 2 and RNA 3 (steps II 14 and II 15) as well as the generation of the subgenomic RNAs and transcription of the AAT gene (step II 16) followed by translation to produce the AAT protein product (step II 17). The CMV 2b protein is also expressed from subgenomic RNA only after step II 14, so it will not be produced in the uninduced state. We have deleted 57 nucleotides on the 5' end of the CMV RNA 1 cDNA so that the positive sense CMV RNA 1a cannot be replicated in the presence of functional replicase (as RNAs 2 and 3 are), as would normally occur in wild type CMV. This RNA can only serve as an mRNA to generate the 1a protein that then allows activation of CMV replication. Thus, the supply of the key 1a protein is not autocatalytic but controlled directly by step II 10. As a result this replication-impaired system is less sensitive to leakiness, safer, and more controllable.

FIG. 1B depicts linear maps of infectious clones pQCD1, pQCD2, and pQCD3, corresponding to CMV RNAs 1, 2, and 3, respectively, and binary vectors pER10, pDU97.1005, and pDU99.2215, containing the promoters, genes, and transcription terminators used for the construction of expression vectors pCMV, pCMV-SPAAT, pXVE-SPAAT and p35S-SPAAT (see the main text and FIG. 2 below). Restriction sites used for the cloning are shown as A, Asc I; B, BamH I; Bg, Bgl II; E, EcoR I; H, Hind III; N, Not I; Ns, Nsi I; S, Sal I; Sp, Spe I; and X, Xho I. Primer positions and directions are shown with a small arrow with primer names indicated below the arrow (see Table 1).

[a] pQCD2.1 was generated by linearizing pQCD2 with EcoR I and Spe I, filling with Klenow followed by self ligation.

[b] pQCD2.2 was generated by digesting pQCD2.1 with Hind III and Bgl II and ligating with pBluescript (Stratagene Inc, La Jolla, Calif.) cut with Hind III and Bam HI.

PCR products generated using primer pairs O14G10Pf: O15NPeaTr and O16NOpf:O17XSOpr were cloned into pGEM-T (Promega Inc, Madison, Wis.), released as Sal I/Nsi I and Nsi EcoR I fragments, and ligated along with EcoR I/BamH I fragment from pQCD1 into pQCD2.2, cut with Sal I/BamH I, in a four fragment ligation.

[d] PCR product generated using primer pair OQCD3-1: OQCD3-6 was digested with Xho I and Bgl II and ligated into pSP72 (Promega Inc.) cut with Xho I and Bgl II.

[e] PCR products generated using primer pairs OQCD3-1: OQCD3-2, OQCD3-3:OQCD3-4, and OQCD3-5:OQCD3-6, were cloned using TOPO-Zeroblunt cloning kit (Invitrogen, Carlsbad, Calif.) and the fragments were released as Xho EcoR I, EcoR I/BamH I and BamH I/Asc I fragments and ligated with pQA cut with Xho I and Asc I in a four fragment ligation.

FIG. 2 depicts the map of constructs used in this study: (A) pCMV; (B) pCMV-SPAAT; (C) pXVE-SPAAT; and (D) p35S-SPAAT. LB, left border; RB, right border; P, promoter; T, terminator.

FIG. 3 depicts immunoblot analysis of CMV CP: Comparison between CMV CP production in *N. benthamiana* plants infiltrated with *A. tumefaciens* cells containing pCMV. Lane 1: Control, CMV-infected *Cucurbita pepo* plants; lanes 2-4: pCMV+estradiol; lanes 5-7: pCMV-estradiol; lanes 8 and 9: healthy control plant.

[a] I=Plants treated with the estradiol inducer; (+) added; (−) not added; (*) non applicable.

FIG. 4 depicts immunoblot analysis of total and functional rAAT. Comparison between rAAT productions in plants infiltrated with *A. tumefaciens* cells containing p35S-SPAAT, pXVE-SPAAT, or pCMV-SPAAT when co-infiltrated with *A. tumefaciens* cells containing the silencing suppressor p19. (A) Comparison of total rAAT: lane 1, MultiMark molecular weight marker (Invitrogen, Carlsbad, Calif.); lane 2, healthy control plant; lane 3, p35S-SPAAT; lanes 4 and 5, pXVE-SPAAT; lanes 6 and 7, pCMV-SPAAT; lane 8, authentic human AAT (48 ng); lane 9 and 10, replicates of lane 4 and 6, respectively, using duplicate plants. (B) Band shift analysis for comparison of functional rAAT: lane 1, MultiMark molecular weight marker; lanes 2 and 3, p35S-SPAAT; lanes 4 and 5, pXVE-SPAAT; lanes 6 and 7, pCMV-SPAAT; lanes 8 and 9, human AAT standard (48 ng); lane 10, only PPE.

[a] I=Plants treated with the estradiol inducer; [b] PPE=Supernatant samples incubated with PPE before SDS-PAGE. (+) added; (−) not added; (*) non applicable.

FIG. 5 depicts immunoblot analysis of total and functional rAAT. Comparison between rAAT productions in plants infiltrated with *A. tumefaciens* cells containing pXVE-SPAAT or pCMV-SPAAT. (A) Comparison of total rAAT: lane 1, healthy control plant; lanes 2-5, pXVE-SPAAT; lanes 6-9, pCMV-SPAAT; lane 10, human AAT standard (48 ng). (B) Band shift analysis for comparison of functional rAAT: lanes 1-4, pXVE-SPAAT; lanes 5-8, pCMV-SPAAT; lanes 9 and 10, human AAT standard (48 ng).

[a] I=Plants treated with the estradiol inducer; [b] PPE=Supernatant samples incubated with PPE before SDS-PAGE; p19=Plants co-infiltrated with *A. tumefaciens* cells containing the p19 silencing suppressor. (+) added; (−) not added; (*) non applicable.

FIG. 6 depicts ELISA analysis of transiently expressed total and functional rAAT. Data are the average results from triplicate plants exposed to the same conditions at 2.5 days post-infiltration. Solid lines represent total rAAT and hatched lines represent functional rAAT. Error bars represent one standard deviation from triplicate assays performed on a given sample extract.

FIG. 7 depicts Western blotting and band shift analysis for comparison of total and functional rAAT production by three expression systems. Lane 1, human AAT standard; lane 2, human AAT incubated with procine pancreatic elastase (PPE); lane 3, Multimark molecular marker; lane 4, pCMV-spAAT (without induction); lane 5, pCMV-spAAT (with induction); lane 6, pCMV-spAAT (with induction) incubated with PPE; lane 7, pXVE-spAAT (without induction); lane 8, pXVE-spAAT (with induction); lane 9, pXVE-spAAT (with induction) incubated with PPE; lane 10, wild type *N. benthamiana*; lane 11, p35S-spAAT; lane 12, p35S-spAAT incubated with PPE. A band at 52 kDa corresponds to human AAT and a band at 48 kDa corresponds to rAAT. In the band shift assay, a band at a molecular weight around 75~80 kDa represent the human AAT-PPE covalent complex and a lower band is the cleaved product of AAT-PPE reaction.

a I=Plant cell culture treated with the estradiol inducer; b PPE=Supernatant samples incubated with PPE before SDS-PAGE; (+) added; (−) not added; (*) non applicable.

FIG. 8 depicts the effect of concentration of inducer (estradiol) on extracellular total and functional rAAT production from the XVE and CMViva inducible cell cultures.

Inducer solution was applied to inducible cell cultures (10 days old, 100 mL in a 250 mL flask) at a final concentration of 0, 0.1, 0.5, 1, 2.5, 5, 10, 25, 50 or 100 μM estradiol. Samples were taken at day 8 after starting induction phase for AAT ELISA analysis. Error bars represent one standard deviation of measurements obtained from duplicate experiments.

FIG. 9 depicts the effect of timing of induction on extracellular total and functional rAAT production in the XVE inducible cell cultures. Inducer solution was added into XVE cell culture (100 mL culture in a 250 mL flask) to a final concentration of 10 μM estradiol at day 5, 8, 11 or 14 after inoculation. Samples were analyzed by AAT ELISA. Dashed lines represent the time of addition of inducer at day 5, 8, 11 or 14 after inoculation.

FIG. 10 depicts the effect of timing of induction on extracellular total and functional rAAT production in the CMViva inducible cell cultures. Inducer solution was added into CMViva cell culture (100 mL culture in a 250 mL flask) to a final concentration of 10 μM estradiol at day 5, 8, 11 or 14 after inoculation. Samples were analyzed by AAT ELISA. Dashed lines represent the time of addition of inducer at day 5, 8, 11 or 14 after inoculation.

Figure 14:
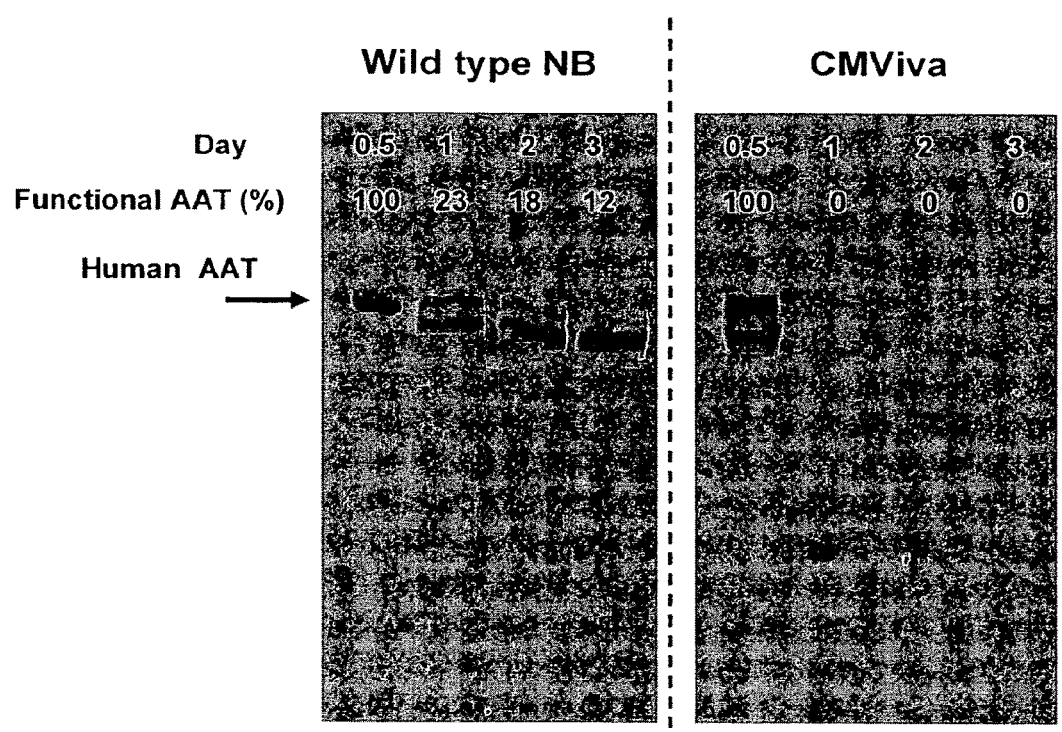

FIG. 14 depicts the Western blotting analysis of the stability and degradation of human AAT in cell-free conditioned medium prepared from 7 day old wild type *N. benthamiana* or CMViva transgenic plant cell cultures. Day represents the time after incubation. Functional AAT (%) indicates the relative amount of functional human AAT remaining as a percentage of the initial concentration determined by functional AAT ELISA.

Figure 15:
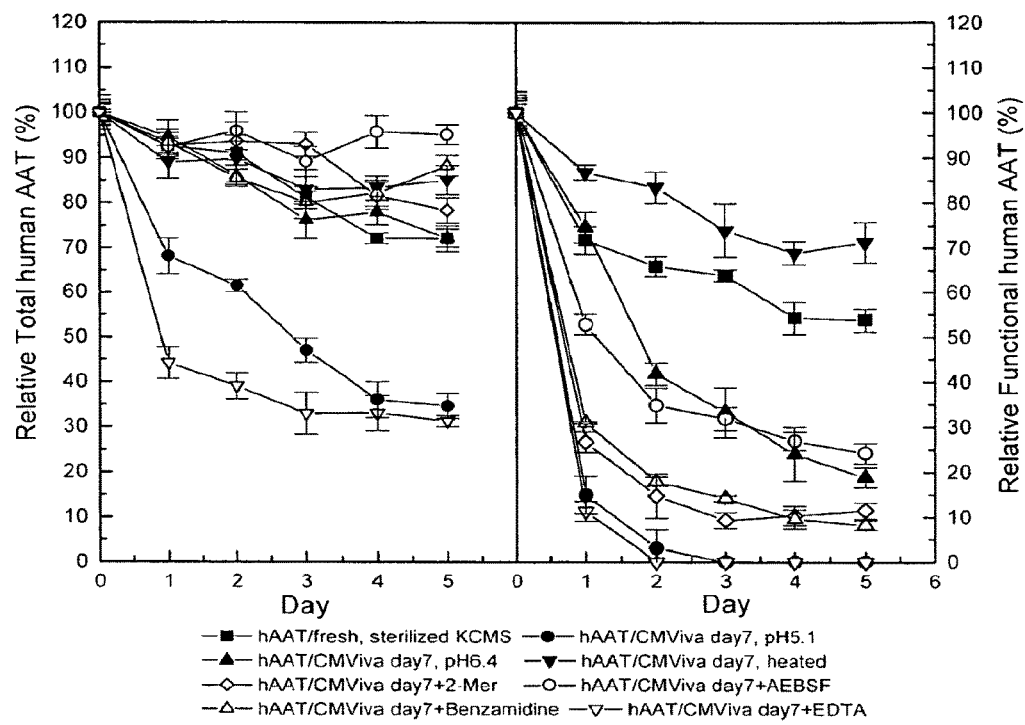

FIG. 15 depicts the kinetic profiling of the stability and degradation of human AAT in cell-free conditioned medium prepared from 7 day old CMViva transgenic plant cell cultures. Day represents the time after incubation. Relative total and functional human AAT (%) indicates the relative amount of total and functional human AAT remaining as a percentage of the initial concentration determined by AAT ELISA. hAAT/fresh, sterilized KCMS: human AAT incubated in fresh and filter sterilized KCMS medium; hAAT/CMViva day 7, pH 5.1: human AAT incubated in cell-free 7 day old CMViva cell cultured medium with pH 5.1; hAAT/CMViva day 7, pH 6.4: human AAT incubated in cell-free 7 day old CMViva cell cultured medium with changed pH 6.4; hAAT/CMViva day 7, heated: human AAT incubated in cell-free 7 day old CMViva cell cultured medium that was heated at boiling water for 30 min prior to the addition of human AAT; hAAT/CMViva day 7+2-Mer: human AAT incubated in cell-free 7 day old CMViva cell cultured medium containing 2-mercaptoethylamine-HCl (aminopeptidase inhibitor); hAAT/CMViva day 7+AEBSF: human AAT incubated in cell-free 7 day old CMViva cell cultured medium containing AEBSF (broad spectrum serine and cysteine proteases inhibitor); hAAT/CMViva day 7+Benzamidine: human AAT incubated in cell-free 7 day old CMViva cell cultured medium containing benzamidine-HCl (serine protease inhibitor); hAAT/CMViva day 7+EDTA: human AAT incubated in cell-free 7 day old CMViva cell cultured medium containing EDTA (a metal ion chelator, anti-metalloproteinase). The final working concentration for each protease inhibitor is 10 mM. Error bars represent one standard deviation of measurements obtained from duplicate experiments.

Figures 16A, 16B:
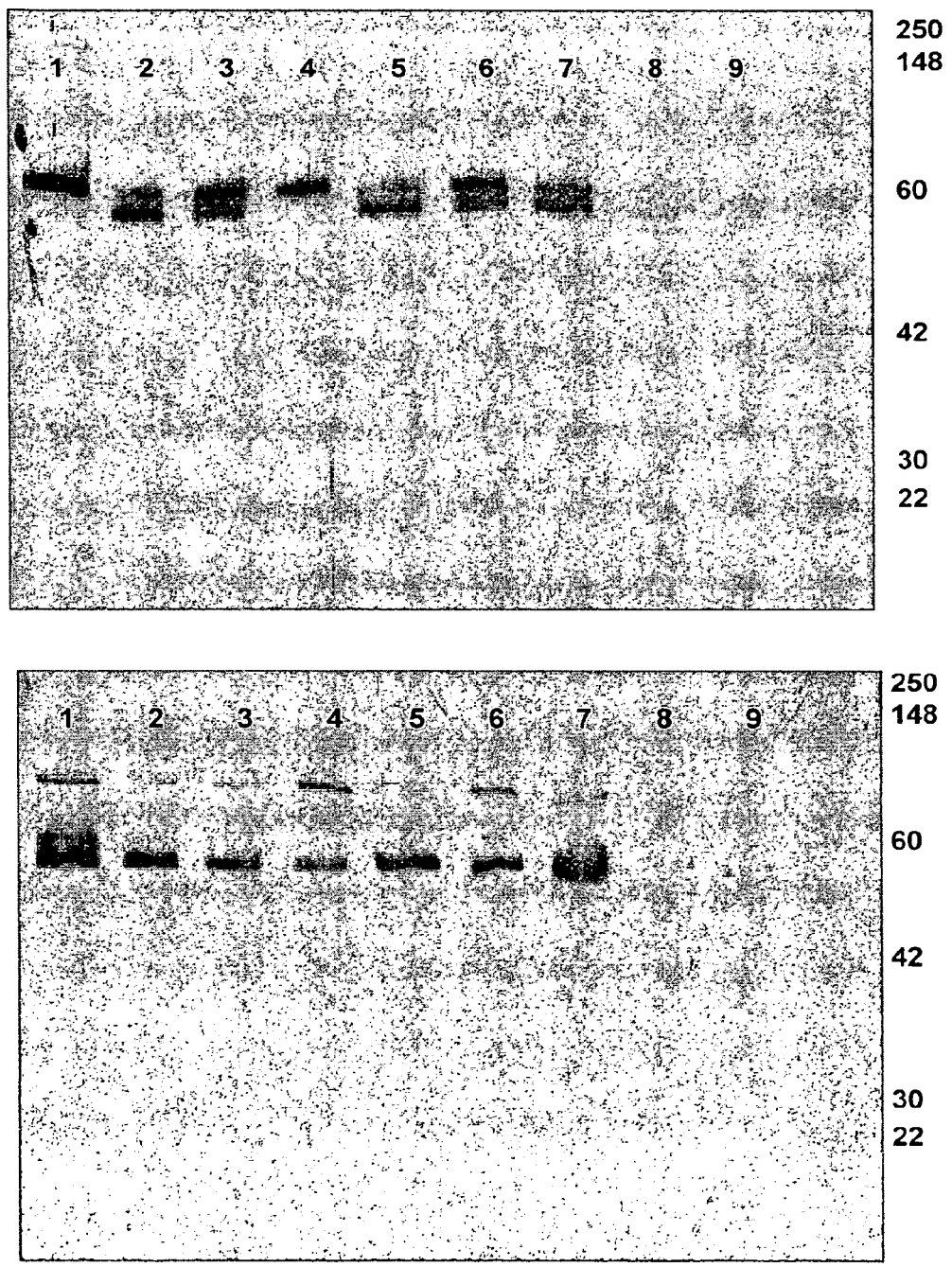

FIG. 16A depicts the Western blotting analysis of human AAT incubated in various cell-free conditioned medium prepared from 7 day old CMViva transgenic plant cell cultures. Samples were taken on 1 day after incubation. Lane 1, human AAT standard; lane 2, human AAT incubated in fresh and sterilized KCMS medium; lane 3, human AAT incubated in cell-free conditioned medium with changed pH 6.4; lane 4, human AAT incubated in cell-free conditioned medium that was heated at boiling water for 30 min prior to the addition of human AAT; lane 5, human AAT incubated in cell-free conditioned medium containing 2-mercaptoethylamine-HCl; lane 6, human AAT incubated in cell-free conditioned medium containing AEBSF; lane 7, human AAT incubated in cell-free conditioned medium containing benzamidine-HCl; lane 8, human AAT incubated in cell-free conditioned medium containing EDTA; lane 9, human AAT incubated in cell-free conditioned medium with original pH 5.1; lane 10, multimark molecular marker.

FIG. 16B depicts band shift analysis of the human AAT incubated in various cell-free conditioned medium prepared from 7 day old CMViva transgenic plant cell cultures. Samples were taken on 1 day after incubation. The layout of lanes is the same as FIG. 16A.

Figure 17:
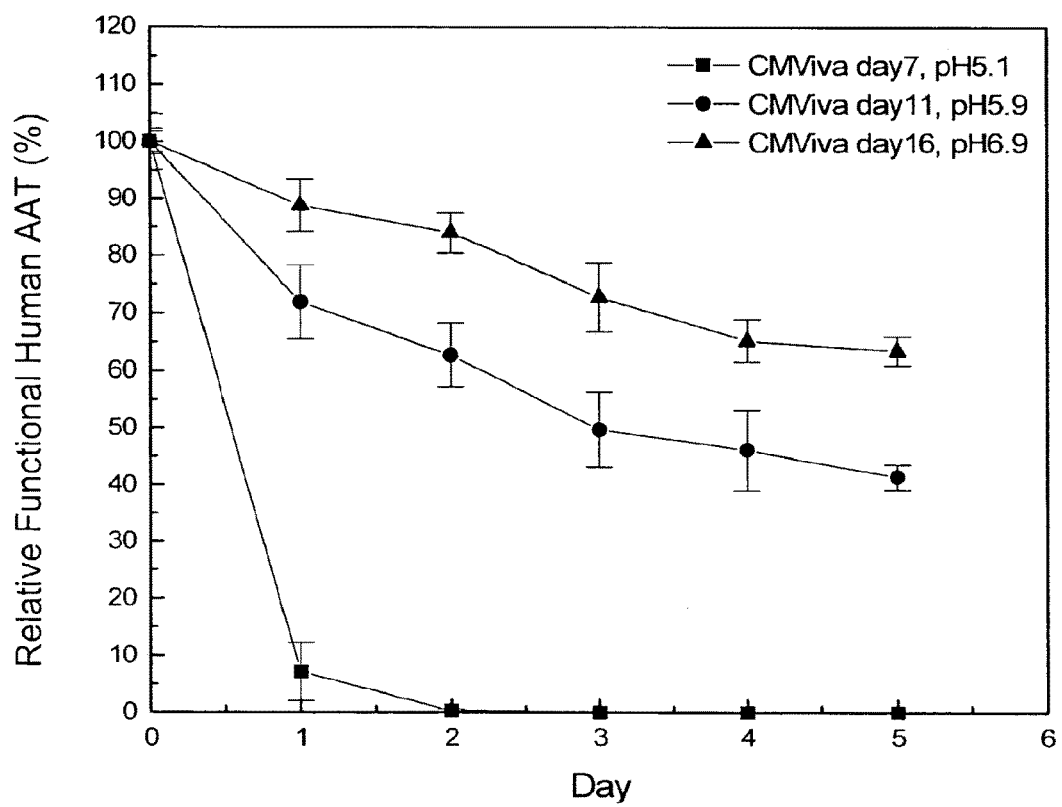

FIG. 17 depicts kinetics of functional human AAT protein stability in cell-free conditioned medium collected from different ages of CMViva cell cultures including 7 days (medium pH 5.1), 11 days (medium pH 5.9) or 16 days (medium pH 6.9) old post-subculture. Error bars represent one standard deviation of measurements obtained from duplicate experiments.

Figure 18:
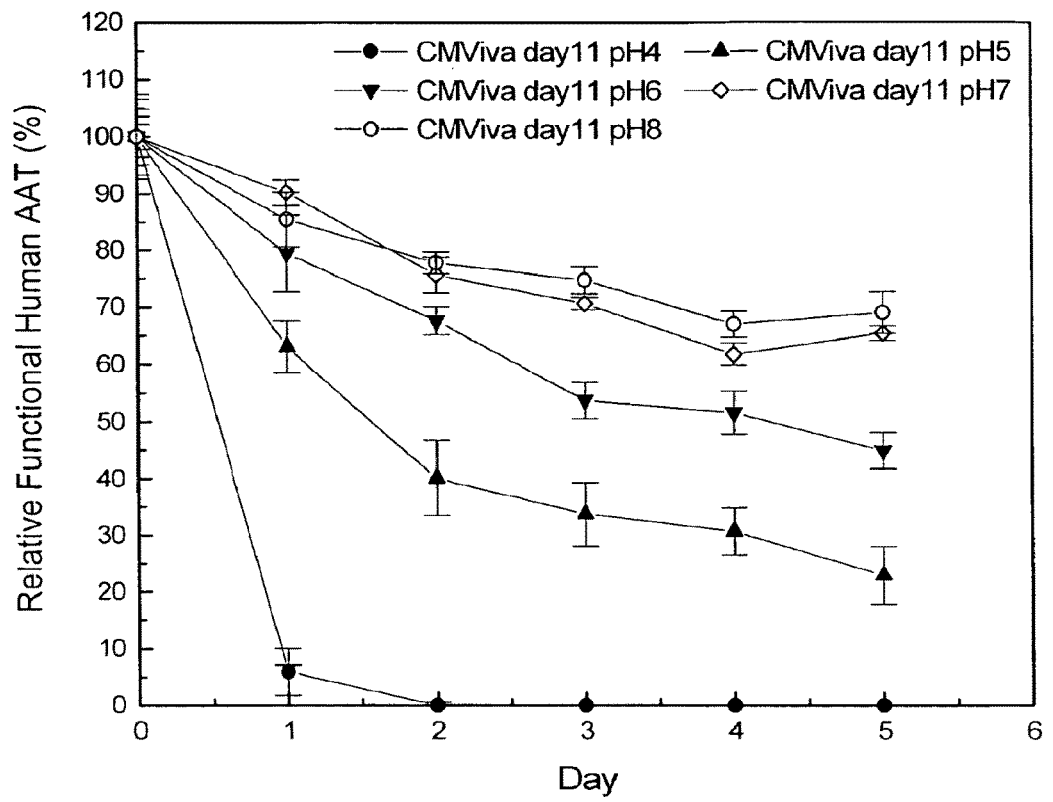

FIG. 18 depicts the degradation profile of functional human AAT in 11 days old conditioned CMViva cell culture medium (free of cell) that was regulated to different medium pH (4, 5, 6, 7 or 8). Error bars represent one standard deviation of measurements obtained from duplicate experiments.

Figure 19:
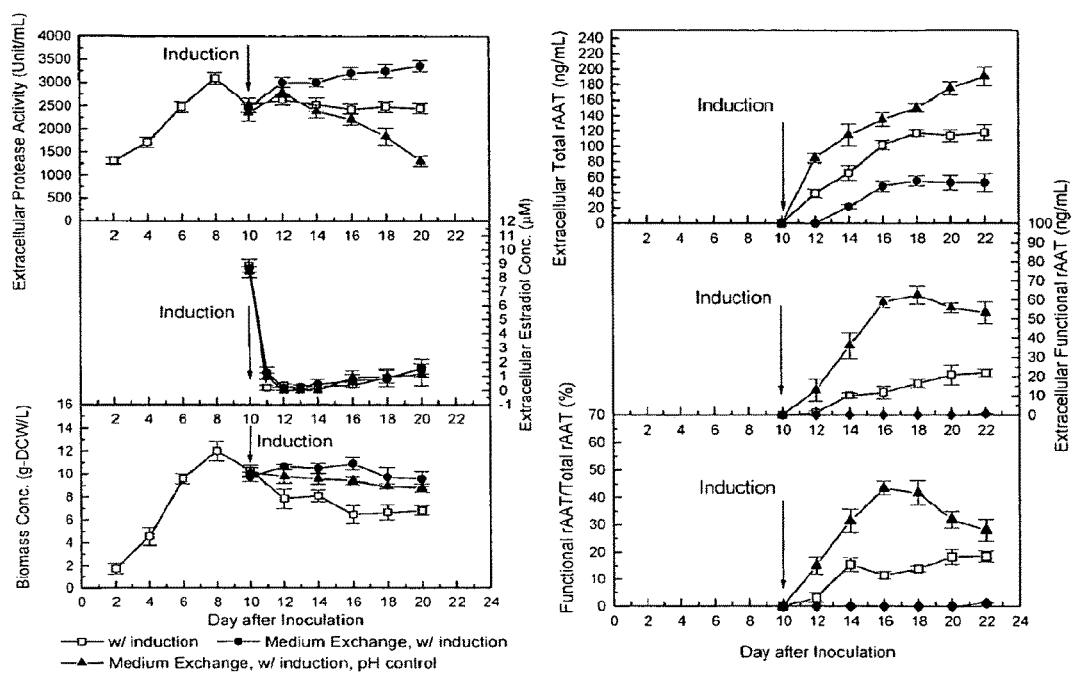

FIG. 19 depicts the effects of medium exchange and pH control on rAAT production in CMViva cell cultures in flask. Arrow indicates the timing of induction at day 10 after inoculation. Error bars represent one standard deviation of measurements from duplicate experiments.

Figure 20:
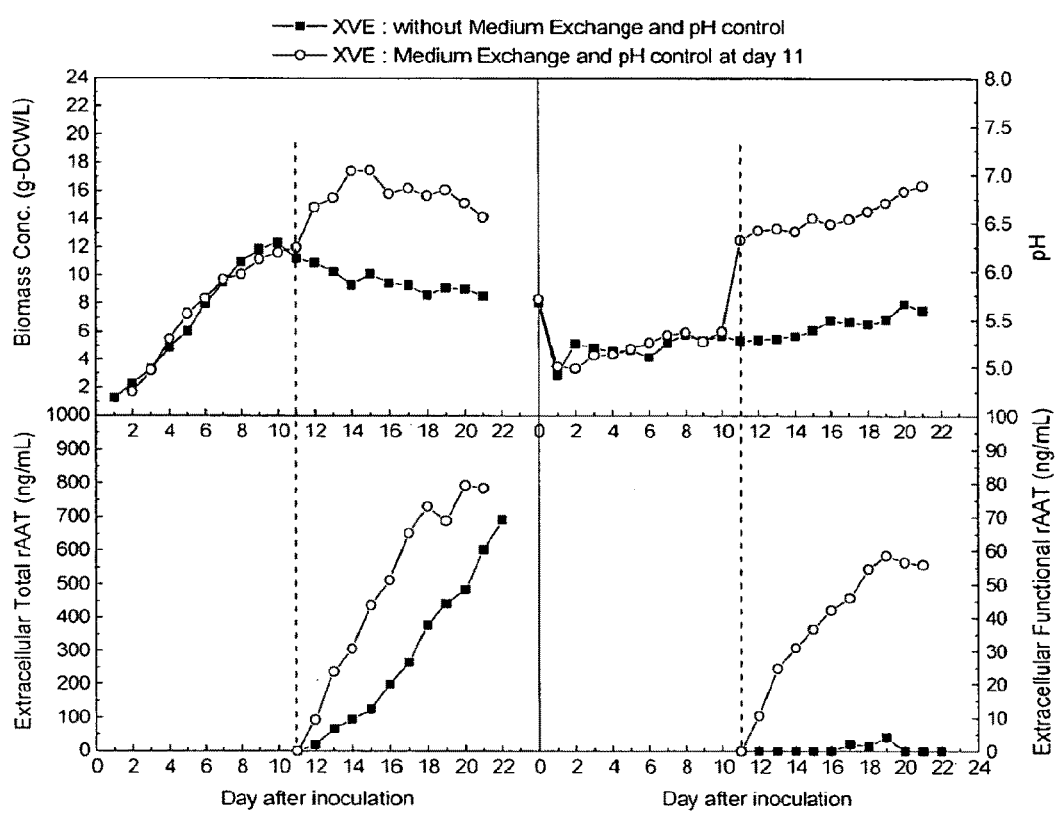

FIG. 20 depicts the effects of pH control on cell growth and rAAT production in XVE cell cultures in a bioreactor. Dashed lines represent the timing of induction at day 11 after inoculation.

Figure 21:
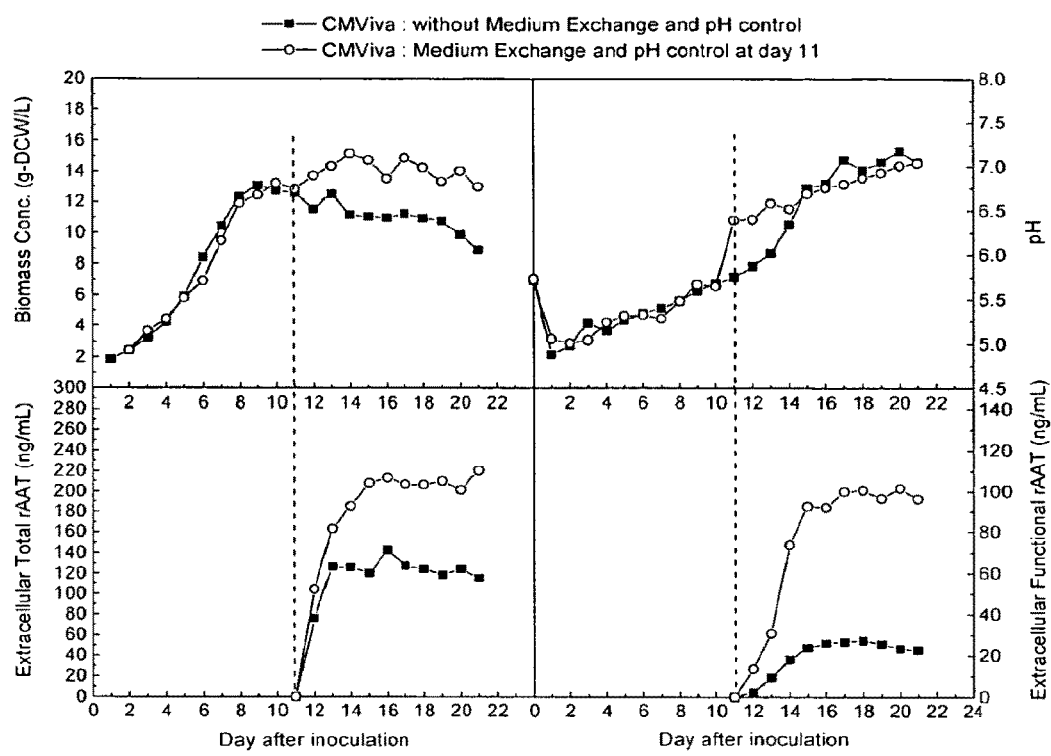

FIG. 21 depicts the effects of pH control on cell growth and rAAT production in CMViva cell cultures in a bioreactor. Dashed lines represent the timing of induction at day 11 after inoculation.

Figure 22:
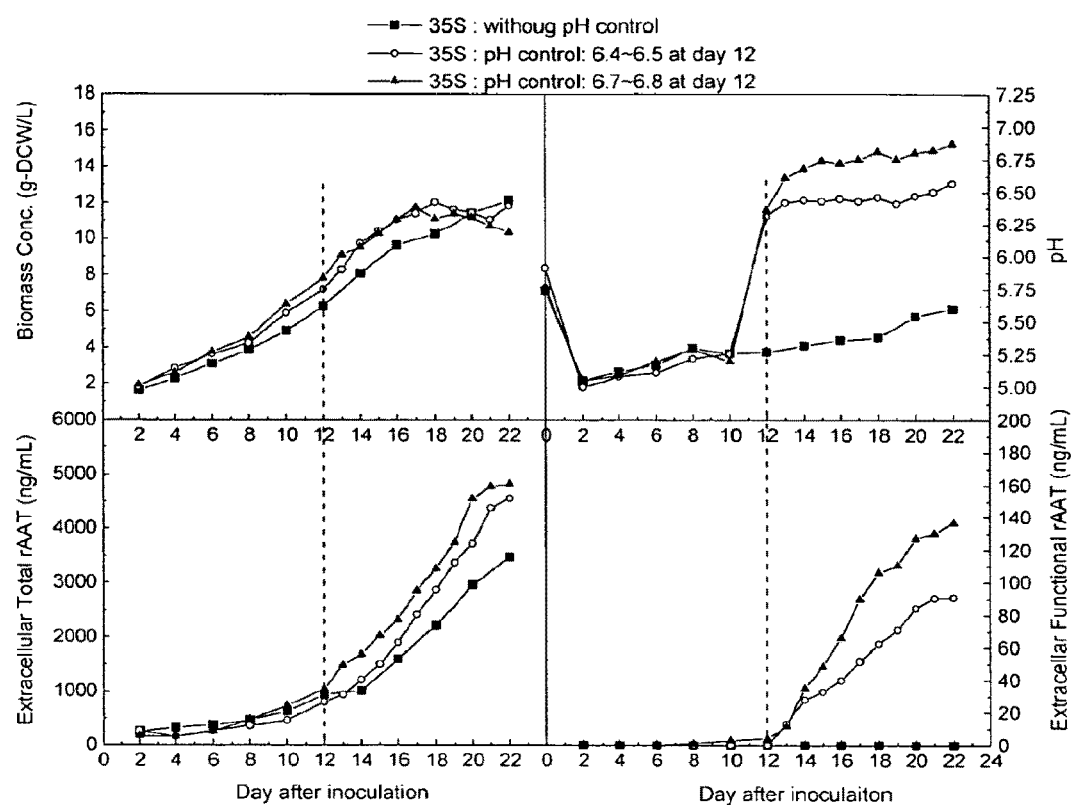

FIG. 22 depicts the effects of pH control on cell growth and rAAT production in 35S cell cultures in a bioreactor. Dashed lines represent the pH control timing at day 12 or 16 after inoculation.

Figure 23:
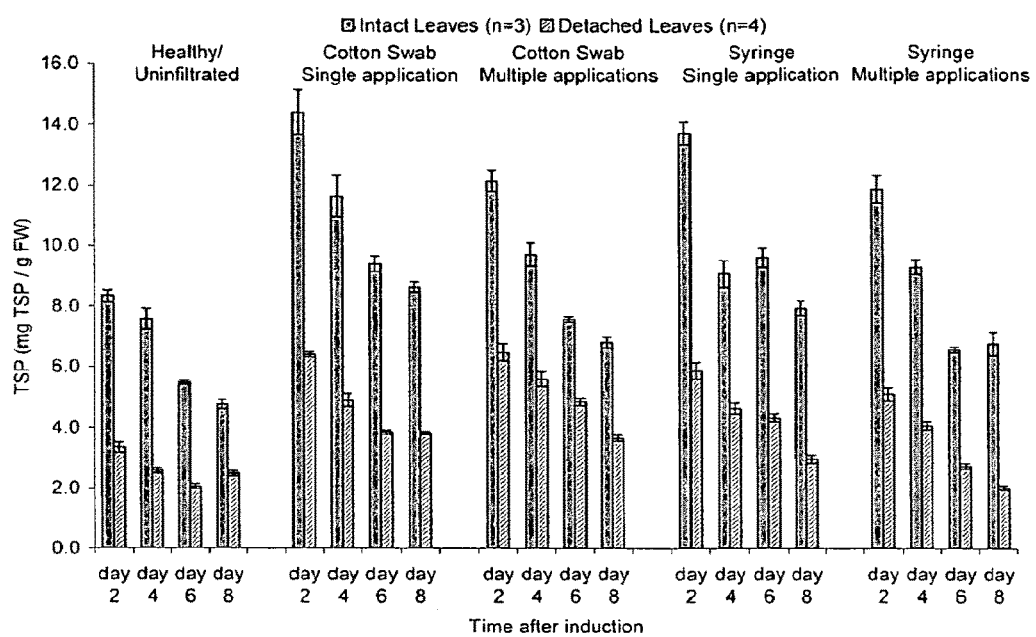

FIG. 23 depicts the Bradford analysis of TSP in samples from *N. benthamiana* leaves exposed to various induction treatment methods: either no induction, a single topical application, multiple topical applications, a single pressure injection, or multiple pressure injections. Data are grouped by method of inducer application and are the average results from triplicate (for intact) of quadruplicate (for detached) plant leaves exposed to the same conditions. Solid-filled lines represent production levels in intact leaves and hatched lines represent production levels in detached leaves. Error bars represent one standard deviation from triplicate assays performed on samples of triplicate or quadruplicate plant leaves.

Figure 24:
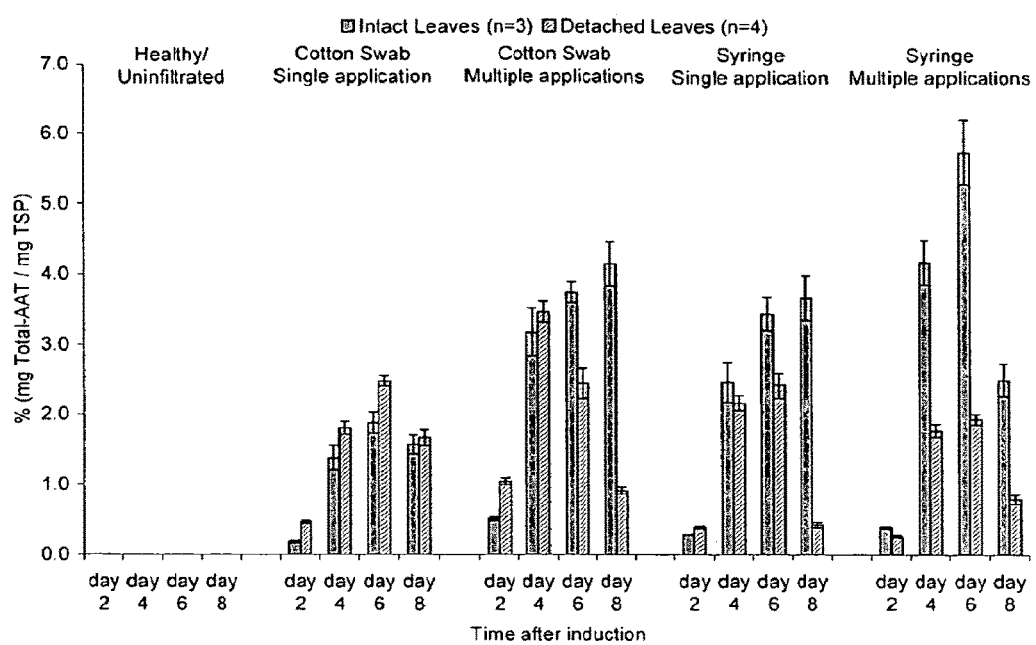

FIG. 24 depicts the ELISA analysis of transiently expressed total rAAT in samples from *N. benthamiana* leaves exposed to various induction treatment methods: either no induction, a single topical application, multiple topical applications, a single pressure injection, or multiple pressure injections. Data are grouped by method of inducer application and are the average results from triplicate (for intact) of quadruplicate (for detached) plant leaves exposed to the same conditions. Solid-filled lines represent production levels in intact leaves and hatched lines represent production levels in detached leaves. Error bars represent one standard deviation from triplicate assays performed on samples of triplicate or quadruplicate plant leaves.

Figure 25:
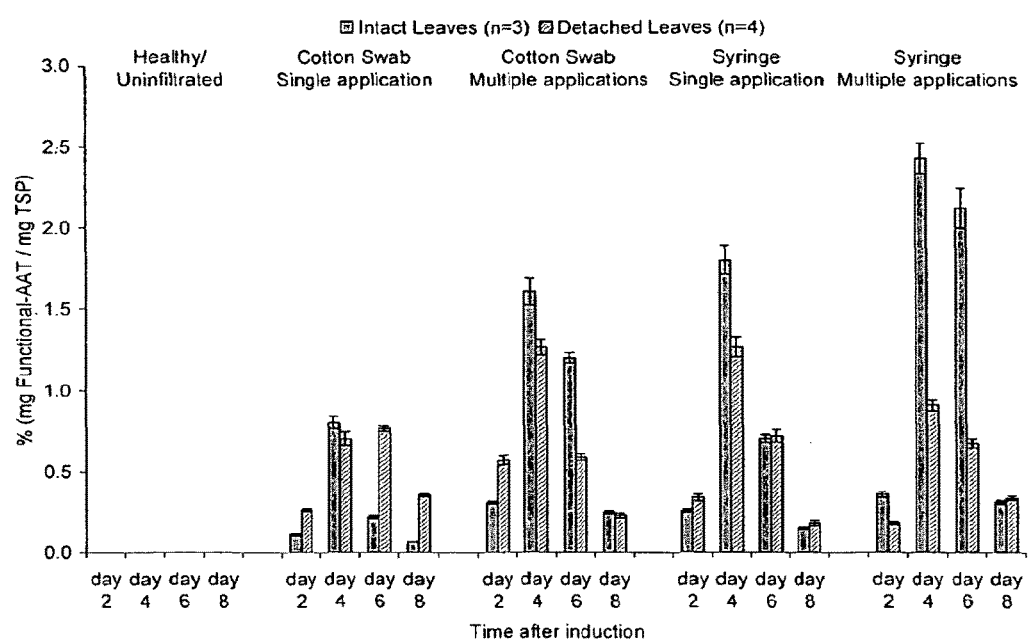

FIG. 25 depicts the ELISA analysis of transiently expressed total rAAT in samples from *N. benthamiana* leaves exposed to various induction treatment methods: either no induction, a single topical application, multiple topical applications, a single pressure injection, or multiple pressure injections. Data are grouped by method of inducer application and are the average results from triplicate (for intact) of quadruplicate (for detached) plant leaves exposed to the same conditions. Solid-filled lines represent production levels in intact leaves and hatched lines represent production levels in detached leaves. Error bars represent one standard deviation from triplicate assays performed on samples of triplicate or quadruplicate plant leaves.

Figure 26:
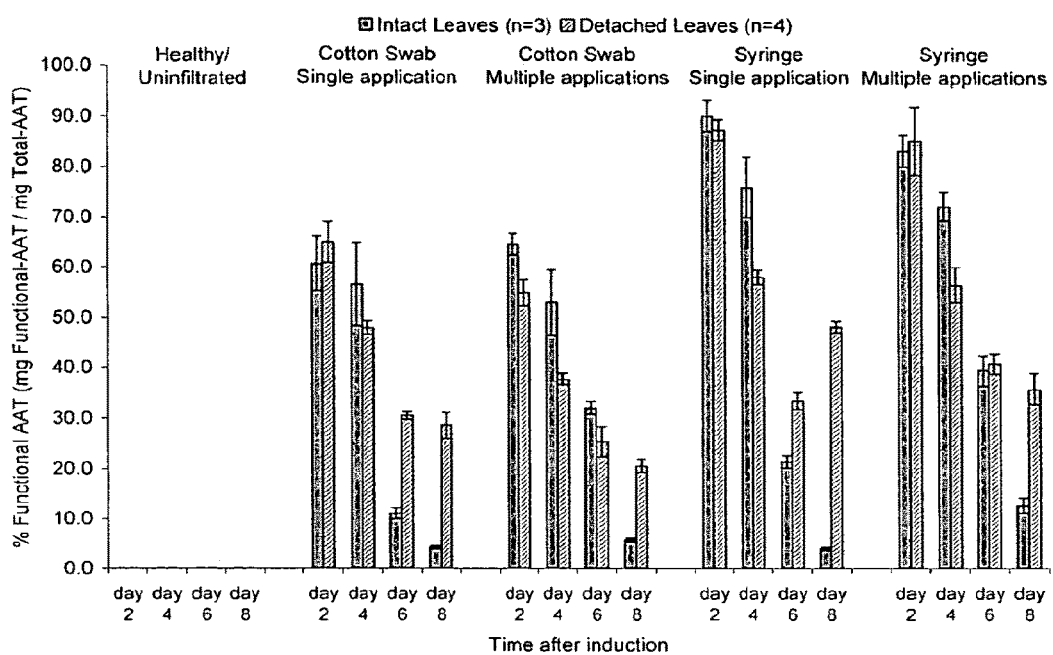

FIG. 26 depicts the ELISA analysis of transiently expressed biologically functional rAAT in samples from *N. benthamiana* leaves exposed to various induction treatment methods: either no induction, a single topical application, multiple topical applications, a single pressure injection, or multiple pressure injections. Data are grouped by method of inducer application and are the average results from triplicate (for intact) of quadruplicate (for detached) plant leaves exposed to the same conditions. Solid-filled lines represent production levels in intact leaves and hatched lines represent production levels in detached leaves. Error bars represent one standard deviation from triplicate assays performed on samples of triplicate or quadruplicate plant leaves.

Figure 27:
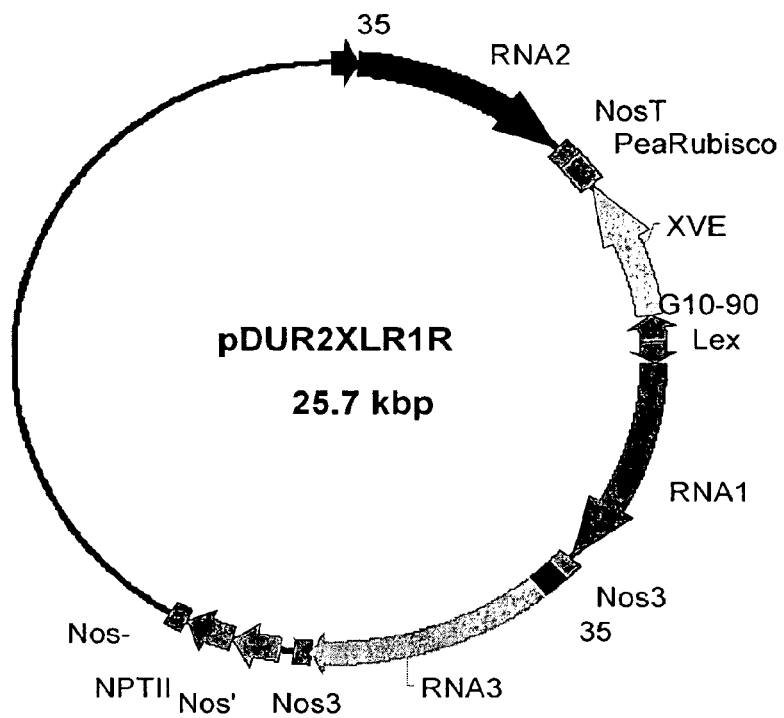

FIG. 27 depicts the first of the two binary plasmids of in the alternative construction of the CMViva expression system (Example 2).

Figure 28:
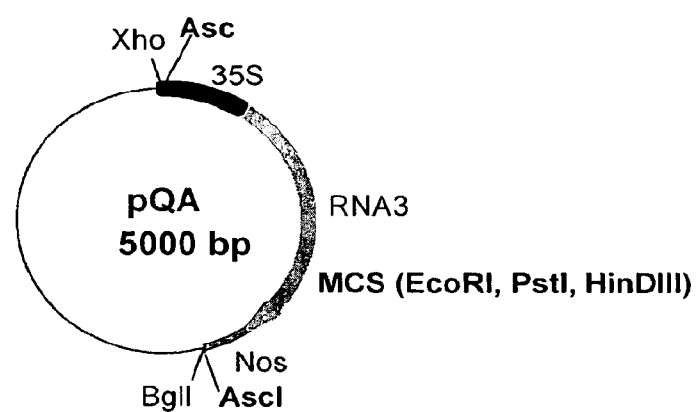

FIG. 28 depicts the second of the two binary plasmids of in the alternative construction of the CMViva expression system (Example 2).

DETAILED DESCRIPTION OF THE INVENTION a.) a Chemically Inducible Plant Viral Amplicon Expression System

Figure 1A:
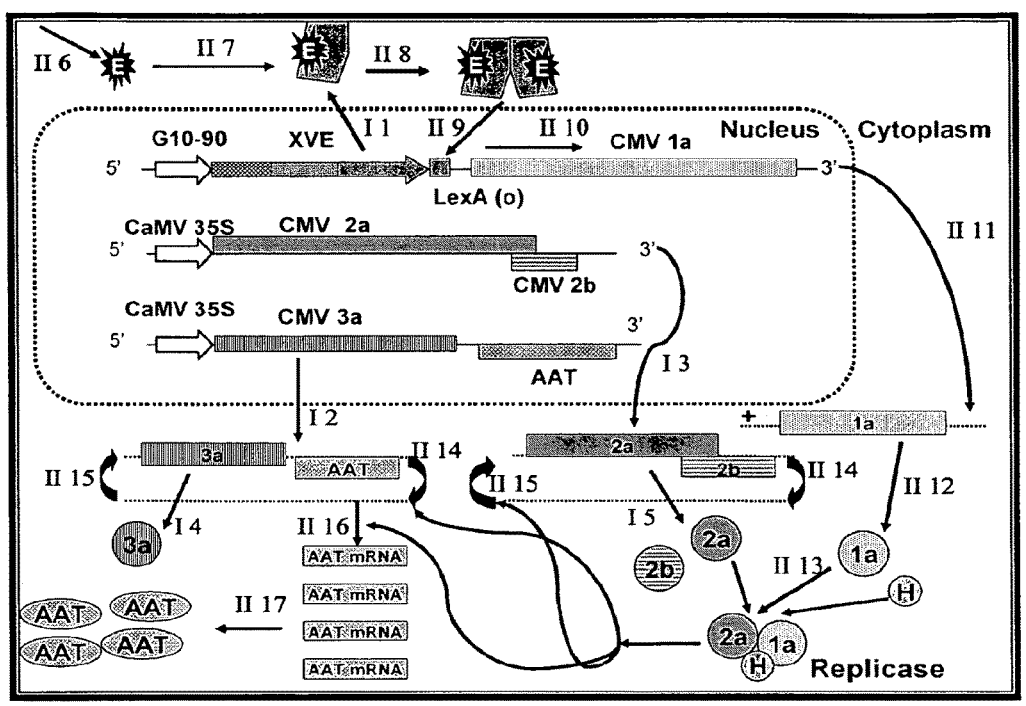

The invention relates to a novel chemically inducible plant viral amplicon (CMViva) expression system that permits controllable, high level expression of foreign genes in plant hosts. This system can be used in transient agro-infiltration in intact, living plants, recently harvested plant tissues (e.g. leaves, stems), or plant cells, and also for stable integration into the genomes of plants or plant cells to allow production of a protein, enzyme or RNA of interest. This system provides a major advantage over existing plant expression systems because it allows for consistent expression of foreign or heterologous proteins in plant hosts. The invention encompasses genetically engineered plant cells that contain modified complementary DNAs (cDNAs) representing the complete tripartite genome of Cucumber mosaic virus (CMV), in which the CMV coat protein gene has been replaced by a target gene of interest, which along with other modifications ensure that no infectious CMV virus is generated. In this system, one of the key CMV-encoded protein components of the viral replicase is under the control of a relatively tightly regulated chemically-inducible promoter. As such, the recombinant viral amplicons are only produced intracellularly and under specific induction conditions (FIG. 1A).

One aspect of the invention provides the CMViva expression system that is tightly regulated and chemically inducible by the addition of a chemical such as, for example, mammalian steroid hormones such as estradiol. When estradiol is the chemical inducer, regulation and induction is achieved by the insertion of cDNAs of the estradiol inducible expression system XVE and a LEX operator. The binding of estradiol to the constitutively expressed XVE chimeric protein initiates a translocation and binding of the dimerized XVE chimeric protein to the LEX operator, whereby the binding of the LEX operator initiates the expression of the CMV replicase gene. The expression of the CMV replicase gene subsequently initiates the expression process of the heterologous gene.

In a further embodiment, steroidal or nonsteroidal agonist of insect hormones can be substituted for mammalian steroid hormones. For example, the insect ecdysone receptor (EcR) gene switch reported by Tavva et al. 2006 could be used in place of the XVE/LEX operator to create a EcR-based inducible gene expression system. In this system, methoxyfenozide is the chemical inducer, whereby the presence of methoxyfenozide induces the expression a heterologous gene.

Another aspect of the invention provides the CMViva expression system operably linked to a gene of interest (e.g., a bacterial, plant, yeast, fungi, or animal). In one embodiment, a plant (e.g., leaf, stem, etc.) is infiltrated with bacterial (*Agrobacterium tumefaciens*) cells that contain the CMViva expression system operably linked to a gene of interest (e.g., a human gene that codes for a human protein). In another embodiment, a plant (e.g., leaf, stem, etc.) is infiltrated with bacterial cells that contain the CMViva expression system operably linked to a gene of interest (e.g., a human gene that codes for a human protein) and bacterial cells that carry a binary vector that constitutively expresses the gene silencing suppressor p19, the gene silencing suppressor p19 can be from Tomato bushy stunt virus. In a further embodiment, the CMViva is stably integrated into a plant or plant cells of interest.

b.) Definitions

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

Throughout this disclosure, various publications, patents and published patent specifications are referenced. The disclosures of these publications, patents and published patent specifications are hereby incorporated by reference into the present disclosure to more fully describe the state of the art to which this invention pertains. The practice of the present invention will employ, unless otherwise indicated, conventional techniques of plant breeding, immunology, molecular biology, microbiology, cell biology and recombinant DNA, which are within the skill of the art. See, e.g., Sambrook, Fritsch and Maniatis, MOLECULAR CLONING: A LABORATORY MANUAL, 2nd edition (1989); CURRENT PROTOCOLS IN MOLECULAR BIOLOGY [(F. M. Ausubel, et al. eds., (1987)]; PLANT BREEDING: PRINCIPLES AND PROSPECTS (Plant Breeding, Vol. 1) M. D. Hayward, N. O. Bosemark, I. Romagosa; Chapman & Hall, (1993.); Coligan, Dunn, Ploegh, Speicher and Wingfeld, eds. (1995) CURRENT PROTOCOLS IN PROTEIN SCIENCE (John Wiley & Sons, Inc.); the series METHODS IN ENZYMOLOGY (Academic Press, Inc.): PCR 2: A PRACTICAL APPROACH (M. J. MacPherson, B. D. Hames and G. R. Taylor eds. (1995)], Harlow and Lane, eds. (1988) ANTIBODIES, A LABORATORY MANUAL, and ANIMAL CELL CULTURE [R. I. Freshney, ed. (1987)].

Unless otherwise noted, technical terms are used according to conventional usage. Definitions of common terms in molecular biology may be found in Lewin, Genes V, published by Oxford University Press, 1994 (SBN 0-19-854287-9); Kendrew et al. (eds.), The Encyclopedia of Molecular Biology, published by Blackwell Science Ltd., 1994 (SBN 0-632-02182-9); and Robert A. Meyers (ed), Molecular Biology and Biotechnology, a Comprehensive Desk Reference, published by VCH Publishers, Inc., 1995 (ISBN 1-56081-569-8); Ausubel et al. (1987) Current Protocols in Molecular Biology, Green Publishing; Sambrook et al. (1989) Molecular Cloning: A Laboratory Manual, Cold Spring Harbor, N.Y.

In order to facilitate review of the various embodiments of the invention, the following definitions are provided:

Non-naturally Occurring Plant: A non-naturally occurring plant is a plant that does not occur in nature without human intervention.

Sequence Identity: The similarity between two nucleic acid sequences or two amino acid sequences is expressed in terms of sequence identity (or, for proteins, also in terms of sequence similarity). Sequence identity is frequently measured in terms of percentage identity; the higher the percentage, the more similar the two sequences are. Homologs and variants of the nucleic acid molecules described herein may be used in the present invention. Homologs and variants of these nucleic acid molecules will possess a relatively high degree of sequence identity when aligned using standard methods. Such homologs and variants will hybridize under high stringency conditions to one another. Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI Website. A description of how to determine sequence identity using this program is available at the NCBI website.

Homologs of the disclosed protein and nucleic acid sequences are typically characterized by possession of at least 40% sequence identity counted over the full length alignment with the amino acid sequence of the disclosed sequence using the NCBI Blast 2.0, gapped blastp set to default parameters. The adjustable parameters are preferably set with the following values: overlap span 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. Proteins with even greater similarity to the reference sequences will show increasing percentage identities when assessed by this method, such as at least about 50%, at least about 60%, at least about 70%, at least about 75%, at least about 80%, at least about 90% or at least about 95% sequence identity.

The alignment may include the introduction of gaps in the sequences to be aligned. In addition, for sequences which contain either more or fewer amino acids than the protein encoded by the sequences in the figures, it is understood that in one embodiment, the percentage of sequence identity will be determined based on the number of identical amino acids in relation to the total number of amino acids. Thus, for example, sequence identity of sequences shorter than that shown in the figures as discussed below, will be determined using the number of amino acids in the longer sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described herein for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region. As will be appreciated by those skilled in the art, the sequences of the present invention may contain sequencing errors. That is, there may be incorrect nucleotides, frameshifts, unknown nucleotides, or other types of sequencing errors in any of the sequences; however, the correct sequences will fall within the homology and stringency definitions herein.

High Stringency: High stringency conditions refers to hybridization to filter-bound DNA in 5×SSC, 2% sodium dodecyl sulfate (SDS), 100 ug/ml single stranded DNA at 55-65° C., and washing in 0.1×SSC and 0.1% SDS at 60-65° C.

Vector: A nucleic acid molecule as introduced into a host cell, thereby producing a transformed host cell. A vector may include one or more nucleic acid sequences that permit it to replicate in one or more host cells, such as origin(s) of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, plant or animal cell, including transfection with viral vectors, transformation by *Agrobacterium*, with plasmid vectors, and introduction of naked DNA by electroporation, lipofection, and particle gun acceleration and includes transient as well as stable transformants.

Isolated: An "isolated" biological component (such as a nucleic acid or protein or organelle) has been substantially separated or purified away from other biological components in the cell or the organism in which the component naturally occurs, i.e., other chromosomal and extra chromosomal DNA and RNA, proteins and organelles. Nucleic acids and proteins that have been "isolated" include nucleic acids and proteins purified by standard purification methods. The term embraces nucleic acids including chemically synthesized nucleic acids and also embraces proteins prepared by recombinant expression in vitro or in a host cell and recombinant nucleic acids as defined below.

Operably linked: A first nucleic acid sequence is operably linked with a second nucleic acid sequence when the first nucleic acid sequence is placed in a functional relationship with the second nucleic acid sequence. For instance, a promoter is operably linked to a protein coding sequence if the promoter affects the transcription or expression of the protein coding sequence. Generally, operably linked DNA sequences are contiguous and, where necessary, join two protein coding regions in the same reading frame. With respect to polypeptides, two polypeptide sequences may be operably linked by covalent linkage, such as through peptide bonds or disulfide bonds.

Recombinant: By "recombinant nucleic acid" herein is meant a nucleic acid that has a sequence that is not naturally occurring or has a sequence that is made by an artificial combination of two otherwise separated segments of sequence. This artificial combination is often accomplished by chemical synthesis or, more commonly, by the artificial manipulation of nucleic acids, e.g., by genetic engineering techniques, such as by the manipulation of at least one nucleic acid by a restriction enzyme, ligase, recombinase, and/or a polymerase. Once introduced into a host cell, a recombinant nucleic acid is replicated by the host cell, however, the recombinant nucleic acid once replicated in the cell remains a recombinant nucleic acid for purposes of this invention. By "recombinant protein" herein is meant a protein produced by a method employing a recombinant nucleic acid. As outlined above "recombinant nucleic acids" and "recombinant proteins" also are "isolated" as described above.

Ortholog: Two nucleotide or amino acid sequences are orthologs of each other if they share a common ancestral sequence and diverged when a species carrying that ancestral sequence split into two species, sub species, or cultivars. Orthologous sequences are also homologous sequences. Orthologous sequences hybridize to one another under high-stringency conditions. The term "polynucleotide", "oligonucleotide", or "nucleic acid" refers to a polymeric form of nucleotides of any length, either deoxyribonucleotides or ribonucleotides, or analogs thereof. The terms "polynucleotide" and "nucleotide" as used herein are used interchangeably. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A "fragment" or "segment" of a nucleic acid is a small piece of that nucleic acid.

c.) Uses of the Non-Naturally Occurring Plants of the Invention

The non-naturally occurring plants of the invention are specifically useful in that they can be employed as hosts for production of foreign or heterologous proteins. As such, the non-naturally occurring plants can be used to provide various amounts of foreign protein content, including therapeutic proteins that can be used as drugs, diagnostic proteins that can be used as markers, and the like. Examples of a foreign protein that can be produced in a plant are cellulases for controlled in-planta degradation of lignocellulose for use as a feedstock for ethanol production and others. As defined herein, foreign or heterologous protein content means that the plant produces a protein that does not occur within the natural plant. The non-naturally occurring plants of this invention employ the CMViva expression system that allows for tightly regulated chemically-inducible expression of protein coding genes in the non-naturally occurring plants. In one embodiment, a plant (e.g., leaf, stem, etc.) is infiltrated with bacterial or *Agrobacterium tumefaciens* cells that contain the CMViva expression system operably linked to a gene of interest (e.g., a human gene that codes for a human protein). In another embodiment, a plant (e.g., leaf, stem, etc.) is infiltrated with bacterial or *Agrobacterium tumefaciens* cells that contain the CMViva expression system operably linked to a gene of interest (e.g., a human gene that codes for a human protein) and bacterial or *Agrobacterium tumefaciens* cells that carry a binary vector that constitutively expresses the gene silencing suppressor p19.

The protein coding sequence linked to the CMViva expression system may be any heterologous protein that is useful in optimizing plants for biofuel production, therapeutics, vaccines, diagnostics or the like. Heterologous proteins useful in the invention include proteins encoded by polynucleotides from any source, natural or synthetic. Suitable coding regions encode animal RNAs or polypeptides, as well as variants, fragments and derivatives thereof. The encoded products may be recovered for use outside the host plant cell (e.g., therapeutically active products) or utilized in-planta for modification of the plant biomass (e.g., cellulase production). Examples of such coding regions include polynucleotides derived from vertebrates, such as coding regions for RNAs (e.g., anti-sense RNAs, ribozymes, and chimeric RNAs having ribozyme structure and activity) or polypeptides (e.g. polypeptide coding regions). Other coding regions useful in the inventive methods are derived from other life forms such as yeast, fungi and bacteria. The heterologous proteins which find particular use in the invention include those that provide a therapeutic and/or diagnostic use in human and other animals. Such protein sequences are available in the literature and known to those of skill in the art.

d.) in Planta Production of Specific Enzymes Via the CMViva Expression System The CMViva expression system can be used to express various proteins of interest including enzymes involved catalyzing new biofuels as environmentally friendly alternatives. Such enzymes include enzymes involved in lignocellulosic degradation (e.g., low cost, scalable and energy efficient degradation of lignocellosic biomass) and enzymes used for oil bioconversion (e.g., conversion of feedstock triglycerides and free fatty acid).

A. In Planta Production of Enzymes Involved in Lignocellulosic Degradation

The invention provides a new system for controlled, in planta production of enzymes involved in lignocellulosic degradation using chemically inducible, transient, high level expression of cellulase enzymes produced in plants. There are several potential applications of this technology:

1. The rapid, high level expression of functional cellulase enzymes in the plant tissue just prior to harvesting (or just after harvesting the biomass), results in the degradation of lignocellulose, breakdown of plant tissues and generation of sugars. A "mash" of the plant biomass may be directly used as a feedstock for ethanol fermentation.

2. The system can be used as a screening platform for rapid production and evaluation of alternative and/or engineered cellulase enzymes and mixtures for different plants/substrates. One of the advantages of in planta screening is that plant tissues are comprised of the heterogenous, natural lignocellulosic material rather than an idealized laboratory substrate.

3. The system can be used for large scale production of enzymes to be used for degradation of nonviable or dried plant biomass (straws, woods, etc.), similarly to microbially derived enzymes but at a lower cost and reduced energy input.

One aspect of the invention provides expression systems for transient and stable production of recombinant proteins in plants and plant cell cultures. These can be used for rapid screening and production of cellulase enzymes in plant tissues. One embodiment of the invention provides for agroinfiltration of nontransgenic plant tissues with recombinant *Agrobacterium tumefaciens* containing the expression cassette for inducible, transient expression of cellulases. The invention encompasses chemically inducible expression systems such as the Cucumber mosaic virus inducible viral amplicon (CMViva) expression system. The system can be used in plant leaves, including *Nicotiana benthamiana* plant leaves for production of a heterologous protein. The CMViva system allows for the production of the recombinant protein upon the application of the chemical inducer, estradiol, to the plant leaf. In order to obtain a higher level and more controlled expression, the Cucumber mosaic virus (CMV) is engineered into the CMViva expressions system. CMV is a plant virus which has a wide host range among dicot and monocot plants, such that genes of interest can be inserted in place of the CMV gene which would normally encode the CMV capsid protein. The entire CMV genome is delivered to plant cells by agro-infiltration, transformation, or stable integration, and CMV replication and product production is subsequently induced by adding estradiol. During CMV replication the gene of interest is expressed at high levels due to gene amplification by CMV. As an added precaution, the CMV is engineered so that it does not move within plants beyond the point of infiltration, and so that it cannot move between plants. In one embodiment, a secretion signal peptide is used to target the recombinant protein to the apoplast. When the CMV coat protein replaced by AAT containing a secretion signal peptide, the presence of extracellular AAT can be verified in the transgenic CMViva plant cell suspension cultures following the addition of estradiol to the medium. Thus, the cellulases produced within the plant cells can be to the apoplast where they have a high degree of accessibility to the cell wall matrix which enhances their effectiveness.

The process for transient agroinfiltration is known in the art (see Sudarshana et al. (2006) *Plant Biotechnology Journal,* 4:551-559). A solution containing the recombinant *A. tumefaciens* can be applied to the leaf tissue through pressure injection using a sterile syringe (without a needle), and the estradiol solution is applied to the agroinfiltrated area about 12 hours later to induce expression. Maximum expression levels of recombinant protein (over 1% total soluble protein of functional recombinant AAT, a particularly unstable protein, was obtained) are observed about 2 day after induction. Some of the advantages of this method are:

- There is no need to generate or use transgenic plants.
- The co-infiltration with multiple recombinant *A. tumefaciens* can be used for simultaneous expression of different enzymes.
- There is a short production time—about 4 days total from frozen agro stock to protein production.
- There are minimal energy requirements (only for agrobacterial fermentation and plant tissue harvesting/processing).
- A variety of plant species can be used with the expression system.
- The systems allows for the rapid and easy screening of different enzymes by merely inserting the desired gene into the CMViva expression cassette and performing agroinfiltration on non-transgenic plants.

The invention further provides agroinfiltration processes that can be applied to freshly harvested plant tissues (see McDonald and VanderGheynst (2005) *Biotechnology Progress* 22:723-730) which provides advantages with respect to scale-up of the agroinfiltration and induction processes. For example, see FIGS. 23-26.

The process of stable transformation of plants using *agrobacterium* is well established. One aspect of the invention provides an inducible plant based expression system for the in planta production of known and novel cellulase genes. Plant-associated microbes, including endophytes, mutualists and a number of plant pathogens, encode for enzymes that allow the respective microbes to obtain nutrients from the associated plant, and as such are optimal sources of genes of interest. Most endophytes and mutualists survive in concert with the plant and therefore secrete enzymes that allow the microbe to obtain nutrients but do not disrupt plant health or fitness. In contrast, pathogens, by definition, cause disease in plants, but they also encode for enzymes that allow them to utilize plant components including lignin, cellulose, and pectin, as nutritional substrates. However, not all plant pathogens cause diseases that are similar in severity. Biotrophic plant pathogens are more generally dependent on a living host, and although they obtain nutrients by digesting plant parts, they regulate the quality and quantity of specific enzymes and do not generally destructively degrade and kill the host cell. By contrast, nectrotrophic plant pathogens are more "brute force" and often secrete greater quantity or quality of enzymes that can result in complete maceration and destruction of plant host tissues. Thus, plant-associated microbes offer a diverse and abundant source of enzymes that can be used to degrade plant components including cellulose. Due to rapidly accumulating genome information, the desired genes can be identified from GenBank and other public databases, can easily be isolated using standard PCR approaches, can be cloned (and codon optimized if desired), can be chemically synthesized and inserted into the CMViva expression cassettes for expression in plants. In one embodiment, the system can rapidly express different enzymes in plants via agroinfiltration. The proteins can be recovered from the infiltrated tissues and tested for activity on the desired substrates. This allows for rapid identification of useful enzymes, which can subsequently be produced in whole plants and if desired, then scaled-up to production in bioreactors.

B. In Planta Production of Enzymes Involved in Oil Bioconversion

The invention provides a new system for controlled, in planta production of enzymes involved as biocatalysts and/or chemical reaction steps for efficient production of bulk jet fuel surrogate and/or fuel additives from plant, yeast or algal oils (e.g., triglycerides). Such enzymes are involved, for example, into conversion of feedstock triglycerides and free fatty acids. Use of enzymes rather than chemical, thermal or inorganic catalytic methods has a number of advantages including higher specificity, milder conditions, lower energy input requirements, and reduced waste and minimal environmental impact since enzymes are biodegradable. For example, either chemical (acid-catalyzed or alkali-catalyzed) or enzymatic (lipase-catalyzed) approaches can be used for the transesterification of triglycerides to produce fatty acid methyl esters FAME (known as biodiesel). Use of lipase catalyzed transesterification has a number of advantages over alkali-catalyzed transesterification, including lower energy requirements (the lipase process reaction temperature is 30-40° C. while the alkali process is 60-70° C.); easier recovery of free glycerol; insensitivity to water content in feedstock oil (for the alkali-catalyzed process the oils must be anhydrous because water results in saponification, producing soap, which reduces catalytic efficiency and alters the physical properties of the product); the ability to convert free fatty acids in the feedstock to FAME; and no more need for alkali wastewater treatment. A wide variety of lipases have been identified, characterized, produced in recombinant systems, and produced commercially for a variety of industrial applications. With the advent of genetic engineering approaches it is possible to tailor an enzyme's catalytic ability through approaches such as directed molecular evolution, thereby opening up new routes for enzyme engineering in order to enhance specificity, stability and catalytic efficiency under process conditions. The main drawback to the biocatalytic route is the high cost associated with the manufacturing and purification of the enzymes, including the difficulty in re-using them due to their inherent instability. The invention offers a novel and much less costly approach, namely to produce the required enzymes directly in plant leaves via the CMViva expression system.

Examples of lipases which break down storage triglycerides into fatty acids are fatty acyl-CoA reductase (FAR) which converts fatty acids to fatty aldehydes and fatty aldehyde decarbonlyase (FAD) which converts the fatty aldehyde to a shorter (one carbon less) alkane/alkene and liberates carbon monoxide. Many lipases have been identified, characterized, produced in recombinant systems, and produced commercially for a variety of industrial applications (see Hasan et al., 2006).

Once the target enzyme for the bioconversion process has been identified, the enzyme can be expressed using the procedures described herein and produced by procedures well know in the art.

EXAMPLES

The following specific examples are intended to illustrate the invention and should not be construed as limiting the scope of the claims.

Example 1: Construction of the CMViva Expression System 1

The following materials were used in this example:

The complete cDNA clones, pQCD1, pQCD2, and pQCD3, corresponding to genomic RNAs 1, 2 and 3, of CMV strain Q (Ding et al., 1995), respectively.

The binary plasmid vectors pER8 (Zuo et al., 2000) and pER10 containing the estradiol inducible expression system (XVE system); plasmid pER10 is similar to pER8 except it contains nptII as the selectable marker instead of the hygromycin resistance gene.

The binary vector p35S:p19 (Voinnet et al., 2003) containing the TBSV p19 gene

The binary vectors pDU97.1005 (Uratsu and Dandekar, unpublished), a modified version of pCGN1547 (McBride and Summerfelt, 1990)), pDU99.2215 (Escobar et al., 2001) and pART7 (Gleave, 1992).

A. tumefaciens strain EHA105:pCH32 (Hamilton, 1997) was used to carry all the binary vectors used in this study except for p35S:p19, where A. tumefaciens strain C58C1 was used.

Figure 1B:
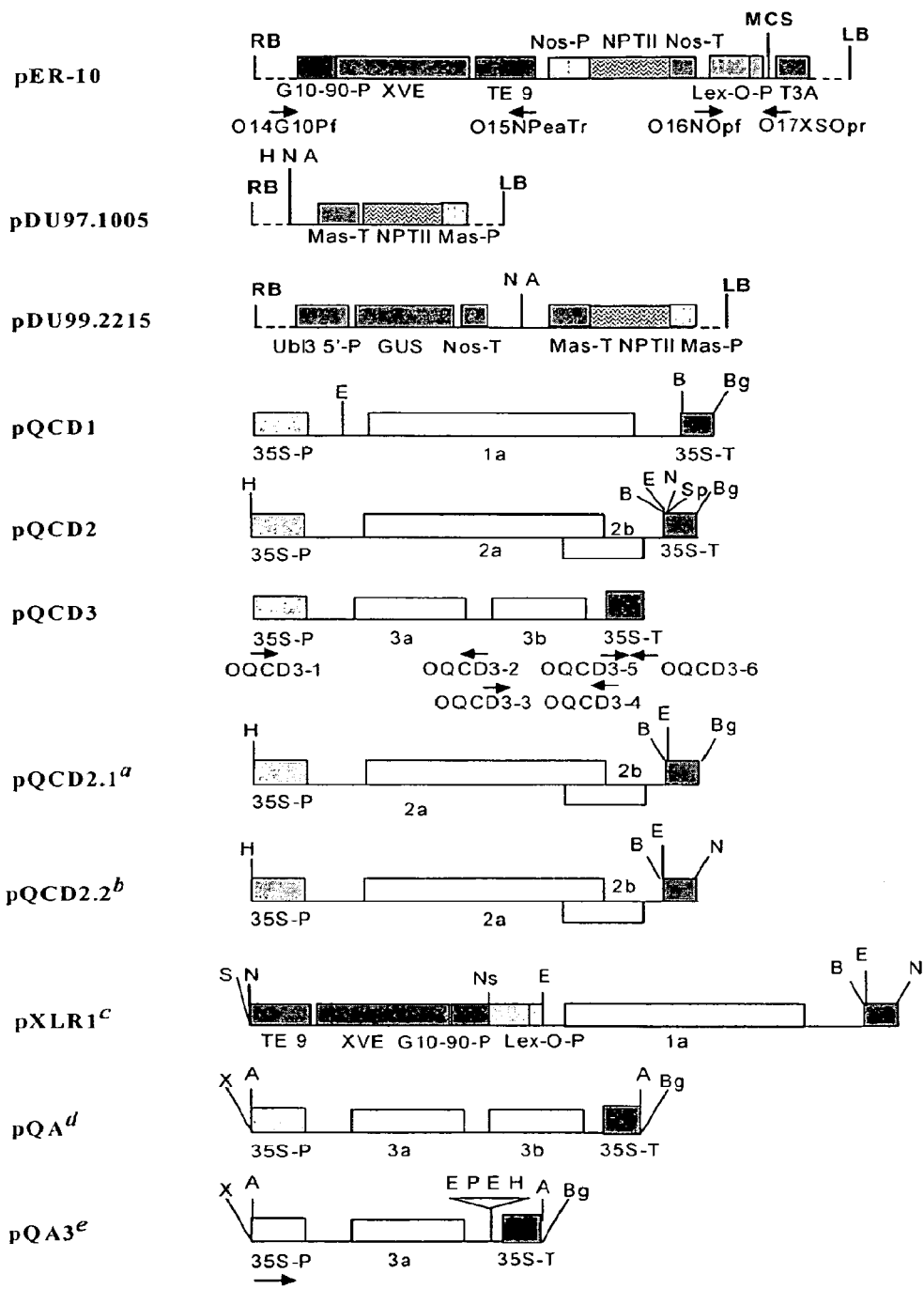
Figure 2:
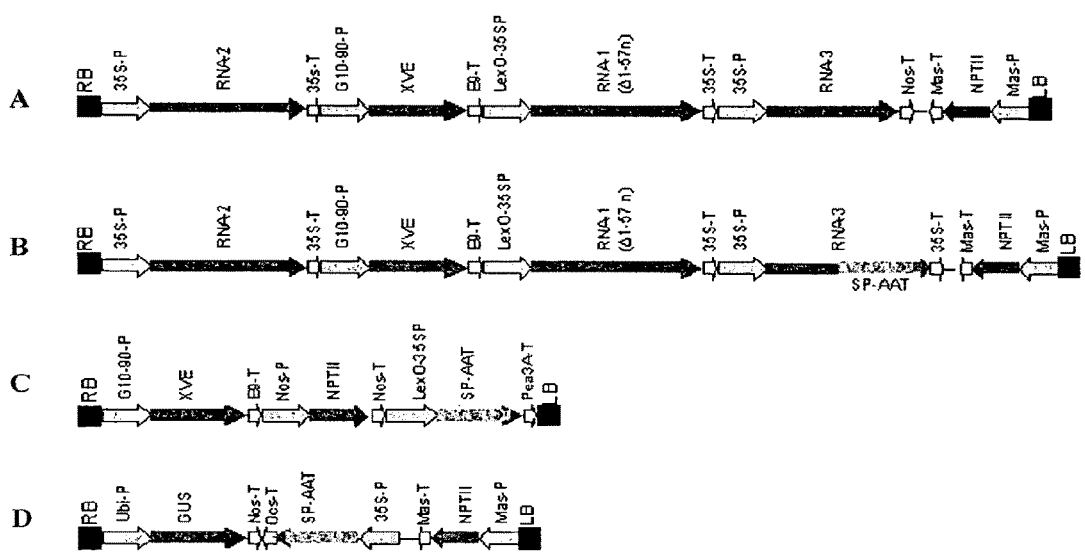

A series of binary plasmids were constructed to give inducible protein expression in plants after agroinfiltration (FIG. 2). The plasmid pCMV was constructed by inserting a Hind III/Not I fragment from pQCD2.2, a Not I fragment from pXLRN1, and an Asc I fragment from pQA, sequentially, into pDU97.1005 (see FIG. 1B and Table 1 below for linear maps of parental and intermediate plasmids and primers used). For pCMV-SPAAT, a plant codon-optimized gene encoding for the AAT gene containing a signal peptide (SP) sequence from rice α-amylase (SPAAT) (courtesy of Ventria Biosciences, West Sacramento, Calif.) was amplified using primers OSDAATPst and OSDAATCPst, digested with Pst I and ligated with pQA3 linearized with Pst I. From the resultant clone an Asc I fragment was used to construct pCMV-SPAAT as described for pCMV. The plasmid pCMV contained all three CMV genomic components. The regions coding for CMV RNAs 2 and 3 were controlled by the Cauliflower mosaic virus (CaMV) 35S promoter as in the original plasmids, (pQCD2 and pQCD3) but the gene for CMV RNA 1 was modified to be under control of the estradiol-activated LEX operator. The plasmid pCMV-SPAAT was similar to pCMV, except that the CMV coat protein (CP) gene (on the RNA 3 segment) was replaced with SPAAT. The plasmid pXVE-SPAAT was constructed by inserting the SPAAT sequence into pER10 so that SPAAT was under control of the LEX operator. Finally, p35S-SPAAT was constructed by inserting SPAAT next to 35S promoter in pART7 and transferring a Not I fragment into pDU99.2215.

Example 2: Construction of the CMViva Expression System 2

Whereas the CMViva expression system in Example 1 is a binary pCMV-SPAAT plasmid (FIG. 2B), CMViva expression system can also be two separate binary plasmids. The first binary plasmid is the pDUR22XLR1R (FIG. 27); the second binary plasmid is comprised of a series of ten plasmids containing the AscI fragment for pQA (FIG. 28)

cloned into pDU97 giving plasmids pQA-2, pQA-4, pQA-6, pQA-7, pQA-8, pQA-9, pQA-10, pQA-11, pQA-12, and pQA-13, collectively called the pQA series hereafter. The pQA series is modified to have restriction sites including, but not limited to, Eco RI-Sac, I-Kpn, I-Sma, I-BamHI-Xba, I-Acc, I-Sal, I-Pst, and I-Sphl-Hind III. The heterologous gene is cloned into the multiple cloning site (MCS) of one or all of the pQA series of plasmids. The different restriction sites used for cloning the recombinant genes allow for easier and more efficient cloning and expression of the heterologous genes, as well as for the identification of optimal sequences for protein expression.

The first and second binary plasmids are separately transformed into A. tumefaciens cells. Following transformation, equal amounts of each type of recombinant A. tumefaciens cells are co-infiltrated or introduced into N. benthamiana leaves.

The pDUR22XLR1R expression system is tightly regulated and chemically induced by estradiol. Upon application of estradiol, RNAs 1 and 2 of pDUR22XLR1R expresses the replicase genes. The expression of RNA 1 and RNA 2 leads to the replication of the recombinant gene in the RNA 3 deriving from the second binary plasmid comprising of the pQA series.

Example 3: Agroinfiltration and Induction of Transactivation

A. tumefaciens EHA105:pCH32 cells containing the appropriate plasmids were grown for 24 to 48 hours in 2 ml LB broth. Approximately 0.5 ml was then transferred to 25 ml LB medium supplemented with 10 µl of 100 mM acetosyringone (3', 5'-dimethoxy-4'-hydroxyacetophenone) (Aldrich Chemicals, Milwaukee, Wis.) and 0.5 ml of MES buffer (pH 5.6) and grown overnight at 28° C. with shaking until cell density ($OD_{600}$) reached 1.0 absorbance units. Cells were harvested by centrifuging at 2600 g, resuspended in 10 ml sterile de-ionized water, and cell density was adjusted to 1.0 absorbance units. Five ml of the A. tumefaciens cell suspension for each plasmid (p35S-SPAAT, pXVE-SPAAT, and pCMV-SPAAT) was separately mixed with either five ml of sterile water or A. tumefaciens cells containing the p35S:p19 plasmid, then supplemented with magnesium chloride to reach a final concentration of 10 mM and acetosyringone to 150 µM and incubated at room temperature for three hours. Bacterial suspensions were then pressure infiltrated onto the abaxial side of young N. benthamiana leaves using a three ml sterile syringe without a needle at 1-2 points to sufficiently cover at least half of the leaf (for information see the world wide web at www.jic.bb-src.ac.uk/sainsbury-lab/dcb/services/agroInfil1.mpg).

About 12 hours after infiltration, a 50 µM solution of 17-β-estradiol (Sigma Inc., St. Louis, Mo.) in 0.05% Tween 20 was applied using cotton tipped applicators to both sides of infiltrated N. benthamiana leaves. No solution was applied to plants to be used as non-induced (control) as well as the p35S-SPAAT-infiltrated and healthy control plants.

Example 4: Protein Extraction, Quantification and Immunoblot Analysis of Expressed Proteins Plant leaves were sampled on the infiltrated area 2.5 days (60±1 hrs) post-infiltration by collecting four one cm diameter discs per leaf. Extraction buffer composed of 20 mM Tris-HCl (pH 8.1), 150 mM NaCl and 0.01% (vol/vol) Tween 80 was added at 10 µl per mg fresh weight of tissue, and cells were lysed on ice using a plastic pestle. Lysate was cleared by centrifugation at 20,000 g for 20 min at 4° C. The supernatant was collected and stored on ice briefly until assayed. Total soluble protein concentrations were determined by the Bradford protein assay (BioRad, Hercules, Calif.) using bovine serum albumin (BSA) (Fisher, Pittsburgh, Pa.) as the standard.

Example 5: Immunoblot Analysis

Proteins were denatured by boiling 40 µl supernatant samples for five minutes in 10 µl sodium dodecyl sulfate (SDS) sample buffer resulting in a final buffer concentration of 0.4% (vol/vol) SDS, 62.5 mM Tris-HCl (pH 8.2), 10% glycerol, 5 mM EDTA and 0.01% (wt/vol) bromophenol blue. A 15 µl aliquot of each denatured sample was fractionated by sodium dodecyl sulfate-polyacrylamide gel electrophoresis (SDS-PAGE) on 12% Tris-HCl precast gels (BioRad) carried out in a Mini-PROTEAN 3 electrophoresis cell (BioRad) for 35 min at 200 V. Proteins were then blotted onto 0.45 µm nitrocellulose membranes (GE Osmonics, Minnetonka, Minn.) for 85 min at 120 V using an electroblot Mini Trans-Blot transfer cell (BioRad). Immunoblot analysis was then performed according to the procedure described elsewhere (Huang et al., 2001) with the only alteration being the vendor of the secondary antibody used in this study (Southern Biotechnology, Birmingham, Ala.). Chemiluminescence detection was used for the CMV CP immunoblot. Human AAT (Calbiochem, La Jolla, Calif.) was used as the standard for all assays performed.

Example 6: Band Shift Assay

Formation of a covalent complex between AAT and porcine pancreatic elastase (PPE) (Wilczynska et al., 1997) was examined by visual inspection of functional AAT by immunoblot analysis. Briefly, 2 µl of either supernatant sample or human AAT standard (3.1 pmol AAT) was added to 2 µl (100 pmol) of PPE (Calbiochem) in 36 µl extraction buffer and incubated for 20 min at 37° C. The complex was then analyzed using the same immunoblot analysis previously described.

Example 7: Quantification of Total Recombinant AAT by ELISA

Rabbit anti-human $\alpha_1$-antitrypsin polyclonal IgG fraction was diluted 1:4,000 in phosphate buffer saline (PBS; 137 mM NaCl, 2.7 mM KCl, 10.1 mM $Na_2HPO_4$ and 1.8 mM $KH_2PO_4$, pH 7.4) was used to coat ELISA plates overnight (Corning, Corning, N.Y.). The wells were then blocked using 200 µl of 0.1% (wt/vol) BSA in PBS and washed with PBS containing 0.05% (vol/vol) Tween 20 (PBST). Supernatant samples were diluted in PBST and 50 µl was added per well and incubated for one hour at 25° C. Human $\alpha_1$-antitrypsin, diluted in PBST to concentrations from 800 ng/ml to 0.78 ng/ml by two-fold dilutions, was used to generate the standard curve. After washing, 50 µl of horseradish peroxidase-conjugated polyclonal goat anti-human $\alpha_1$-antitrypsin IgG (HRP) (US Biological, Swampscott, Mass.) diluted 1:4,000 in PBS was added to the wells and incubated for one hour. The wells were washed and 100 µl of SureBlue peroxidase substrate solution (KPL, Gaithersburg, Md.) was incubated for 25 min. The reaction was stopped by the addition of 100 µl of HCl (1 M) and the absorbance at 450 nm was measured with a SpectraMax 340pc microplate reader (Molecular Devices, Sunnyvale, Calif.).

Example 8: Quantification of Functional Recombinant AAT

Using the principle of the band shift assay, 100 µl of PPE diluted 1:1,500 in PBST was added in excess to 100 µl of either supernatant extract sample or human AAT standard (again diluted from 800 ng/ml to 0.78 ng/ml) and incubated for 20 min at 37° C. to allow formation of the AAT-PPE complex. The same ELISA protocol was used as for total rAAT detection except that polyclonal rabbit anti-elastase IgG conjugated to HRP diluted 1:30,000 in PBS was used as the secondary antibody to allow specific detection of the AAT-PPE complex. This allowed quantification of the amount of functional recombinant AAT.

Example 9: CMViva Protein Expression in Plants

Figure 3:
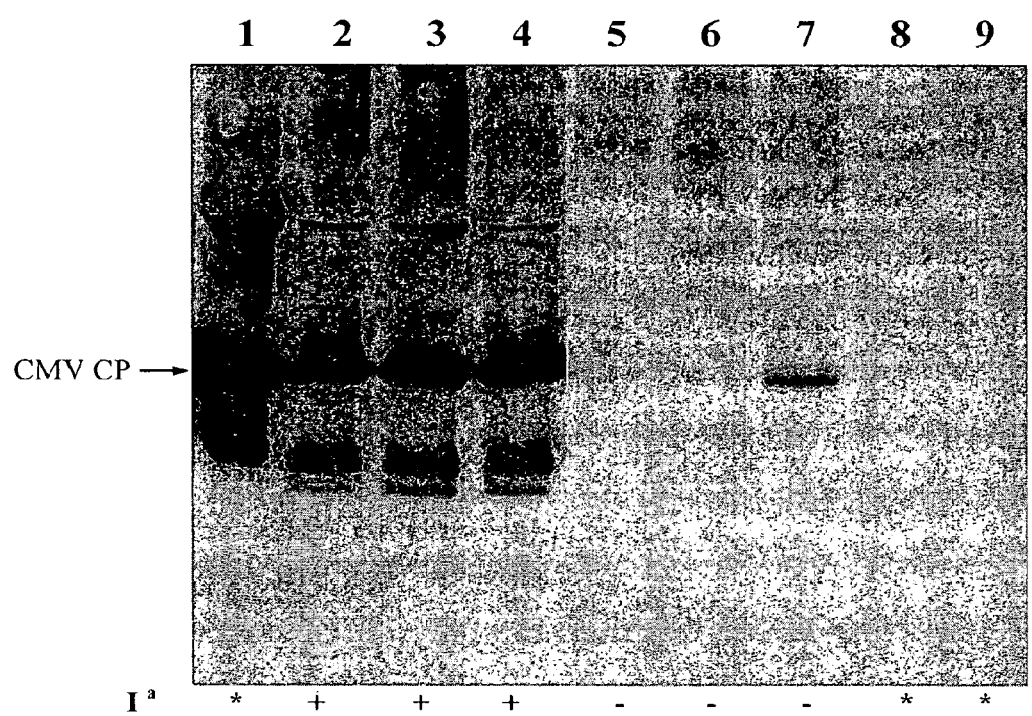

It was first determined if it is possible to obtain high levels of protein expression via agroinfiltration of non-transgenic plants with the CMViva expression system using plasmid construct pCMV (FIG. 2), and if the protein expression could be controlled. The results showed that CMViva gave very high expression of the native CMV CP after induction by adding estradiol (FIG. 3). By using the sensitive chemiluminescence assay at saturation conditions it was possible to investigate if the expression of the CMV CP was tightly controlled. The data showed that CMViva-driven expression of CMV CP was slightly leaky as low levels of CP were seen in plants in almost all experiments (FIG. 3, lane 7). However, upon induction with estradiol very high levels of CMV CP were detected. In fact when compared on a wt:wt basis, similar levels of CMV CP were seen in CMViva-expressing N. benthamiana leaf tissues (FIG. 3, lanes 2-4) and CMV-infected Cucurbita pepo plants (FIG. 3, lane 1), a natural host for the CMV strain used herein.

The next experiment focused on whether one could use the CMViva system to express desirable proteins in non-transgenic plants. The human therapeutic protein AAT was chosen to further investigate this. The qualitative and quantitative results were clear and dramatic. A comparison focused on transient expression of rAAT in N. benthamiana leaves at 2.5 days post-infiltration using the CaMV 35S promoter (p35S-SPAAT), estradiol-driven Lex operator system (pXVE-SPAAT), and the CMViva system (pCMV-SPAAT). To achieve enhanced expression, the three systems were evaluated when co-infiltrated with A. tumefaciens containing the known gene silencing suppressor p19 (Voinnet et al., 2003). CMViva and pXVE-SPAAT were evaluated both with and without estradiol treatment to assess the ability to regulate protein expression.

Figure 4:
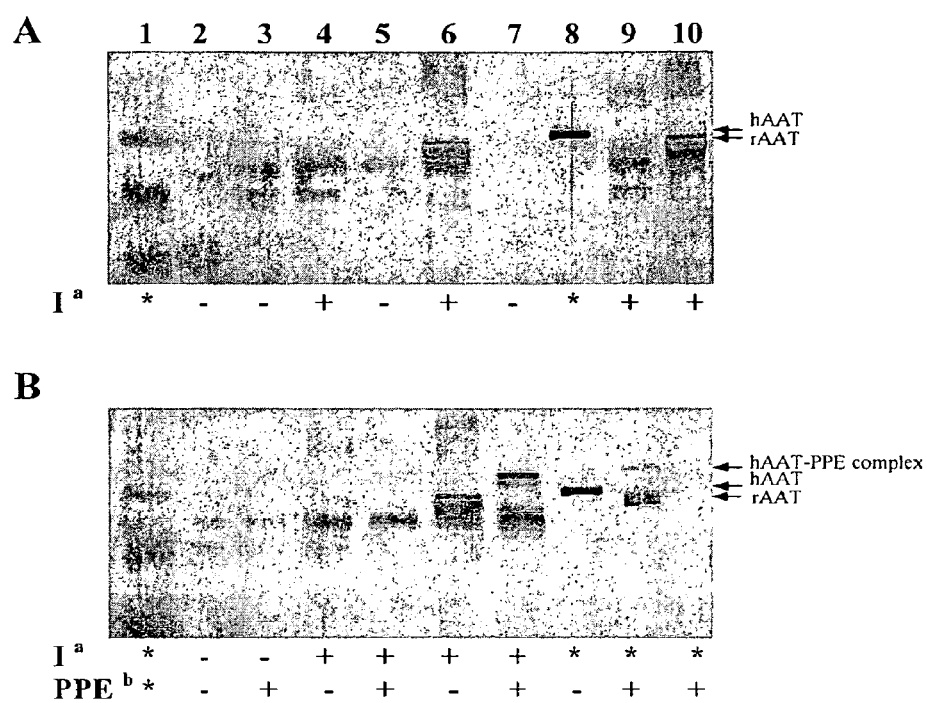

Immunoblot analysis showed that all three systems gave detectable rAAT accumulation. rAAT expression via pXVE-SPAAT appeared to be slightly leaky (FIG. 4A, lane 5) while higher levels of rAAT were detected upon induction with estradiol (FIG. 4A, lanes 4 and 9). CMViva expression of rAAT was greater than that for pXVE-SPAAT (FIG. 4A, lanes 6 and 10 compared with lanes 4 and 9), and appeared to be more tightly regulated since very little rAAT was detected before addition of estradiol (lane 7), while high levels of rAAT were seen after adding estradiol (lanes 6 and 10). It should be noted that in this experiments the CMViva-produced rAAT seen in the immunoblots (FIG. 4A, lane 6) exhibited a slightly faster migration in SDS-PAGE than did human AAT used as a control (FIG. 4A, lane 8). The rAAT produced in these studies had a lower molecular weight than authentic human AAT. This has been observed in other plant-based expression systems, and has further been attributed to a number of possible reasons including, lacking a portion of the C-terminal end of rAAT (Terashima et al., 1999), expression of different forms of rAAT (Huang et al., 2001; Terashima et al., 1999), and/or differences in glycosylation patterns (Trexler et al., 2002). Therefore, in order to determine if the CMViva-produced rAAT exhibited functional characteristics like the human AAT control, both of their abilities to bind to porcine pancreatic elastase (PPE) were compared. When AAT was incubated with PPE, followed by SDS-PAGE and immunoblot analysis, AAT bound with PPE exhibited a slower migration (band shift). FIG. 4B presents results of this analysis and shows that CMViva-expressed rAAT resulted in a band shift as did the human AAT control (see lanes 7 and 9), and it also suggested that the PPE-bound CMViva-expressed rAAT provides a high percentage of the total.

Example 10: Effect of the Gene Silencing Suppressor p19

Figure 5:
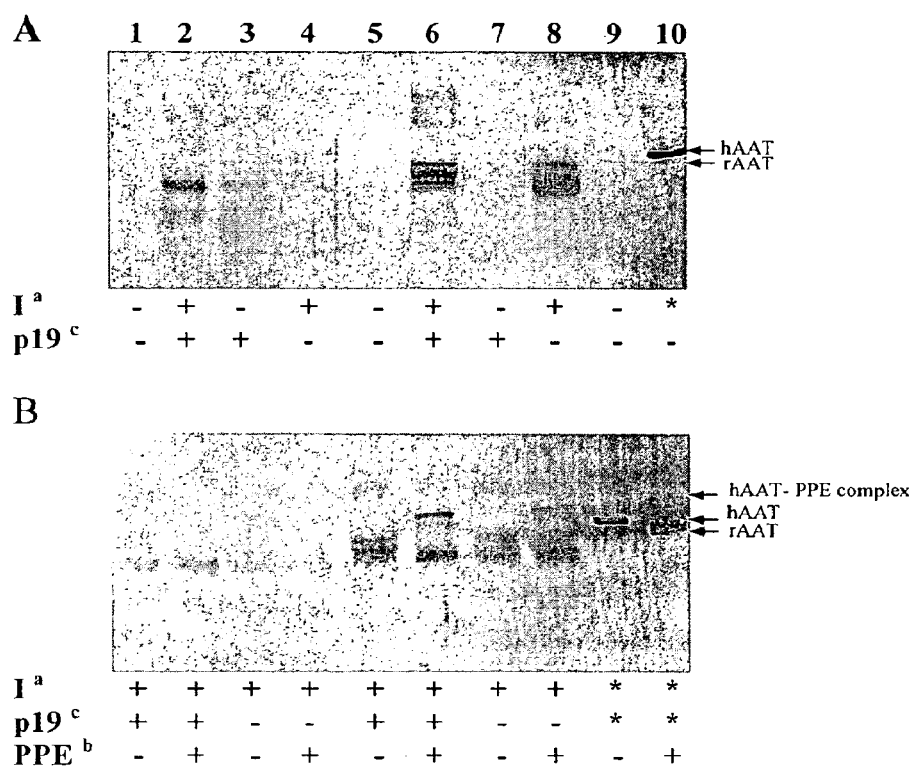

The next assessment focused on whether co-infiltration with A. tumefaciens containing the gene silencing suppressor p19 enhanced the rAAT production. It is known that agroinfiltration and CaMV-driven transient protein production in nontransgenic plants can be enhanced if plant virus-encoded gene silencing suppressor proteins (SSPs) are used to block post-transcriptional gene silencing (PTGS) in the infiltrated leaves. PTGS is a plant response resulting in degradation of specific RNAs, and many plant virus-encoded proteins have been shown to have the ability to block PTGS. Therefore, the effect of p19 by co-infiltrating A. tumefaciens cells containing either p35S-SPAAT, pXVE-SPAAT or pCMV-SPAAT and A. tumefaciens cells containing either p35S:p19 or sterile water into N. benthamiana leaves were evaluated and the respective rAAT production was compared. Co-infiltration with p35S:p19 resulted in higher rAAT levels for pXVE-SPAAT even when no estradiol inducer was added (FIG. 5A, lane 3 vs. lane 5) while more rAAT was seen for treatments receiving both p19 and inducer (lane 2). More CMViva-produced rAAT was also achieved when using p19 (FIG. 5A, lane 6 vs. lane 8). Here, CMViva production of rAAT was neither increased when leaves were treated with p19 nor with estradiol inducer (FIG. 5A, lane 7). The ability of CMViva-expressed rAAT to bind PPE was also evaluated. Treatments that included p19 and induction with estradiol showed the most rAAT bound with PPE (FIG. 5B). Thus, CMViva in combination with the p19 SSP resulted in the highest levels of functional rAAT (as assessed by binding with PPE).

Example 11: Quantification of Total and Functional rAAT

Figure 6:
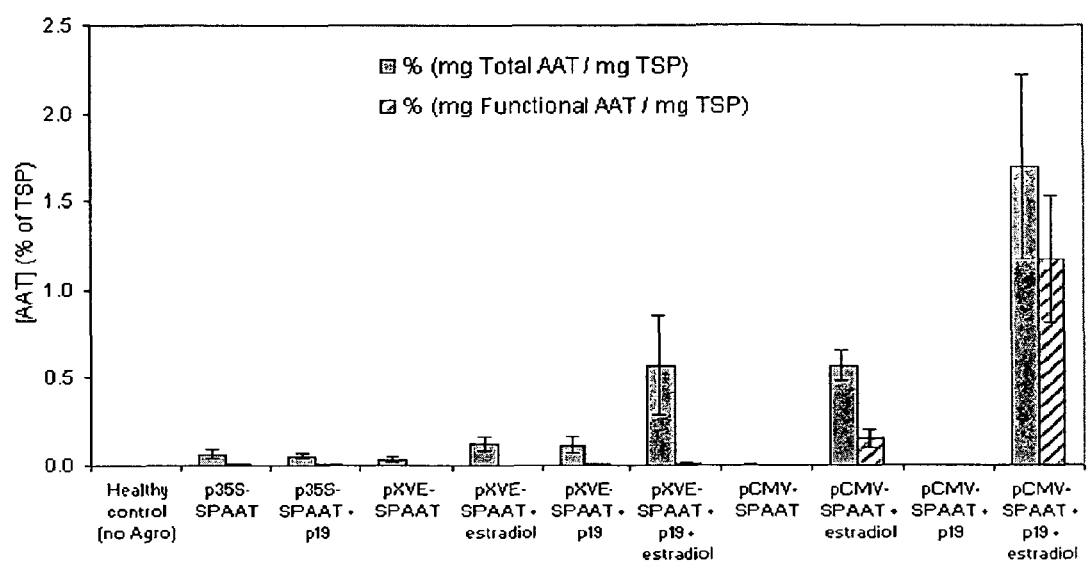

In order to take a more quantitative approach, ELISA was used to determine total and functional rAAT in agroinfiltrated N. benthamiana leaf samples containing each of the three expression vectors. The pXVE-SPAAT and pCMV-SPAAT systems were analyzed both with and without estradiol induction while all three systems were analyzed with and without p19. The total soluble protein (TSP) concentrations were measured and production of rAAT was expressed in terms of a percentage of the TSP concentration for each sample (FIG. 6).

Use of the constitutive CaMV 35S promoter alone resulted in transient production of total rAAT at 0.06±0.03% TSP and this level did not significantly change even with p19, which resulted in 0.05±0.01% TSP. The pXVE-SPAAT system showed detectable rAAT levels even without addition of the estradiol inducer, resulting in total rAAT at 0.03±0.02% TSP without p19 and 0.12±0.05% TSP with p19. Induction of the pXVE-SPAAT system increased total rAAT production, leading to 0.12±0.04% TSP and 0.57±0.28% TSP without and with p19, respectively. The CMViva expression system was tightly controlled when not induced, resulting in an undetectable level of total rAAT both without and with p19. The CMViva expression system with induction gave the highest levels of total rAAT, resulting in rAAT at 0.57±0.09% TSP without p19, a level similar to pXVE-SPAAT with p19, and increased to 1.7±0.53% TSP with p19.

Quantification of functional rAAT was also measured by ELISA and represented in terms of a percentage of the TSP concentration. The CaMV 35S promoter resulted in only small amounts of functional rAAT, at 0.006±0.001% TSP without p19 and 0.007±0.001% TSP with p19. Just as for the total rAAT, the pXVE-SPAAT system produced minimal functional rAAT even without addition of the estradiol inducer, resulting in functional rAAT without and with p19 at 0.0013±0.0006% TSP and 0.0089±0.0010% TSP, respectively. Induction of the pXVE-SPAAT resulted in no detectable functional rAAT in the absence of p19 and 0.013±0.003% TSP in the presence of p19. Induction of the CMViva expression system resulted in the highest production of functional rAAT at 0.16±0.048% TSP without p19 and 1.2±0.36% TSP with p19. Thus 70±3.3% of the total rAAT produced using the CMViva expression system in combination with the p19 SSP was in the functional form.

As can be seen in the examples above, the invention encompasses an efficiently regulated plant virus amplicon expression system (here referred to as CMViva) for transient expression of proteins in plants. Furthermore, the usefulness of CMViva was demonstrated by qualitative and quantitative analysis of a CMViva-produced human therapeutic protein, AAT. The CMViva expression system described here is conceptually similar to the system described by Mori et al., (2001) but differs in several key aspects, resulting in important and distinct advantages (FIG. 1A). Firstly, the use of the estradiol-inducible XVE system (Zuo et al., 2000) provides a distinct advantage. XVE is a 3-component fusion protein comprised of a DNA binding moiety (bacterial repressor LexA (X)), a transactivating domain VP16 (V) and the regulatory region of the human estrogen receptor (E), which functions as transcription activator. Using this system, Zuo et al., (2000) observed an eight-fold increase in GFP expression in transgenic Arabidopsis plants upon application of estradiol when compared to GFP expression using a constitutive CaMV 35S promoter system, and no detectable GFP transcripts under non-induced conditions. The XVE system is more tightly regulated with minimal "leakage" in the absence of inducer, estradiol has no deleterious physiological effects on plants (as has been observed with DEX), and estradiol is more soluble than DEX in aqueous solutions. In the experiments described herein, however, XVE-driven rAAT was slightly leaky suggesting that the XVE system alone was not suitable for providing controlled expression of desired proteins such as AAT. Secondly, we used CMV, rather than BMV (as used by Mori et al., (2001)). Like for BMV, the CMV genome is composed of three positive-sense, single-stranded RNAs. All three genomic components (RNA 1, RNA 2 and RNA 3) are required for a competent infection, but unlike BMV, CMV encodes for the potent silencing suppressor protein 2b. CMV RNA 2 encodes for the 2b protein, but 2b is expressed from the 2b subgenomic RNA (sgRNA) which is derived from RNA 2 only after RNA replication, which occurs here upon addition of the estradiol inducer. Thirdly, the invention encompasses modification of the 5' sequence of the CMV 1a cDNA so that positive sense 1a RNA will not be replicated in the presence of functional replicase, as would normally occur in wild type CMV. Fourthly, all three CMV components were engineered on a single Ti plasmid in A. tumefaciens, thereby significantly decreasing the amount of time that would normally be required to generate and cross transgenic lines containing each component separately in order to obtain stably transformed transgenic plants. Finally, the use of the CMViva expression system as a transient production method using wild type N. benthamiana plants was demonstrated herein. This is particularly significant since it allows for rapid construct design, as well as rapid, efficient protein production in non-transgenic plants.

It was found that while p19 had no effect on enhancing rAAT levels when using p35S-SPAAT, co-infiltration with p19 significantly improved total rAAT production in both the induced XVE and CMViva systems. In the CMViva system, the impact of p19 was a three-fold increase in total rAAT production, while in the XVE system a five-fold effect was observed. The effect of p19 was even more profound on the production of functional rAAT resulting in an eight- and sixteen-fold increase for CMViva and XVE, respectively. The presence of p19 also increased the percentage of functional rAAT relative to the total rAAT level, resulting in a maximum of 70±3.3% in this study. Notably, p19 addition enhanced rAAT expression even though the CMViva was designed to encode the CMV 2b silencing suppressor.

Thus, the experiments have shown that the CMViva system provides the ability to tightly control the timing of gene expression and resulting protein production even in non-transgenic plants. CMViva resulted in rAAT production which was 30 to 170-times greater than that obtained using the constitutive CaMV 35S promoter for total and functional target protein. The experiments have also shows that the CMViva amplicon system provides new opportunities for producing biologically active mammalian proteins in plants, and can even overcome some of the common problems seen when using stably transformed plants.

The CMViva expression system may further be evaluated in transgenic cell cultures in order to develop a CMViva based production platform that will facilitate large-scale estradiol treatment for induction and easier recovery of recombinant proteins secreted into the medium.

Example 12: CMViva is an Efficient Plant Expression System

As shown above, the novel Cucumber mosaic virus (CMV) inducible viral amplicon (CMViva) expression system allows for tightly regulated chemically-inducible expression of heterologous genes in plant hosts. Transient production of recombinant $\alpha_1$-antitrypsin (rAAT), a human blood protein, was shown in *Nicotiana benthamiana* leaves. The highest production levels were obtained by co-infiltrating leaves with *Agrobacterium tumefaciens* cells containing CMViva carrying the AAT gene and *A. tumefaciens* cells carrying a binary vector constitutively expressing the gene silencing suppressor p19. Accumulation of up to thirty-fold more rAAT was observed in leaves (24 mg per 100 g leaf tissue) when compared with the expression levels observed using the CaMV 35S promoter. Significantly, 70% of the rAAT produced using the CMViva expression system was found to be biologically active, a 170-fold increase in functional protein compared with the CaMV 35S expression system.

Example 13: Production of Functional Recombinant Human Protein in Transgenic Tobacco Cell Cultures: Comparison of Gene Expression Systems Three different types of expression systems, (1) the constitutive p35S, (2) the chemically inducible XVE, and (3) the chemically inducible viral amplicon CMViva, were compared for the production of human therapeutic protein coded by the same transgene in transgenic *N. benthamiana* cell cultures in bioreactors. The following example provides the use of the chemically inducible XVE promoter system and the chemically inducible viral amplicon CMViva expression system in stably transformed plant cell cultures for human protein expression.

Construction of the p35S-spAAT (35S), pXVE-spAAT (XVE) and pCMV-spAAT (CMViva) expression vectors is described in Example 1. The codon usage of the human AAT gene sequence was optimized according to the codon preference of rice cell host (*Oryza sativa*). The three expression systems were stably transformed into *Nicotiana benthamiana* cells using *Agrobacterium*-mediated transformation by the *Agrobacterium tumefaciens* strain EHA105 pCH32 (Hamilton 1997) carrying appropriate binary vectors. Newly expanded leaves from *N. benthamiana* plants were cut into 1 cm square sections soaked in an *Agrobacterium* solution adjusted to 0.1 OD 600 for 10 minutes and incubated on co-cultivation medium consisting of Murashige and Skoog minimal organics (MSO) medium modified with 30 g/L sucrose, 2 mg/L 6-benzylaminopurine (BA), and 200 µM acetosyringone, pH 5.8, at 23° C. in the dark for 2~3 days. Leaves were transferred to agar-solidified induction medium consisting of MSO medium modified with 30 g/L sucrose, 2 mg/L BA, 400 mg/L carbenicillin, 250 mg/L cefotaxime, and 250 mg/L kanamycin and incubated at 26° C. for 10 days. Plant tissues were subcultured until shoots formed. Shoots were harvested and transferred to agar-solidified rooting medium consisting of half strength MSO medium modified with 15 g/L sucrose, 2 mg/L BA, 1.3 g/L calcium gluconate, 400 mg/L carbenicillin, 250 mg/L cefotaxime, and 100 mg/L kanamycin. Leaves were removed from each rooted shoot with a portion of the petiole attached and placed on callus-generating medium consisting of MSO medium modified with 30 g/L sucrose, 0.4 mg/L 2,4-dichlorophenoxyacetic acid (2,4-D), 0.1 mg/L kinetin, 400 mg/L carbenicillin, 150 mg/L timentin, and 100 mg/L kanamycin for developing transgenic callus. Transgenic callus was subcultured every 3-4 weeks and maintained on agar-solidified KCMS medium consisting of 30 g/L sucrose, 4.3 g/L MS salt mixture, 0.1 g/L myo-inositol, 0.204 g/L KH2PO4, 0.5 mg/L nicotinic acid, 0.5 mg/L thiamine-HCl, 0.5 mg/L pyridoxine-HCl, 0.2 mg/L 2,4-D, 0.1 mg/L kinetin, and 100 mg/L kanamycin, pH 5.8. Heterologous gene silencing suppressors were not incorporated into or applied to any of systems.

Transgenic *N. benthamiana* cell lines were maintained in liquid KCMS medium containing 100 mg/L kanamycin, pH 5.8. Transgenic *N. benthamiana* cell suspensions were maintained in 250 mL flasks on an orbital shaker at 140 rpm and 25-26° C. under ambient light and subcultured weekly by transferring 10 mL into 90 mL fresh KCMS medium.

The inducer, 17-beta-estradiol, dissolved in DMSO, was added to cultures of XVE and CMViva transgenic cell lines at a specific time after inoculation to start induction. The final concentration of DMSO was not higher than 0.3%.

A BioFlo 3000 bioreactor (New Brunswick Scientific) with a single pitched blade impeller containing 3.5 L KCMS medium was autoclaved. Inoculum cultures grown in 250 mL KCMS medium in 1 L Erlenmeyer flasks on an orbital shaker at 140 rpm, 25° C., for 7 days were combined to inoculate the bioreactor at a 10% density (volume of inoculating suspension to final volume). The bioreactor was maintained at 25° C., 50-75 rpm, and 40% (air saturation) dissolved oxygen under ambient light. The dissolved oxygen concentration was controlled by manipulating the oxygen concentration in the gas sparging stream. Gas was introduced through a spherical gas diffusion stone with a pore size of 20 µm positioned at the bottom of the bioreactor. The aeration rate was regulated as necessary (0.4-1.0 L/min) for dissolved oxygen control. Oxygen uptake was monitored by measuring the change in dissolved oxygen in the absence of aeration. The pH was recorded on-line as well as off-line for verification. At each sampling time, culture samples were collected, placed in 1.5 mL microfuge tubes, and centrifuged at 14,000 rpm for 10 min at 4° C. The supernatant was stored at −80° C. for later analysis.

Fresh cell weight (FCW) was measured by filtering 10 mL culture onto a predried, preweighed, Whatman #1 filter connected to a vacuum, washing the cells with 20 mL ddH2O to remove residual sugars, then weighing the cells. Dry cell weight (DCW) was estimated after drying the retained cells at 60° C. for 2 days.

An immunoassay based on competitive binding was developed for quantitative determination of estradiol in culture medium. Mouse anti-estradiol-6-carboxy methyloxine (6-CMO)-bovine serum albumin (BSA) monoclonal immunoglobulin G (IgG), the capture antibody, was diluted 1:4,000 in phosphate-buffered saline (PBS), and ELISA plates were coated with it overnight at 4° C. The plates were washed with PBS containing 0.05% (v/v) Tween 20 (PBST) before loading samples and standards. Estradiol standards at different concentrations (0 to 8000 pg/mL) and samples diluted in PBST were placed in wells. Horseradish peroxidase-conjugated estradiol, diluted 1:500 in PBST, was dispensed to each well and the plate was incubated at room temperature for 2 hours. SureBlue peroxidase substrate solution was added and incubated for 30 min. The enzyme reaction was terminated by addition of 1 N HCl, and absorbance at 450 nm was measured and recorded with a SpectraMax 340PC microplate reader.

Protease activity was quantified by a modification of a published procedure (Joo et al. 2006). Substrate solution (0.3 mL) containing 10 mg/mL casein sodium in 50 mM phosphate buffer (pH 7.0) was added to 0.3 mL sample. The mixture of substrate and sample was incubated at 37° C. for 30 min, when the reaction was terminated by adding 0.3 mL 10% trichloroacetic acid. The mixture was allowed to stand for 10 min, then centrifuged at 12,000×g for 5 min. Fifty µL supernatant, 100 µL 0.5 N NaOH, and 50 µL of diluted Folin & Ciocalteu's phenol reagent were pipetted into wells of a 96-well plate and incubated 30 min at room temperature. Absorbance at 660 nm was measured and recorded with a SpectraMax 340PC microplate reader. One unit of protease activity will hydrolyze casein to produce a color equivalent to one µg of tyrosine per minute at pH 7.0 at 37° C. (color by Folin & Ciocalteu's Reagent).

All transgenic callus lines were similar in color and consistency to wild type *N. benthamiana* callus. Callus lines were subcultured monthly and there were no changes in callus appearance over 1.5 years for the CMViva and XVE transgenic lines and over 1 year for the 35S line. The highly sensitive total and functional AAT ELISA and western blotting assays were used to screen and select transgenic cell lines producing rAAT. 33, 17 and 20 independently transformed callus lines with the 35S, XVE and CMViva expression systems, respectively, were screened for rAAT production. Transgenic lines were placed in 6-well-plates containing KCMS medium for cell growth. After 5 days, estradiol was added at a final concentration of 10 µM to induce AAT expression in the XVE and CMViva systems. The 35S callus lines were screened similarly, but no inducer was added. Preliminary ELISA screening for rAAT expression identified cell lines with high concentrations of extracellular rAAT. Extracellular rAAT yields varied widely among independent transformants (data not shown). Extracellular total rAAT was found above 100 µg/L in 40% (14/33) of 35S lines, 12% (2/17) of XVE lines, and 10% (2/20) of CMViva lines. Callus lines producing the most rAAT were established as cell suspensions in 250 mL Erlenmeyer flasks for secondary screening. After secondary screening, candidate cell lines expressing rAAT were confirmed by western blotting (data not shown). The cell lines with highest yield of total and functional rAAT were CMViva-Line 8011, XVE-Line 6011 and 35S-Line 0632; these were selected for bioreactor studies.

Figure 7:
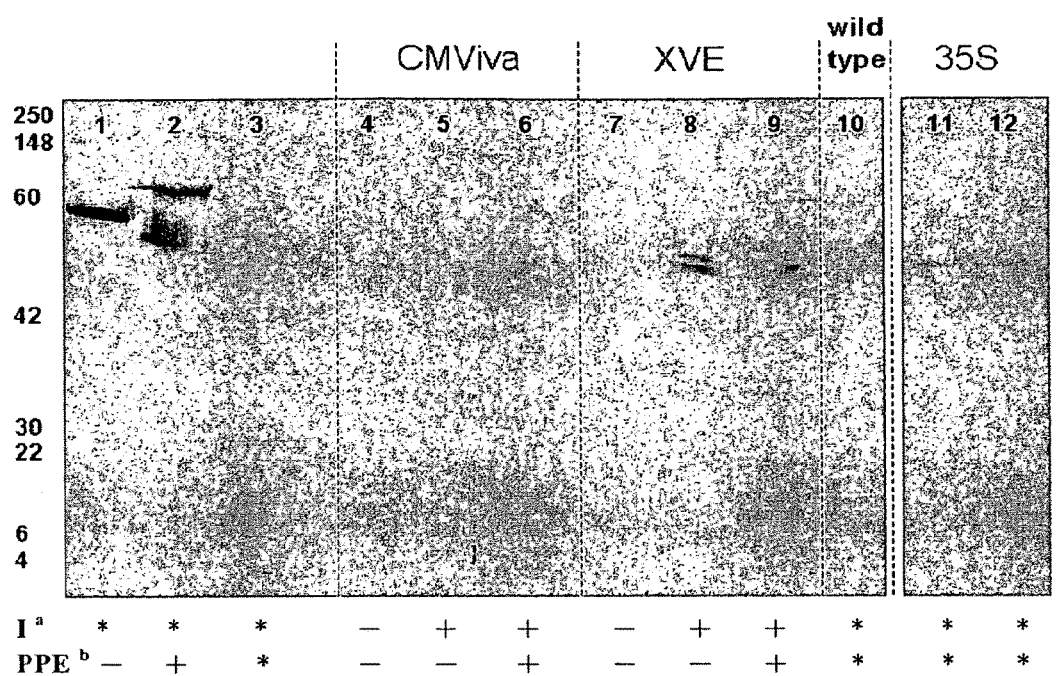

Western blotting and band shift analysis were used to confirm the molecular weight and functionality of expressed rAAT (FIG. 7). All three expression systems were successfully transformed into tobacco and produced detectable extracellular rAAT in suspension cultures (FIG. 7). The rAAT produced by all three systems had a lower molecular weight (~48 kDa) than authentic human AAT (52 kDa) and for some samples, especially from XVE and 35S lines, multiple immunoreactive bands were observed. This could be due to lack of a C-terminal segment (Terashima et al. 1999), different protein conformation (Huang et al. 2001), or differences in glycosylation (Trexler et al. 2002). No immunoreactive bands were detected in the absence of inducer but significant concentrations of rAAT were produced by CMViva and XVE lines after estradiol induction (FIG. 7). Therefore, both inducible systems were tightly regulated. Band shift analysis for functional rAAT showed a characteristic lower MW immunoreactive band for the transgenic samples following PPE incubation, but the higher MW AAT-PPE complex was not detected. Since band shift analysis detects concentrations of AAT greater than 200 µg/L, the more sensitive AAT ELISA was used in subsequent studies to determine the total and functional rAAT concentrations in the extracellular medium.

Figure 8:
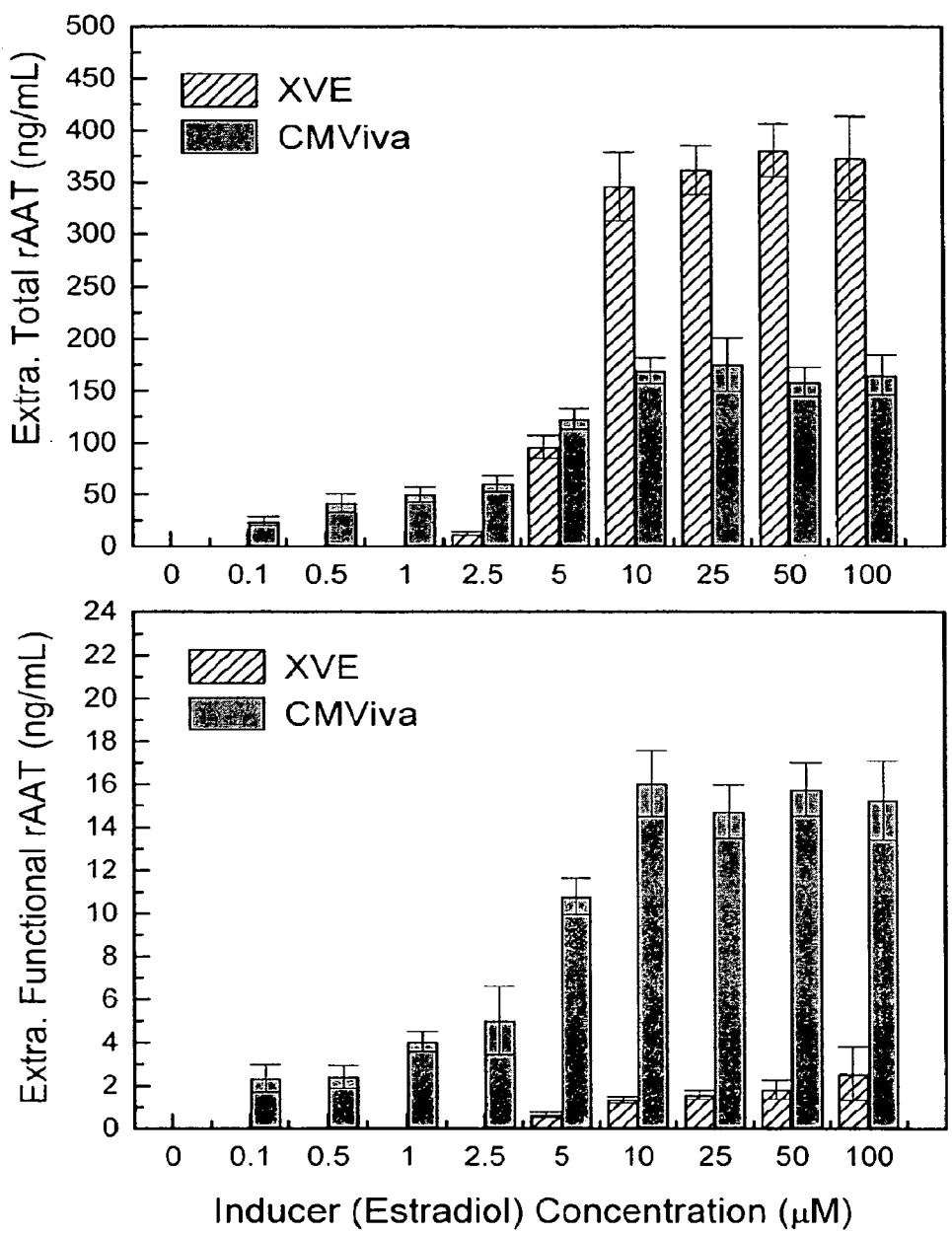

For inducible systems, the correct inducer concentration and timing of application are critical to maximize recombinant protein expression. Two inducible expression systems were evaluated for rAAT protein production. The concentration of inducer (COI) required for inducing maximum rAAT production and the close-response of inducible plant cell cultures were determined. Inducer was added to the XVE and CMViva cell suspensions 10 days after inoculation (100 mL cell culture in a 250 mL Erlenmeyer flask, 140 rpm and 25° C. under ambient light) to a final concentration of 0, 0.1, 0.5, 1, 2.5, 5, 10, 25, 50 or 100 µM. Samples were harvested 8 days after induction and total and functional extracellular rAAT were determined by ELISA (FIG. 8). In the absence of inducer, rAAT was not detected in XVE or CMViva cultures. There was a dose-dependent response in rAAT expression in XVE and CMViva cell cultures with added inducer, and both inducible systems allowed regulation of rAAT expression at inducer concentrations between 0.1 and 10 µM. Above approximately 10 µM estradiol, rAAT production leveled off in both XVE and CMViva systems. The CMViva system first responded at 0.1 µM while XVE required 2.5 µM. Higher extracellular rAAT productivity was produced in CMViva at a relatively low inducer concentration (0.5 µM) compared with that in XVE system (5 µM) and CMViva produced more functional rAAT at all inducer concentrations.

Figure 9:
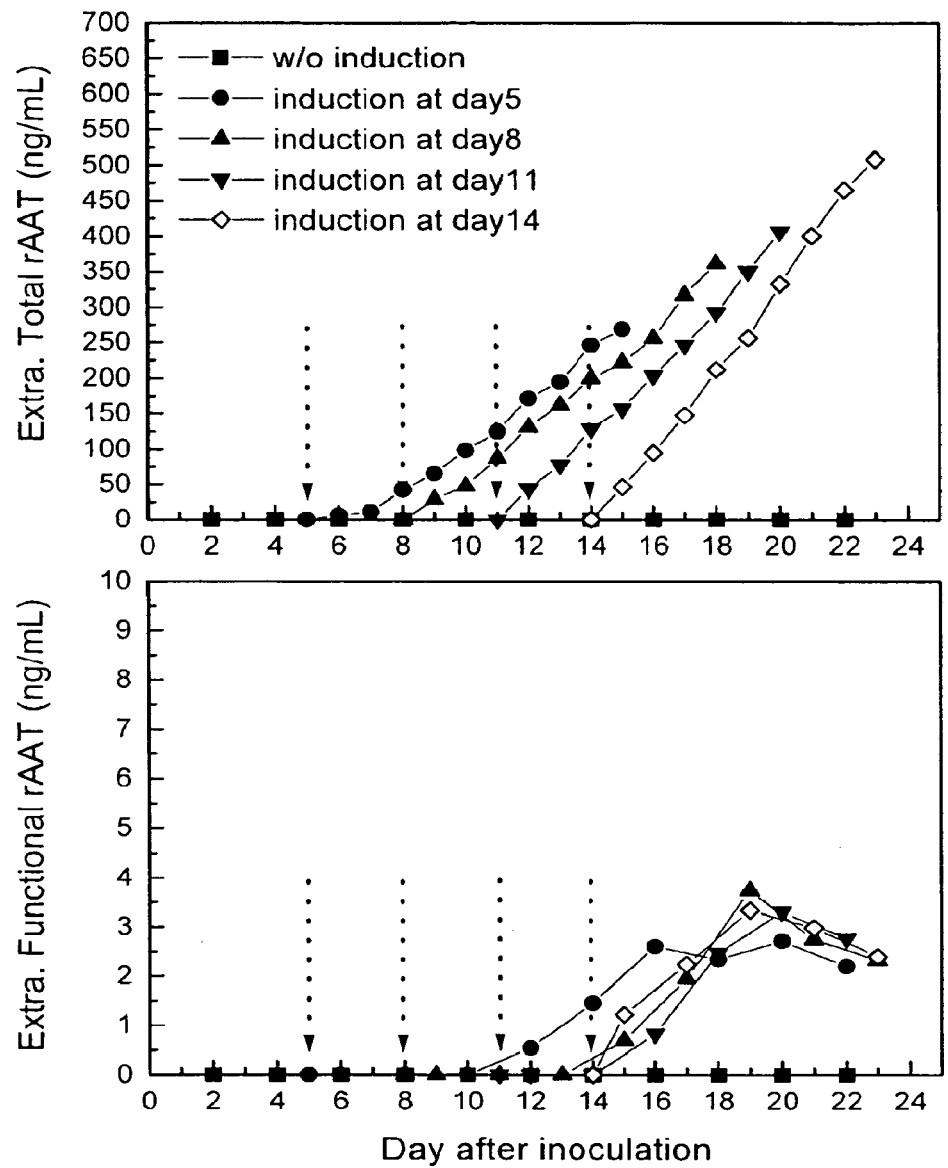

The timing of induction (TOI) relative to the culture growth phase was investigated to maximize rAAT production. To induce rAAT protein expression at various cell physiological states, estradiol was added at a final concentration of 10 µM to 5 (early-exponential phase), 8 (mid-exponential phase), 11 (late-exponential phase) or 14 (stationary phase) day old cultures of XVE and CMViva. Induction of rAAT production in XVE cells was similar over the growth cycle, although cultures induced at day 5 had a 2 day lag phase (FIG. 9). Higher extracellular total rAAT was seen with later induction, but this system produced very little extracellular function rAAT.

Figure 10:
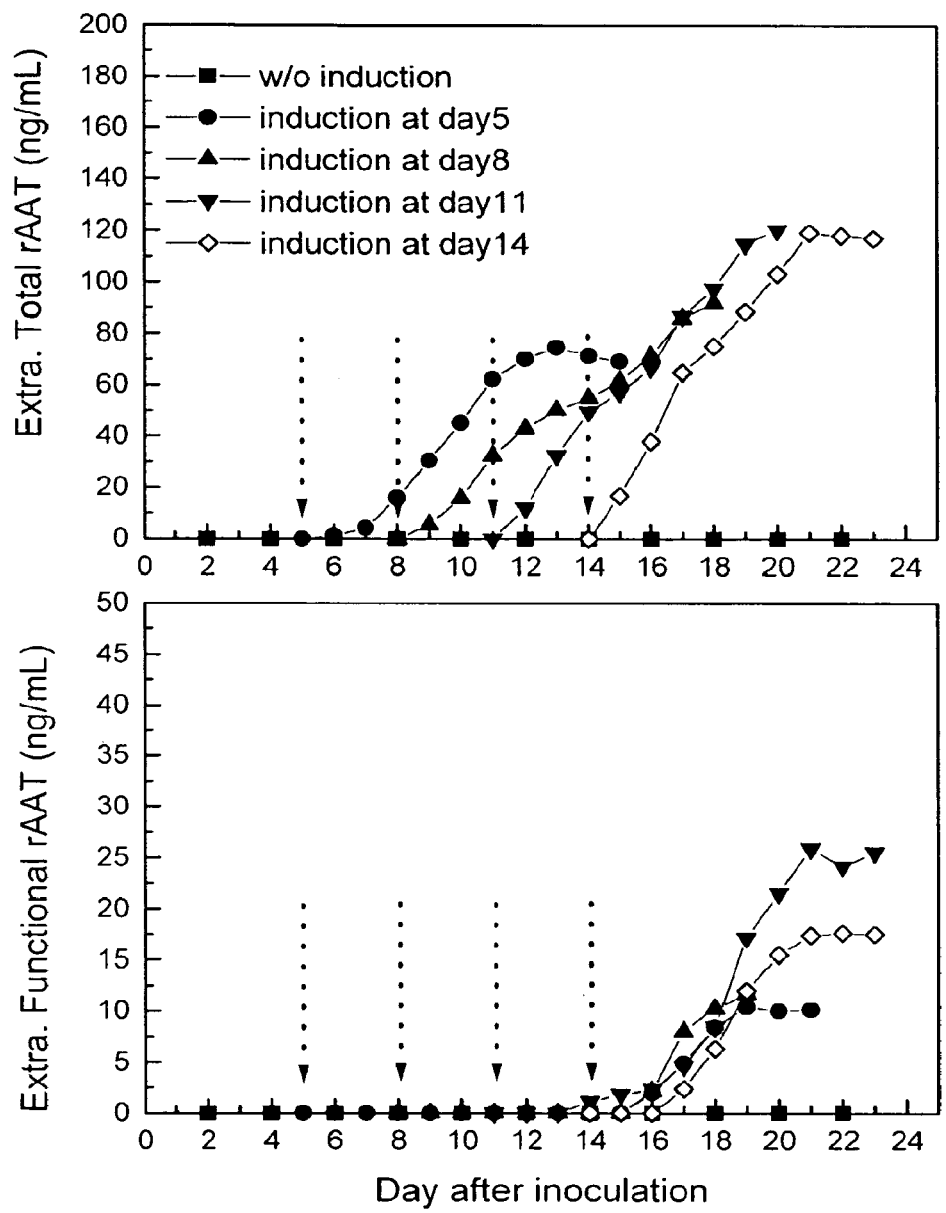

The CMViva system had a similar lag phase for extracellular total rAAT production when induced at day 5 and timing also affected extracellular functional rAAT production (FIG. 10). There was more extracellular functional rAAT in cultures induced at later growth stages, with the greatest yield at 11 days after inoculation. Although total rAAT was secreted and detected by ELISA shortly after applying the inducer, extracellular functional rAAT was not detectable until day 16-18 for all cultures. This implies that some factor in CMViva cell culture may improve functional rAAT protein production or stabilize its functionality in plant cell culture. The yield of extracellular functional rAAT was greater in CMViva cultures than in XVE cultures, although total rAAT was lower.

Based on the above results, the bioreactor studies induced protein synthesis with 10 µM estradiol at 11 days after inoculation. Cell growth (biomass concentration in DCW and FCW), pH, oxygen uptake rate (OUR), extracellular estradiol concentration, total and functional extracellular rAAT concentration and yield of functional rAAT in transgenic plant cell cultures were examined using each of the three gene expression systems and in wild type *N. benthamiana*.

Figure 11:
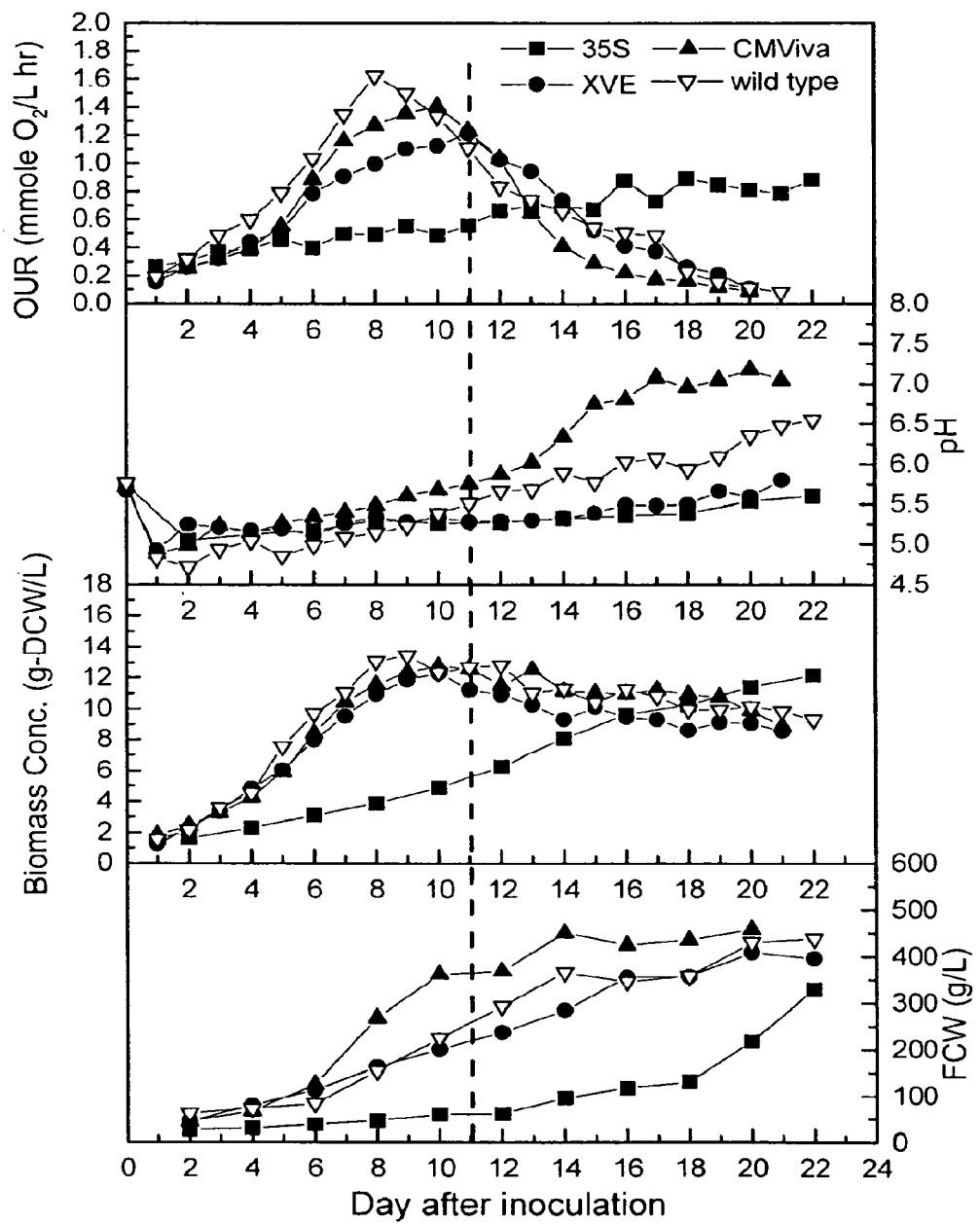
FIG. 11 depicts the growth kinetic comparisons of transgenic plant cell cultures with 35S, XVE or CMViva expression systems and wild type *N. benthamiana* in a bioreactor. Dashed lines represent the time of addition of inducer at day 11 after inoculation for the XVE and CMViva systems.

The cell growth and oxygen uptake rate (OUR) for XVE and CMViva cultures were similar to that of wild type *N. benthamiana* cell culture (FIG. 11, Table 2). The 35S system had a longer lag phase and a lower OUR. The specific growth rate, doubling time, OUR and biomass accumulation in the growth phase of XVE and CMViva cultures were significantly superior to 35S cultures. This implies that cell growth of 35S cultures was inhibited by constitutive rAAT production during the cell growth phase. Interestingly, all three transgenic cultures, but not the wild type control former larger cell aggregates in late stationary phase (data not shown). Extracellular protease activity also varied among gene expression systems. CMViva and wild type cultures produced the most and least extracellular protease activity respectively (Table 2), CMViva cultures also exhibited the highest FCW (450 g-FCW/L) and lowest ratio of DCW to FCW (~3%) (FIG. 11). Extracellular total soluble protein for the three systems was between 143 and 197 mg/L (data not shown). The extracellular pH of 35S and XVE cultures dropped from the initial pH of approximately 5.8 and then gradually increased at day 1 after inoculation. However, the pH increase during induction of CMViva cultures was faster than for the 35S or XVE (FIG. 11).

Figure 12:
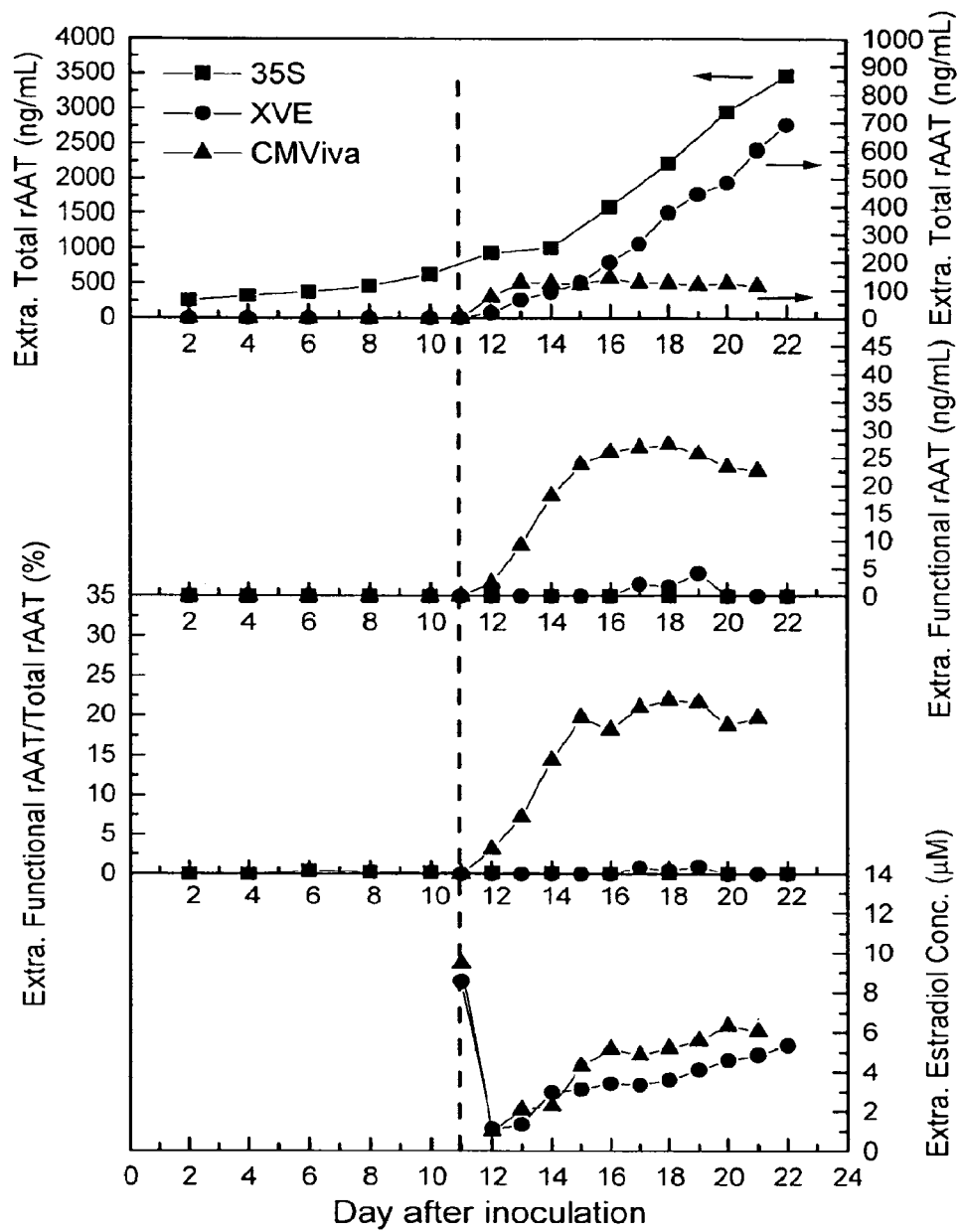
FIG. 12 depicts the comparisons of rAAT production profiles for transgenic plant cell cultures with 35S, XVE or CMViva expression systems and wild type *N. benthamiana* in a bioreactor. Dashed lines represent the timing of induction at day 11 after inoculation for the XVE and CMViva systems.
Figure 13:
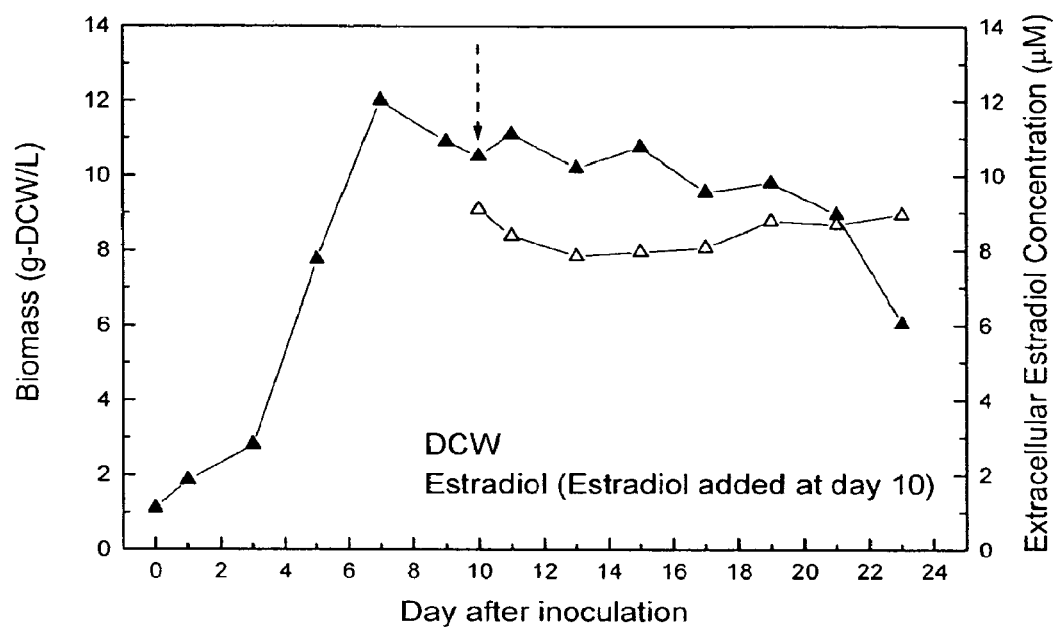
FIG. 13 depicts the kinetics of biomass accumulation and extracellular estradiol concentration in wild type *N. benthamiana* cell cultures grown in a flask. The dashed line represents the timing of induction at day 10 after inoculation.

The yield and functionality of rAAT produced by the three transgenic cultures were measured by total and functional AAT ELISA. The CMViva transgenic line had the highest titers of functional rAAT: 22% of the total rAAT expressed was found to be functional, defined as capable of irreversible binding to porcine pancreatic elastase, PPE (FIG. 12). Furthermore, rAAT production reached a maximum in the CMViva system faster than in the other systems. The rAAT titers did not decline, even during the late stationary phase, in any of the three systems, but total and functional rAAT leveled off for CMViva around 5 days after induction. The functional extracellular rAAT in 35S and XVE cultures was very low, close to the detection limit. In the absence of inducer, rAAT was not detected in XVE and CMViva cultures, demonstrating tight regulation. Estradiol was quickly depleted from the culture medium after induction (from 9.3 $\mu$M to 0.8 $\mu$M) but 2 days after induction the estradiol concentration in the culture medium gradually increased (FIG. 12). It is not clear what caused either the rapid uptake or the slow release of estradiol to the culture medium. To elucidate the possible mechanism for this concentration change, 10 estradiol was added to a flask of wild type N. benthamiana cells 10 days after inoculation, and the kinetics of cell growth and extracellular estradiol concentration were determined (FIG. 13). Interestingly, the extracellular estradiol concentration remained relatively stable at 7.84-9.08 $\mu$M. This suggests that the estradiol depletion and slow release in XVE and CMViva cultures is not due to physical factors such as surface adsorption to cell aggregates and/or estradiol degradation, but may represent intracellular uptake of estradiol by the XVE and CMViva cells.

Detectable rAAT expression was seen in the XVE and CMViva systems at estradiol concentrations as low as 100 nM (the lowest concentration tested) and it reached saturation at ~10 $\mu$M estradiol. Previous studies using the XVE system found detectable GFP transcripts in plants induced with 8 nM estradiol (Zuo et al. 2000) and GFP fluorescence in viral amplicon plant cell cultures induced with 10 nM estradiol (Dohi et al.). Saturation was reached around 5 $\mu$M estradiol for GFP transcripts in whole plants and 0.1-1 $\mu$M estradiol for GPF fluorescence using the viral amplicon system in plant cell culture. Since rAAT titers level off at estradiol concentrations above 10 $\mu$M, some other factor may become limiting such as the constitutively produced XVE fusion protein. The concentration-dependent induction of XVE and CMViva cultures, suggests that rAAT expression can be regulated by estradiol concentrations between 0.1 and 10 $\mu$M. Although this was expected for XVE, a binary response (off without estradiol and fully on with estradiol) would be expected for a truly autocatalytic viral amplicon system. However, in the CMViva system, CMV 1a transcripts are not replicated in the presence of viral replicase due to the 57-nucleotide deletion at the 5' end of the CMV RNA1 cDNA. Thus the CMViva system is not autocatalytic since CMV 1a transcription is controlled by the XVE promoter, independent of functional replicase. This makes the CMViva system less prone to leakiness and its expression is more controllable. The CMViva system was more sensitive to estradiol than the XVE system, producing detectable rAAT at just 0.1 $\mu$M estradiol instead of 2.5 $\mu$M. The XVE promoter was tightly regulated with no rAAT detected in the absence of estradiol and estradiol caused no obvious detrimental, toxic, or growth-inhibiting effects on N. benthamiana cultures at up to 100 $\mu$M. Although 10 $\mu$M estradiol was adequate for batch suspension cultures in flasks, higher estradiol concentrations and multiple or continuous applications may benefit fed-batch cultures or other high cell density operational modes.

Timing of induction is also important to optimizing productivity of chemically inducible expression systems. Since heterologous gene expression can significantly impact cell physiology and growth, induction during the early stage of culture may limit production due to lower biomass. Post-transcriptional gene silencing responses may also be stronger during early and mid-exponential growth states. During the late stationary phase cells may already be nutrient deprived, under stress, slowing metabolism/biosynthesis, secreting proteases and/or dying. Maximum total and functional rAAT were obtained when the inducer was added during the late exponential phase of growth, 11 days after inoculation.

The performance of transgenic N. benthamiana cultures with three gene expression systems were evaluated in bioreactors for cell growth and human rAAT production yield and functionality. The maximum specific growth rates, oxygen uptake rates and biomass concentrations obtained with XVE and CMViva cultures were similar to the wild type cultures (Table 2, FIG. 11), indicating that the chemically inducible cultures were physiologically indistinguishable from the wild type cultures prior to induction. The fact that the XVE and CMViva callus and cell suspension were subcultured for over 18 months with no observable changes in phenotype or differences from wild type callus/cell lines also supports this conclusion. No recombinant AAT was detected in the XVE or CMViva culture broths prior to induction, indicating tight regulation and negligible leakiness for the XVE promoter. Viral RNA and product (GFP) were not detected in an inducible tomato mosaic viral amplicon system using the XVE promoter in stably transformed tobacco BY-2 cells (Dohi et al. 2006). The 35S culture had a lag phase and the maximum specific growth rate and oxygen uptake rate were significantly lower than for the wild type and other transgenic lines, presumably a result of the metabolic burden associated with constitutive rAAT expression.

Following induction, the CMViva culture had more extracellular protease activity and a more rapid pH increase than the other transgenic cell lines. Heterologous protein expression by the CMViva viral amplicon may require more energy to produce target protein and/or affect the plant cell physiology. In an ethanol-inducible plant DNA viral amplicon expression system, excessive accumulation of either Rep (the viral replication initiator protein) or viral amplicon components during the late stage of induction had a toxic effect on tobacco NT1 cells (Zhang and Mason 2006).

As shown in FIG. 12, there were significant differences in the kinetics of rAAT production and the total and functional extracellular rAAT observed for the three transgenic cultures. Although the 35S and XVE cell lines had higher levels of extracellular total rAAT, the levels of functional rAAT were very low or undetectable in these cultures. The highest extracellular concentration of functional rAAT (27 $\mu$g/L) and highest ratio of functional rAAT to total rAAT (22%) were observed from the CMViva plant cell cultures four days after induction. It appears that functional rAAT is relatively unstable in the tobacco culture medium and the accumulation of functional rAAT may depend strongly on the production kinetics relative to the kinetics of reactions involved in the loss of bioactivity. The production of extracellular rAAT in the CMViva culture indicates that functional viral replicase is produced after induction and that the secretion signal peptide is effective in targeting the product to the culture medium. The relatively high levels of functional rAAT suggests that the intracellular replication machinery inherent in the CMViva expression system may be beneficial for amplifying the mRNA of the target gene (AAT). In addition, higher functional rAAT yield might be also contributed to by the 2b protein, a potent silencing suppressor in CMViva system, which may decrease PTGS. However, the CMViva system produced the lowest level of extracellular total rAAT. It should be noted that the CMViva cell cultures in a bioreactor exhibited the highest FCW and the lowest ratio of DCW to FCW during the induction phase (FIG. 11). Plant cells from a phase of rapid cell division usually have smaller size, smaller vacuoles and lower water content than cells from the stationary growth phase. This suggests that the vacuoles in CMViva cell cultures may contribute to the FCW of plant cells. Plant vacuoles contain a variety of proteases that are active under mildly acidic conditions that may be released upon cell death. Furthermore, the extracellular protease activity level during CMViva cell cultures is higher than in XVE and 35S cell cultures (Table 2). Thus, a more rapid cell death following induction coupled with higher protease levels might explain why CMViva cell cultures produced lower total rAAT yield than the XVE and 35S cell cultures. Although we selected the highest producing cell lines for each expression system, differences in positional effects of T-DNA integration between the different transgenic lines may also impact expression levels (Wilson et al. 1990).

In this example, an immunoassay was utilized for the quantitative kinetic analysis of estradiol in the chemically inducible plant cell cultures (XVE and CMViva system). Estradiol binds to the XVE fusion protein which causes the XVE protein to dimerize and function as a transcriptional activator for the LexA promoter. The data show that estradiol is rapidly depleted from the XVE and CMViva culture broths within 24 hours after it is introduced (FIG. 12). Interestingly, estradiol is not depleted from the culture broth when added to wild type N. benth cultures, suggesting that the depletion from the culture medium is not due to physical processes (e.g. adsorption to cell aggregates, instability of estradiol in the culture broth, etc) but may be due to intracellular uptake of estradiol by the XVE and CMViva cells. Estradiol is then gradually released into extracellular medium over the next ten days (FIG. 12). This release may be due to cell lysis and/or diffusion of estradiol from the cell once it is no longer bound to XVE.

In summary, the novel inducible plant viral amplicon system (CMViva), previously demonstrated by *Agrobacterium*-mediated transient expression in *N. benthamiana* leaf tissue (see previous examples), can also be used for production of functional rAAT in stably transformed to *N. benthamiana* cells in bioreactors. Similarly to the results obtained using transient expression in *N. benthamiana* leaf tissue, we obtained the highest levels of extracellular functional rAAT with the CMViva expression system when compared to a constitutive CaMV 35S system and the chemically XVE system. Table 3 compares recombinant AAT production using CMViva system by transient expression in *N. benthamiana* leaves with and without co-infiltration with the p19 gene silencing suppressor, and transgenic *N. benthamiana* cell culture in a bioreactor in this study (without p19 expression). Functional rAAT production was 8-fold lower on a % TSP basis and 100-fold lower on a % DCW basis for the transgenic CMViva cell culture compared to transient agroinfiltration in plant leaves without the p19 gene silencing suppressor. However, the ratio of functional rAAT to total rAAT was similar, 22~28%, for both systems. There are several possible explanations for the differences in productivity observed between the transgenic cell culture and transient leaf-based production systems. First, only extracellular rAAT was measured in the transgenic cell culture analysis; cell aggregate-associated and/or intracellular rAAT was not included. For the transient system, rAAT was measured in extracts of leaf tissue. Secondly, there may be significant differences in the stability of rAAT in the leaf apoplast versus the plant cell culture medium due to differences in concentration, type and activity of proteolytic enzymes as well as physiochemical differences (e.g. pH, composition, etc). Thirdly, inherent differences in the mechanisms involved in transient expression versus expression from a stably integrated transgene may be responsible. Other investigators have reported higher productivity using transient expression compared with stably transformed lines (Wroblewski et al. 2005), attributing the differences to the relative timing of the onset of PTGS compared to transgene expression. Since the stably transformed CMViva cultures constitutively express a number of heterologous proteins (XVE, CMV 2a, and CMV 3a) it may be that PTGS has already been established prior to induction. Although the CMV 2b protein is known to be a potent gene silencing suppressor, since it is coded by a subgenomic RNA, it will only be produced after induction. Furthermore, previous examples demonstrated that co-infiltration with *agrobacterium* containing an expression cassette for p19 could significantly improve the rAAT production yield and quality (Table 3). Therefore, it may be possible to enhance productivity in the transgenic CMViva cell line through constitutive expression of p19, CMV 2b or other gene silencing suppressors or by transient agroinfiltration of the CMViva cell aggregates for expression of gene silencing suppressors prior to induction.

Example 14: Production of Functional Recombinant Human Protein in Transgenic Tobacco Cell Cultures: Culture Strategy of Improving Heterologous Protein Production Changes in culture pH were applied during recombinant protein production as a strategy to minimize the production, secretion and/or activity of extracellular proteases capable of degrading extracellular recombinant protein products. The following example demonstrates an inducible expression of a replicable viral amplicon for human protein production in transgenic tobacco cell cultures in bioreactor and for the beneficial influences of pH on the production yield and functionality of recombinant human protein.

The p35S-spAAT (35S), pXVE-spAAT (XVE) and pCMV-spAAT (CMViva) expression vector constructions are described in previous examples. Three different expression systems have been stably transformed into *N. benthamiana* cells using *Agrobacterium*-mediated transformation by the *Agrobacterium tumefaciens* strain EHA105 carrying the appropriate binary vectors as described in example 11.

Transgenic *N. benthamiana* suspension cell cultures transformed with one of three gene expression systems expressing human AAT protein were established and screened as described in the previous examples. Cell lines with the highest extracellular titers, 35S line #0632, XVE line #6011 and CMViva line #8011, were selected for further study. Transgenic *N. benthamiana* cell cultures were maintained in KCMS medium, which consists of 30 g/L sucrose, 4.3 g/L MS salt mixture, 0.1 g/L myo-inositol, 0.204 g/L KH2PO4, 0.5 mg/L nicotinic acid, 0.5 mg/L thiamine-HCl, 0.5 mg/L pyridoxine-HCl, 0.2 mg/L 2,4-D, and 0.1 mg/L kinetin and was adjusted to pH 5.8 with KOH prior to autoclaving at 121□ for 26 min, containing 100 mg/L kanamycin and subcultured weekly by transferring 10 mL of established suspension cells into 90 mL KCMS medium in a 250 mL flask at 140 rpm and 25□ under ambient light.

17-beta-estradiol prepared in DMSO as a chemical inducer solution was added to plant cell cultures (for the XVE and CMViva transgenic cell lines) at a specific time after inoculation at a final concentration of 10 μM to start the induction phase. No inducer solution was applied to wild type (untransformed) N. benthamiana cell culture as negative control or to transgenic plant cell cultures with the 35S constitutive promoter.

Plant cell cultures were grown in a New Brunswick Scientific BioFlo 3000 bioreactor (3.6 L working volume) with basic environmental conditions set as described in example 11.

Before the induction phase, medium exchanges were performed by connecting sterile tubing from an autoclaved bottle to the bioreactor. A peristaltic pump was used to draw cultured medium from the bioreactor into a bottle at a speed of approximately 50~60 mL/min (agitation and aeration were kept on during the medium removal). A ring sparger with 11 holes (~1 mm diameter) was positioned close to the bottom of the bioreactor to filter out the medium while retaining the plant cells in the bioreactor. After removing most of cultured medium (about 1,800 mL), an equivalent volume of fresh sterile KCMS medium was pumped into the bioreactor. After the inducer solution prepared in DMSO was added into bioreactor at a final concentration of 10 μM for the inducible promoter systems (XVE and CMViva), 0.5 N NaOH was added periodically to keep the culture pH higher than 6.4 (one-sided pH control) using base-addition manual mode through the operator interface of the New Brunswick Scientific BioFlo 3000 bioreactor. No medium exchange and induction strategies were applied to plant cell cultures with the constitute 35S promoter but pH control was applied at specific time after inoculation.

Fresh cell weight (FCW) was measured by filtering a 10 mL sample onto a pre-dried, pre-weighed, Whatman #1 filter connected to a vacuum and washing the cells with 20 mL of ddH2O to remove residual sugars from the cell surfaces, then weighing the cells. Dry cell weight (DCW) was estimated after drying the retained cells at 60 deg. C. for 2 days.

The methods of protein analysis including total soluble protein (TSP), western blotting, band shift assay for functional AAT analysis, total AAT ELISA and functional AAT ELISA were performed as previously described in previous examples.

The concentration of estradiol in cell culture medium was measured by an immunoassay based on the principle of competitive binding as described in the previous examples.

The protease activity in cell culture medium was quantified by according to a procedure which has been described in the previous examples.

For the investigation of human AAT stability in plant cell cultures, human AAT was added to the cell-free conditioned medium to a final concentration of 2 mg/L and distributed into 6-well-plates. The cell-free conditioned medium was prepared by centrifuging and filtering (through a 0.22 μm filter) the plant cells from 7 day old CMViva cell cultures (pH 5.1). Various protease inhibitors including 2-mercaptoethylamine-HCl (aminopeptidase inhibitor), AEBSF (serine and cysteine proteases inhibitor), benzamidine-HCl (serine protease inhibitor), and EDTA (a metal ion chelator and metalloproteinase inhibitor) were added to the conditioned medium to a final concentration of 10 mM to assess their ability to retard the degradation of human AAT. In another treatment, the conditioned medium was also heated (in boiling water for 30 minutes) or the medium pH was adjusted (from original pH 5.1 to 6.4~6.6) prior to the addition of human AAT to investigate the human AAT stability. The 6-well-plates containing human AAT in various conditioned medium (4 mL/well) were incubated on an orbital shaker at 140 rpm and 25□ under ambient light. Samples were taken daily and stored at −80° for further ELISA, western blotting and band shift analysis.

To understand the recombinant AAT protein stability in plant cell cultures, commercially available human AAT was spiked into various cell-free conditioned culture media to determine the total and functional human AAT concentration change over time. A preliminary study was performed to examine the stability of human AAT in cell-free cultured medium prepared from 7 day old wild type N. benthamiana or transgenic CMViva cell cultures. Western blot and AAT ELISA analyses were applied to examine the degradation of human AAT over time (FIG. 14). The human AAT was unstable in cultured medium (free of cells) and degraded very quickly in both of the tobacco cell culture media. ELISA assays showed that after 1 day, there was only approximately 23% of the initial functional human AAT remaining in wild type cell culture medium and no detectable human AAT in CMViva cell culture medium. The immunoblot analysis showed a concomitant reduction in the intensity of the highest immunoreactive band and a corresponding increase in intensity of a lower immunoreactive band for the wild type N. benth culture broth, which corresponded well with the loss of functional human AAT protein. For the CMViva culture broth two immunoreactive bands were observed even after 0.5 days and the intensity of both bands dropped off dramatically from 0.5 to 1 day incubation. It should be noted that some degradation products were observed at lower molecular weight.

Various protease inhibitors and other strategies were investigated to enhance the stability of human AAT in cultured medium. The stability of human AAT in cell-free plant cell culture medium with various treatments is shown in FIG. 15. It is interesting to note that functional human AAT levels decline by almost 50% over a 5 day incubation even in fresh, sterile KCMS medium at a pH of 5.8, while the total human AAT level declines slightly (about 25%) over that time period. In the 7 day old cell-free CMViva culture medium (which typically has a pH about 5.0), the functional human AAT is negligible within 2 days, while the total human AAT level declines by 60% over the 5 day incubation period. When the CMViva culture medium was adjusted to pH 6.4 the stability of human AAT protein improved, with 40% of the functional AAT remaining at day 2 and about 20% remaining at day 5. It should also be noticed that the total human AAT only declines about 25% over the 5 day period at the higher pH, compared with the 60% loss at pH~5.0. These data suggest that culture medium pH influences human AAT stability; increased pH slows the rate of degradation of functional AAT in the spent CMViva cell culture medium. In addition, the functional human AAT was much more stable in the heated CMViva culture medium with functional human AAT maintained as high as 70% of the initial concentration after 5 days. This suggests that some heat-labile media components, perhaps proteolytic enzymes, may be present in the cultured medium. Different types of protease inhibitors (serine and cysteine proteases, aminopeptidase, and metalloproteinase inhibitors) were added to cultured medium to a final concentration of 10 mM to assess whether protease inhibitors alone could retard human AAT degradation. The addition of the cysteine and serine protease inhibitor (AEBSF) showed the highest ability to stabilize functional human AAT levels with results similar to increasing the medium pH at 6.4. It therefore indicated that proteases in the cell cultured medium may be contributing to the observed degradation of human AAT and also implied that at least serine and cysteine proteases are involved in the human AAT degradation. Medium additives other than protease inhibitors including bacitracin, PVP, mannitol and BSA, have also been examined. However, these stabilizing agents did not show significant effect on stabilizing the functional human AAT protein (data not shown). Although other papers have shown that medium additives or stabilizing agents can improve recombinant protein production, these data imply that pH is an important factor for affecting the stability of human proteins. FIG. 2 clearly shows that the total human AAT in cultured medium at pH 6.4 was relatively stable and the functionality of human AAT was degraded slowly compared with that in conditioned medium with an original pH 5.1 or in media containing other protease inhibitors. These results indicated that culture medium with higher pH may decrease protease activity and/or help maintain the structure and functionality of human AAT.

Western blots and band shift assays were applied to examine the stability and functionality of human AAT in various conditioned medium (FIGS. 16A and 16B). As shown in FIG. 16A, it was obvious that human AAT in heated conditioned medium (FIG. 16A, lane 4) and conditioned medium at pH 6.4 (FIG. 16A, lane 3) showed a higher AAT level (more intense highest band) than both that in original conditioned medium at pH 5.1 (FIG. 16A, lane 9) and in conditioned medium containing various protease inhibitors and/or protein stabilizers (FIG. 16A, lane 5~8). Of the various protease inhibitors, the sample containing AEBSF had the most intense top band. To examine the functionality of human AAT, band shift analysis was applied. FIG. 16B shows that human AAT in the heated conditioned medium (FIG. 16B, lane 4) and conditioned medium at pH 6.4 (FIG. 16B, lane 3) exhibited a significant band shift at 75 kDa (AAT-PPE covalent complex, a reaction product of AAT binding to PPE) and a lower band (the cleaved product of the AAT-PPE reaction), as did the human AAT control (FIG. 16B, lane 1), but the characteristic band shift was not shown in original conditioned medium (FIG. 16B, lane 9) and was lighter in conditioned medium containing various protease inhibitors (FIG. 16B, lane 5~8). Of the various protease inhibitors, the sample containing AEBSF had the strongest immunoreactive band corresponding to the AAT-PPE complex. These data showed that the proteolytic degradation of human AAT in cultured medium was evident and pH is an important factor for affecting the stability and functionality of human AAT in cell culture medium.

To further understand the pH protective effect on making human AAT less susceptible to proteolytic degradation or stabilizing human AAT in plant cell culture medium, the stability of human AAT was investigated in conditioned medium collected from different CMViva cell cultures at various ages. Human AAT was added to cell-free cultured medium at 7, 11 and 16 days old post-inoculation, collected during the exponential phase, early stationary phase and late stationary phase, respectively, of CMViva cell cultures grown in flask to evaluate the effect of culture broth components on human AAT stability. Interestingly, as shown in FIG. 17, the kinetics of human AAT degradation varied significantly in different age cell-free cultured medium. Functional human AAT was degraded quickly in 7 day-old cultured medium (pH 5.1) but was relatively stable in 11 day-old conditioned medium (pH 5.9) and much more stable in 16 day-old conditioned medium (pH 6.9). This is particularly noteworthy as we would expect that the levels of extracellular proteases would increase with culture age. These data suggest that higher medium pH is favorable to stabilize functional human AAT and/or reduces the activity of medium factors contributing to human AAT degradation. To understand the effect of medium pH on human AAT stability, human AAT was added to 11 day-old cell-free CMViva cultured medium, which was adjusted to different pH values (4, 5, 6, 7 or 8). The degradation kinetics of human AAT in cultured medium with various medium pH is shown in FIG. 18. It was found that higher medium pH (7~8) maintains the functionality of human AAT but lower medium pH (4~5) accelerates the loss of functionality. Accordingly, increasing the medium pH could increase the stability and functionality of human AAT in the cell culture medium, presumably by decreasing the activity of proteolytic factors, which are responsible to human AAT degradation in cultured medium, and/or providing a favorable environment for the correct conformation of human AAT, which could execute its functionality for binding elastase.

Since medium pH plays an important role in stabilizing extracellular human AAT, we investigated whether increasing the culture pH during the protein production phase in the transgenic plant cell cultures could improve the functional rAAT production yield. An induction medium with a higher pH may decrease protease activity and/or maintain the functionality of recombinant AAT. According to this hypothesis, a rational induction strategy was proposed to improve the total and functional rAAT production by performing a medium exchange before induction (to remove most of the proteases in the cell culture medium) and also increasing the medium pH (to decrease protease activity and/or stabilize the conformation of functional AAT) during the protein production phase.

An initial study was first performed to assess the effect of medium exchange and medium pH on rAAT production in the CMViva system in shake flasks comparing 1) adding the inducer only, 2) performing a medium exchange before induction and then adding the inducer, and 3) performing a medium exchange before induction, then adding the inducer and adjusting the pH by adding NaOH to maintain the pH between 6.4~6.8 every 12 hours, respectively (FIG. 19). During the induction phase for the case of the medium exchange without pH control, the pH profile was fairly stable and relatively low (5.1~5.6). Although medium exchange was expected to remove most of extracellular proteases, the total and functional rAAT was at the lowest level compared with other induction strategies. When the pH is adjusted to a higher level during the induction phase following a medium exchange, the total and functional rAAT yield was increased and the ratio of functional rAAT to total rAAT was enhanced from 0% (medium exchange, induction and without pH control) to 40% (medium exchange, induction and pH control). Thus, a culture medium with higher pH during the protein production phase can improve functional rAAT productivity. Consequently, pH is an important variable, which exhibits a strong influence on the stability of human proteins for process optimization of plant cell cultures.

To confirm that the pH control strategy can be realized during the protein production phase in plant cell cultures in bioreactors, the effect of implementing a pH shift on rAAT production was investigated in all three systems (35S, XVE and CMViva). Medium exchange was performed before induction and pH adjustment in the bioreactor for the XVE and CMViva systems to provide additional nutrients. FIGS. 20, 21, and 22 show the effect of pH control on total and functional rAAT production for the XVE, CMViva and 35S systems, respectively. Significantly, in each system, functional rAAT titers improved dramatically when the pH during the production phase was maintained at a higher value. In all cases, the total rAAT titers increased as well as the functional rAAT titer. With pH control, the CMViva cell culture achieved a higher level of extracellular functional rAAT (100 ng/mL) and a higher ratio of functional rAAT to total rAAT (48%) in four days after induction than for the XVE system (60 ng/mL and 7.1%). For the 35S system, two pH profiles were applied to the cell culture at day 12 after inoculation (FIG. 22). These data showed that functional and total rAAT production could be further improved at higher pH (6.8) and that the pH shift did not significantly inhibit plant cells growth. Thus, pH control during protein production is useful strategy for improving the production yield and functionality of recombinant human protein in plant cell culture.

The results show that human AAT is unstable and is degraded rapidly in media in which wild type and transgenic N. benthamiana plant cells have been grown. To elucidate the mechanism of the loss of functional AAT in plant cell cultures, experiments with human AAT spiked into fresh KCMS medium, heated cultured medium and other cell-free conditioned medium containing protease inhibitors or altered pH demonstrated that the heat labile components, most likely plant cell derived proteases, in the medium were primarily responsible for the loss or degradation of human AAT in cultured medium. The results further suggest that higher medium pH may decrease protease activity and/or stabilize human AAT protein conformation facilitating it's binding to elastase (PPE) or reducing it's susceptibility for binding and/or cleavage by proteases. Additionally, the serine and cysteine protease inhibitor (AEBSF) and aminopeptidase inhibitor (2-mercaptoethylamine-HCl) could slightly inhibit human AAT degradation in the cell cultured medium (FIGS. 15, 16A and 16B), indicating that serine and cysteine proteases or aminopeptidase present in the culture medium may contribute to the human AAT degradation. Work by Schiermeyer and coworkers (Schiermeyer et al. 2005) indicates that metalloproteases are responsible for the DSPAα1 protein degradation in tobacco cell culture medium and can be inhibited by the addition of EDTA. The effect of stabilizing agents (bacitracin, PVP, BSA, Pluronic F-68, and mannitol) and protease inhibitors (2-mercaptoethylamine-HCl, AEBSF, benzamidine-HCl and EDTA) on the rAAT production in transgenic plant cell cultures was also evaluated. However, no significant improvement on total and functional rAAT production was achieved (data not shown). Thus, the ability of stabilizing agents or protease inhibitors to inhibit target protein degradation has to be evaluated on a case-by-case basis.

When the culture pH in the bioreactor is maintained at a higher level during production, the levels of functional extracellular rAAT are significantly enhanced in all of the transgenic plant cell cultures studied (FIGS. 20, 21, and 22). This further suggests that functional rAAT was successfully translated, folded and secreted into extracellular medium and rAAT produced in transgenic tobacco cell cultures was degraded due to the proteolysis in the cell culture medium irrespective of the gene expression system used to express the rAAT protein. These results demonstrate an effective strategy for improving human protein production yield and quality by using optimized culture conditions and altered environmental conditions during the protein production phase, such as increasing the culture pH, as an alternative to adding protease inhibitors or protein stabilizing agents in plant cell culture.

A recent study (Becerra-Arteaga et al. 2006) indicated the possibility that thioredoxin, a disulfide reducing protein, could be a destabilizing factor that contributes to the denaturation of extracellular recombinant proteins in tobacco cell cultures, however AAT has no disulfide bonds. AAT is a member of the serpins superfamiliy (serine protease inhibitors) in which membership is based on the presence of a single common core domain consisting of 3β-sheets, 8-9 α-helices and a reactive center loop (RCL) (Gettings et al., 2002). AAT inhibits its target protease (such as tripsin or elastase) by forming a stable and irreversible covalent binding complex in which the Met358-Ser359 bond in the RCL of AAT is cleaved and the RCL is inserted into a β-sheet of the AAT (Huntington et al., 2000). The structure of RCL is the most variable region and is crucial for the activity of AAT. In addition, human AAT is a metastable and conformationally flexible protein and contains nine methionines and a cysteine in its primary sequence. Oxidative damage of methionines or cysteine in the protein active site to a sulfoxide derivative has been reported to result in a loss of inhibitory activity against elastase of AAT (Griffiths et al., 2002). The methionines in AAT have been replaced by valines. Although considering the possibility of oxidation of cysteine in expressed rAAT in this study, variation of medium pH could induce the conformational or structural changes in the region surrounding cysteine or reactive center loop (RCL), which dominates the activity of binding target proteinase, and further alter the functionality of human AAT for binding elastase. Additionally, although the cysteine residue of AAT could form a disulfide bridge with free cysteine (Kolarich et al., 2006), the results show that both total and functional human AAT are degraded in the cultured medium over time. Furthermore, the serine and cysteine protease inhibitor (AEBSF) help to retard the human AAT degradation in cultured medium (FIGS. 15, 16A and 16B). Therefore, the proteolytic degradation of functional rAAT was observed and confirmed in this study. Consequently, the pH strategy proposed herein could both decrease protease activity and additionally stabilize the correct conformation of AAT for executing its functionality.

The novel CMViva expression system, as described in the previous examples, has been demonstrated that it could result in higher functional recombinant AAT production yield by transient expression in N. benthamiana leaves or transgenic N. benthamiana cell culture in a bioreactor (see example 11) when compared with the expression levels observed using either the CaMV 35S constitutive promoter system or a chemically estradiol-inducible, estrogen receptor-based promoter (XVE) system. This example proposes a pH condition-shifting culture strategy for increasing the functional rAAT production yield (100 ng/mL) and the ratio of functional rAAT to total rAAT (48%) in CMViva system. The comparisons of recombinant AAT production using CMViva system from various systems are shown in Table 4. It apparently shows that functional recombinant AAT production could be further improved by using a pH shifting culture strategy in transgenic plant cell cultures, suggesting that the rAAT productivity by transgenic plant cell cultures could potentially compete with the levels achieved by transient agroinfiltration in plant leaves and furthermore the rAAT production is exposed to severe proteolytic degradation and rAAT protein is unstable in tobacco cell cultures.

Example 15: HIGH-LEVEL TRANSIENT PRODUCTION OF HETEROLOGOUS PROTEINS IN Plants by Optimizing Induction of a Chemically Inducible Viral Amplicon Expression System The following example demonstrates two different methods of chemical treatment application, topical application and pressure injection/infiltration, on heterologous protein production are described. Details regarding construction of the CMViva expression vector are described in previous examples.

Non-transgenic/wildtype N. benthamiana seedlings were grown from seed in soil-filled 10-cm pots. Seedlings were transplanted to individual 10-cm pots until plants were 10 to 15 cm in height, at which time plants were ready for infiltration. All plants were grown in a greenhouse with a 16-hour photoperiod and a temperature range of 18° C. (nighttime low) to 30° C. (daytime high). To prepare for evaluation of protein expression in detached leaves, plant leaves were cut at the petiole and stored dry in unsealed plastic bags for one hour before infiltration to simulate a situation where plants would be harvested from a field and transported to a facility for infiltration.

A. tumefaciens cells containing the appropriate plasmids were grown for 24 hours in 2 mL of Luria-Bertani (LB) broth containing appropriate selection antibiotics. Approximately 0.5 mL was then transferred to 25 mL of LB broth supplemented with 10 μL of 100 mM acetosyringone (3', 5'-dimethoxy-4'-hydroxyacetophenone) (Aldrich Chemicals, Milwaukee, Wis.) and 0.5 ml of 1 M 2-(4-morpholino) ethanesulfonic acid (MES) buffer (pH 5.6), and grown overnight at 28° C. with shaking until the cell density (optical density, OD600) reached 1.0 absorbance units. Cells were harvested by centrifugation at 2600 g, resuspended in 10 mL of sterile de-ionized water, and the cell density was adjusted to 1.0 absorbance units. Five milliliters of the A. tumefaciens cell suspension for CMViva was mixed with 5 mL of A. tumefaciens cells containing the p35S:p19 plasmid, and then supplemented with magnesium chloride to reach a final concentration of 10 mM and acetosyringone to 150 □M, and incubated at room temperature for five hours. Bacterial suspensions were then pressure infiltrated onto the abaxial side of either intact or detached N. benthamiana leaves using a 3-mL sterile syringe without a needle at three to four points to sufficiently cover the entire leaf (approximately 1 mL of bacterial suspension per 0.5 g fresh weight of tissue). No A. tumefaciens solution was applied to plants selected as healthy control plants.

Intact plants that had been infiltrated were grown in the greenhouse for the duration of the experiment. Leaves that had been detached were stored in a humidity chamber following infiltration to maintain the health of the plant material. The humidity chamber was prepared by soaking 400 g of Perlite soil additive (E.B. Stone) in 1.5 L of de-ionized water. Excess water was decanted and the saturated Perlite was packed to form a 3-cm thick bed on the bottom of an 11.4 L rectangular Tupperware container. Plant leaves were then placed 7 cm above the Perlite bed on top of racks, and the chamber was then sealed and placed in the dark at 21° C. The humidity chamber was prepared five hours before infiltration to ensure a humid environment upon introduction of the plant leaves.

Twelve hours after infiltration, an induction solution composed of 50 μM 17-β-estradiol (Sigma Inc., St. Louis, Mo.) in 0.05% Tween 20 was applied to all infiltrated N. benthamiana leaves using either cotton tipped applicators to both sides of the leaves or a 3-mL sterile syringe without a needle pressure injected onto the abaxial side of the leaves. To evaluate the effect of multiple inducer applications, the induction solution was applied to half of the total number of infiltrated leaves in the same manner (directly after sampling) at 2-day (48±1 h) increments after the initial induction. No inducer solution was applied at any time to the healthy control plants.

Plant leaves were sampled on the infiltrated/induced areas 2 days (48±1 h) post-induction (60±1 h post-infiltration) by collecting two 7-mm diameter discs at various locations on each leaf and combining the discs to approximate an average leaf sample. Three leaves from different plants were sampled for analysis of intact plant leaves and four leaves were used for analysis of detached plant leaves. Plant leaves were also sampled at 2-day (48±1 h) increments after the initial sampling (and after additional inductions where applicable) to allow evaluation of recombinant protein production kinetics. Extraction buffer composed of 20 mM Tris-HCl (pH 8.1), 150 mM NaCl and 0.01% (v/v) Tween 80 was added immediately after sampling at a ratio of 10 μL./mg fresh weight of tissue, and cells were lysed on ice using a plastic pestle. Lysate was cleared by centrifugation at 20,000 g for 20 min at 4° C. The supernatant was collected and stored at −80° C. until it was assayed.

The methods of protein quantification including Bradford assays for total soluble protein (TSP) analysis, total and functional AAT ELISAs for recombinant AAT analysis were performed as described in the previous examples.

The previous examples demonstrated that recombinant AAT can be transiently produced in non-transgenic N. benthamiana plants at high levels using the CMViva expression system and that addition of the plant virus-encoded gene silencing suppressor Tomato bushy stunt virus (TBSV) P19 gene is effective in enhancing productivity in the infiltrated leaves. In order to investigate if the transient production of recombinant AAT could be further increased, alternate methods were first investigated for application of the chemical inducer. Non-transgenic N. benthamiana plant leaves were therefore co-infiltrated with A. tumefaciens cells containing CMViva and A. tumefaciens cells containing p35S:P19. Twelve hours after infiltration, leaves were induced either by topical application of the induction solution via cotton tipped applicators or by pressure injection via a needleless syringe. In order to evaluate if additional inducer treatments improve productivity, the effect of multiple inducer applications versus the traditional single application was investigated. The kinetics of transient expression were evaluated by sampling plants at two-day intervals for the duration of the experiment.

The total soluble protein (TSP) levels for plants exposed to each of the four induction treatments as well as for the healthy uninfiltrated control plants were measured on a fresh weight (FW) basis and are shown in FIG. 23. The data show that for each of the plants with induction treatments, the TSP levels are significantly higher than the maximum of 8.4±0.20 mg TSP/g FW of tissue for the control plants. In each of the induced plants, the maximum TSP levels are increased by as much as 72% compared to the control plants, resulting in a maximum of 14.4±0.73 mg TSP/g FW of tissue. For the control plants as well as each of the plants with induction treatments, the TSP levels were at a maximum two days after induction, and steadily decreased to 56-60% of the maximum at eight days after induction. Based on the standard deviation of the averages, there was no difference between TSP levels in plants that were induced via topical application and those that were injected.

ELISA analysis was used to quantify the amount of total rAAT transiently produced in each of the induced plants. The effects of inducer application methods on transient production of total rAAT in intact plant leaves were dramatic, as shown in FIG. 24. As expected, the healthy control plant samples did not result in measurable rAAT levels using the highly specific ELSIA analysis. However, each of the induced plants resulted in significant total rAAT production, with the maximum amount found at either six or eight days after induction. With regard to the single topical application, the total rAAT level reached a value of 1.4±0.17% of TSP at four days after induction, and increased to a maximum of 1.9±0.15% of TSP at six days after induction. The total rAAT level was increased to 3.7±0.31% of TSP when using the pressure injection method. When looking at the effect of multiple induction treatments, total rAAT levels are increased 120% and 57% compared to single treatment for the topical application and the pressure injection methods, respectively. A maximum total rAAT level of 5.8±0.46% of TSP was obtained 6 days after induction for multiple induction treatments using the pressure injection method.

When producing rAAT in plant hosts, it has been observed that not all of the rAAT produced is biologically active (see previous examples, Terashima et al. 1999; Huang 2001; Trexler 2002). The amount of functional rAAT in each of the induced intact plants was quantified by ELISA analysis. As shown in FIG. 25, the trends of the effects of inducer treatment methods on transient production of functional rAAT in intact plant leaves mimicked the trends for total rAAT, except that production of functional rAAT reached a maximum at four days after induction. The typical induction treatment of using a single topical application of the chemical inducer resulted in a maximum functional rAAT level 0.80±0.04% of TSP. Using the pressure injection method to apply a single application, a maximum level 1.8±0.09% of TSP was produced. The method of using multiple induction treatments increased functional rAAT levels from 0.80±0.04% to 1.6±0.08% of TSP and from 1.8±0.09% to 2.4±0.09% of TSP for the topical application and the pressure injection methods, respectively. It is also evident that multiple induction treatments help to maintain higher levels of functional AAT over longer time periods as greater than 75% of the maximum levels are still present at six days after induction while less than 40% of the maximum remains when only a single induction treatment is applied. Functional rAAT was undetectable in the control plants using the ELISA method.

The production kinetics of the functional rAAT and total rAAT levels differ in the intact plant leaves, hence the timing of the maximum functional rAAT and maximum total rAAT levels do not occur on the same day. Therefore, functional rAAT production using each of the induction treatments methods was evaluated as a percentage of the total rAAT produced. The percentage of total rAAT that is biologically active is highest early in the production process, as evidenced by FIG. 26. For all induction treatments the percentage of functional rAAT was highest two days after induction. Topical application of the inducer resulted in 61-65% functional product while pressure injection increased levels to 83-90%. While multiple inductions did not increase the maximum percentage of functional rAAT, the percentage of functional rAAT remained higher at six and eight days after infiltration. By the eighth day after induction however, less than 15% of the total rAAT was functional for any of the treatments.

In order to evaluate transient expression of a recombinant human therapeutic protein using a platform that is more amenable to scale-up than intact plant leaves and that would circumvent the need to infiltrate plants in the field or the requirement of a specialized greenhouse facility, rAAT production in detached *N. benthamiana* leaves was investigated. Plant leaves were detached from whole plants and stored dry for about one hour before infiltration. Detached leaves from non-transgenic *N. benthamiana* plants were then co-infiltrated with *A. tumefaciens* cells containing CMViva and cells containing p35S:P19. Twelve hours after infiltration, detached leaves were induced using the same treatment methods as the intact plants to evaluate the effects of topical application versus pressure injection, a single application versus multiple applications, and the production kinetics were again evaluated in the same manner as before. Infiltrated and induced plant leaves were stored in a humidity chamber throughout the course of the experiment. This production scheme was used to simulate a production route where non-transgenic plants would be harvested from a field and transported to a facility for infiltration and subsequent induction.

Total Soluble Protein Production (TSP) levels for detached leaves were measured and are shown in FIG. 23. Again, TSP levels are significantly higher in the induced plants than in the control plants. In all cases, TSP levels were at a maximum early in the production process, and decreased throughout the experiment. The maximum amount of TSP for the control leaves was 3.4±0.18 mg TSP/g FW of tissue. Detached leaves subject to topical application of the inducer resulted in the highest TSP levels, 6.4±0.08 and 6.5±0.28 mg TSP/g FW of tissue for single and multiple applications, respectively. For both single and multiple application treatments, the injected leaves resulted in lower maximum levels of TSP than for the topical application. Comparing TSP levels in detached leaves to intact leaves shows there is generally 50% less TSP on a per FW basis in the detached leaves at all times.

FIG. 24 illustrates the effects of inducer treatment methods on transient production of total rAAT in detached plant leaves. For all induced plants, maximum levels of total rAAT were obtained anywhere between four and six days post induction. Comparing the single application to the multiple application leaves when using the topical method shows an increase from a maximum value of at 2.5±0.08% to 3.5±0.15% of TSP. Single application treatment using pressure injection results in 2.4±0.18% of TSP, which is equal to within one standard deviation of the total rAAT level obtained from the single topical application. However, leaves exposed to multiple pressure injections do not show increased levels of functional rAAT. It is important to point out here that in detached leaves induced using the syringe method, rings of necrotic regions caused by applying high pressure on the luer tip of the syringe to the surface of the leaf were observed around the site of injection. The areas within and around these injection sites started to thin and turn brown in color by the third to fourth day after induction. This observation was even more evident when multiple inductions were used, as there were more regions of necrosis caused by the additional injections. On a percent TSP basis, total rAAT production in detached leaves compares well to that in intact leaves for the topical application method, even surpassing the maximum level by 0.6% of TSP when a single application was used.

FIG. 25 shows the levels of biologically functional rAAT transiently produced in detached leaves. Here, the production kinetics shows a maximum amount of functional rAAT at four days post induction. The trends for topical applications are similar to those described for total rAAT as multiple applications results in much greater rAAT levels than those obtained from a single application, 1.3±0.05% and 0.71±0.04% of TSP at four days post induction, respectively. Single application treatment using pressure injection results in 1.3±0.06% of TSP, 80% higher than using a single topical application. Once again the syringe injection method reduced the total rAAT levels when multiple applications were applied, presumably due to tissue damage. For the topical application method, functional rAAT production in detached leaves was only slightly less than for intact leaves (0.09 and 0.3% of TSP less than in intact leaves at four days post induction for single and multiple applications, respectively).

The percentage of biologically functional rAAT to total rAAT for detached leaves is displayed in FIG. 26. For each of the induction treatment methods, the percentage of functional rAAT was highest at two days after induction. For the topical application method, the maximum percentage of functional rAAT was 55-65%, while for the injection method 85-87% was found to be biologically active. The number of inducer applications did not appear to enhance stability of functional rAAT. The maximum percentage of rAAT for each of the induction application methods in detached leaves was within 10% of the values obtained for intact leaves.

While many methods are used for chemical induction solution to plants leaves, most fall into one of the two distinct categories of either using a surface application or using a pressure gradient driving force to apply the solution. To evaluate the differences in protein production between these two categories we elected to evaluate production strategies that would be representative of the maximum amount of inducer solution that could be applied to the plant leaves using any of the current induction methods, many of which can be used for scale-up. For example, topical application via a cotton swab represents the maximum amount of inducer that could be applied to the surface of a plant leaf using any of the surface application methods (such as dipping). Pressure injection using a syringe without a needle represents the maximum amount of induction solution that could be driven into the tissue using a pressure driving force induction strategy (such as vacuum infiltration). Our results show that in intact plants using a single pressure injection, we were able to dramatically increase heterologous protein production as we obtained 95% and 125% more total and functional rAAT, respectively, compared to production using a single topical application. These results suggests that the topical application of the induction solution either does not reach all of the infected cells or the amount of induction solution reaching the cells in the center of the leaf tissue is not adequate for optimal activation, as induction has been shown to be concentration dependant (Zuo et al. 2000; Sun et al. 2003). This concern is critical whether using stably transformed plants or transient expression and should be addressed when attempting to achieve optimal induction using a chemical inducible promoter system in plant tissues.

Previous examples show that the number of inducer applications can greatly impact protein expression. Previous research has shown that transcript levels and subsequent recombinant protein production reach a maximum and then decrease over time when using inducible expression systems and suggests that modifications to the current induction treatment process may be necessary for optimal protein production (Zuo et al. 2000; Moore et al. 2006; Dohi et al. 2006). To address this issue, we first investigated if we could keep transcript levels high and increase protein production by applying additional inducer. We elected to add induction solution every two days as previous research has shown when using the XVE expression system as used in this study, transcript levels reach a maximum and then decrease two to four days after induction (Zuo et al. 2000; Dohi et al.). When comparing production using multiple applications to the more conventional method of a single application of induction solution, our results show that maximum functional rAAT expression levels were increased by at least 35% in both treatment methods in intact plants and for topical induction in detached plant leaves, as shown in FIG. 23. We were able to maintain the amount of functional rAAT for a longer time period using multiple inductions as 75% of the maximum level is still produced six days after induction. Our results suggest that in situations where only a single application is used, the inducer may become limiting due to uptake and binding of estradiol to the XVE protein or degradation of estradiol, as has been observed with other chemical inducers (Moore et al. 2006). As previously mentioned, the results using syringe injection in detached leaves deviate from the expected trend since pressure injection compromised plant leaf health. In addition, this effect was amplified when applying multiple injections.

As the production levels in plant-based systems continue to increase, the economics may favor a switch from traditional production methods to plant-based systems as is increasingly evident by the number of companies advancing such proteins through clinical trials (Nykiforuk et al. 2006; Fox 2006). Therefore, scale-up of the process will become an important issue. Using a strategy that mimics harvesting non-transgenic plant biomass from a field or greenhouse and bringing it to a facility for production, our data show that production in detached leaves results in approximately half of the overall TSP obtained with intact leaves. This lower amount is expected since detached leaves no longer have a source of nutrients to sustain production. However, as portrayed in FIG. 25, production in detached leaves results in only slightly less functional rAAT than the intact plant leaves, on a TSP basis. When using multiple surface induction treatments, the resulting production in detached leaves is 1.3±0.05%, very nearly approaching the value of 1.6±0.08% of TSP obtained form intact plants. Although the functional rAAT levels for detached leaves are similar to intact leaves on % TSP basis, because the TSP levels in detached leaves are significantly lower, the functional rAAT levels are lower per gram FW tissue than for the intact leaves. For detached leaves, pressure driven application methods may need to be altered to approach production levels achievable in intact plants.

Chemically inducible promoters, especially utilizing viral amplicon expression systems, are showing great promise for rapid high-level production of heterologous proteins in plant hosts. In this study, we have demonstrated that the method of the inducer application can be used to dramatically increase the amount of heterologous protein produced in chemically inducible agroinfiltrated systems. Combining both the strategies of multiple applications and pressure infiltration in intact leaves, production of heterologous protein was increased by nearly 3-fold to levels to nearly 2.5% of the TSP for biologically functional protein and nearly 6% of the TSP for overall heterologous protein. This is a significant improvement over the traditional single topical application. The highest reported level of recombinant protein production using a chemically inducible viral amplicon expression system has been the production of the reporter protein, GFP, which has been expressed at up to 10% of the TSP (estimated by band intensity) four days after induction in a stably transformed tobacco suspension culture using the XVE promoter driving a tomato mosaic virus (ToMV) viral ampicon expression system (Dohi et al. 2006). Our production of a heterologous human protein at almost 6% of TSP compares well to production of this report protein, especially considering that AAT is degraded in plants (Terashima et al. 1999) while GFP is known to be very stable. Production of heterologous protein using our expression system compares favorably to production using the bean yellow dwarf virus (BeYDV) alcohol inducible expression system, in which production of Norwalk virus capsid protein (NVCP) has been demonstrated up to 1.2% of TSP in a stably transformed tobacco suspension culture (Zhang et al. 2006). To date, production using the CMViva system is the only report of transient heterologous protein production using a chemically inducible viral amplicon expression system.

Studies have shown that the production of rAAT in plant hosts results in both active and inactive form of rAAT being produced (Terashima et al. 1999; Huang et al. 2001; Trexler et al. 2002). The same observation was observed in this example, as is evident in the larger amounts of total rAAT than functional rAAT. For intact plants, the maximum level of production is 5.8±0.46% of TSP for total rAAT and 2.4±0.09% of TSP for functional rAAT. When looking at the relative percentage of functional to total rAAT, it is evident that functional protein is being diminished since functional rAAT is greater than 50% for topical and 85% for pressure induction application after only two days of production, but then quickly decreases throughout the production process. The same is true for production in detached plant leaves. This suggests that either protein denaturation/unfolding or protein degradation/cleavage is occurring, as has been observed in the past for plant-produced rAAT (Terashima et al. 1999; Huang et al. 2001; Trexler et al. 2002). However, this also suggests that optimizing the amount of rAAT produced during the early stages of production may lead to a higher overall yield of functional rAAT. Alternately, if degradation can be reduced such that the maximum percent of functional rAAT can coincide with the maximum level of total rAAT production, then it would be possible to achieve 5.8±0.46% of TSP as biologically functional rAAT using multiple syringe induction treatments in intact *N. benthamiana* leaves or 3.5±0.15% of TSP when using detached plant tissue. It was also observed that the total rAAT levels do not drop off as rapidly as functional rAAT levels, so if degradation can be reduced not only could very high yields be achieved but the maximum level of rAAT production would be less sensitive to the time at which the protein is recovered.

High-level transient production of heterologous proteins can be achieved in both intact and detached plant leaves by utilizing a chemically inducible viral amplicon expression system. Altering the method in which the induction solution is applied in order to increase contact to the plant cells can further elevate production. By applying induction solution via topical application to mimic total surface coverage and applying the inducer every two days to infiltrate detached plant leaves, maximum levels of biologically functional rAAT were increased 1.8-fold. When evaluating production in detached leaves, it is particularly important to ensure the method of induction does not compromise the health of the leaf and, therefore, multiple pressure driven injections are not recommended for detached leaves although it is noted that an alternate driving force method that does not damage the plant tissue may result in higher production. Production can be elevated to an even larger degree using alternate induction strategies in intact leaves. By applying multiple applications of induction solution via pressure injection to infiltrated intact leaves which provides the most uniform and constant inducer concentration within the tissue, maximum levels of biologically functional rAAT were elevated up to 3-fold compared to the conventional method of a single topical application, and expression levels remained high even six days post induction. Therefore, for production in intact plant leaves, multiple application of induction solution using a driving force method is recommended to increase inducer contact and availability. This example lays the basis for developing induction strategies to scale-up processes which use chemically inducible viral amplicon systems in order to achieve high-level transient production of heterologous proteins in *N. benthamiana* plant leaves.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the claims.

REFERENCES

The following references cited herein are hereby incorporated by reference in their entirety.

1. Angell S. M. and Baulcombe D. C. (1997) Consistent gene silencing in transgenic plants expressing a replicating potato virus X RNA. EMBO J. 16, 3675-3684.
2. Aoyama T. and Chua N. H. (1997) A glucocorticoid-mediated transcriptional induction system in transgenic plants. Plant J. 11, 605-612.
3. Becerra-Arteaga A, Mason H S, Shuler M L. 2006. Production, secretion, and stability of human secreted alkaline phosphatase in tobacco NT1 cell suspension cultures. Biotechnology Progress 22(6):1643-1649.
4. Ding S. W., Rathjen J. P., Li W. X., Swanson R., Healy H. and Symons R. H. (1995). Efficient infection from cDNA clones of cucumber mosaic cucumovirus RNAs in a new plasmid vector. J. Gen. Virol. 76, 459-464.
5. Dohi K, Nishikiori M, Tamai A, Ishikawa M, Meshi T, Mori M. 2006. Inducible virus-mediated expression of a foreign protein in suspension-cultured plant cells. Archives of Virology 151(6):1075-1084.
6. Drohan, W.; Huang, N.; Rodriguez, R. L. Expression and purification of functional human alpha-1-antitrypsin from cultured plant cells. Biotechnol. Prog. 2001, 17, (1), 126-133.
7. Escobar M. A., Civerolo E. L., Summerfelt K. R. and Dandekar A. M. (2001) RNAi-mediated oncogene silencing confers resistance to crown gall tumorigenesis. Proc. Natl. Acad. Sci. U.S.A 98, 13437-13442.
8. Fischer R., Vaquero-Martin C., Sack M., Drossard J., Emans N. and Commandeur U. (1999) Towards molecular farming in the future: Transient protein expression in plants. Biotechnol. Appl. Biochem. 30, 113-116.
9. Fox, J. L. Turning plants into protein factories. Nat. Biotechnol. 2006, 24, (10), 1191-1193.
10. Gettins P G W. 2002. Serpin structure, mechanism, and function. Chem Rev 102(12):4751-4803.

11. Gils M., Kandzia R., Marillonnet S., Klimyuk V. and Gleba Y. (2005) High-yield production of authentic human growth hormone using a plant virus-based expression system. Plant Biotechnol. J.13, 613-620.
12. Gleave A. P. (1992) A versatile binary vector system with a T-DNA organizational-structure conducive to efficient integration of cloned DNA into the plant genome. Plant Mol. Biol. 20, 1203-1207.
13. Gleba Y., Klimyuk V. and Marillonnet S. (2005) Magnifection—a new platform for expressing recombinant vaccines in plants. Vaccine 23, 2042-2048.
14. Goldstein D. A. and Thomas J. A. (2004) Biopharmaceuticals derived from genetically modified plants. QJM 97, 705-716.
15. Griffiths S W, King J, Cooney C L. 2002. The reactivity and oxidation pathway of cysteine 232 in recombinant human alpha 1-antitrypsin. J Biol Chem 277(28):25486-25492.
16. Hamilton C. M. (1997) A binary-BAC system for plant transformation with high-molecular-weight DNA. Gene 200, 107-116.
17. Huang J. M., Sutliff T. D., Wu L. Y., Nandi S., Benge K., Terashima M., Ralston A. H., Drohan W., Huang N. and Rodriguez R. L. (2001) Expression and purification of functional human a-1-antitrypsin from cultured plant cells. Biotechnol. Prog. 17, 126-133.
18. Huang, J. M.; Sutliff, T. D.; Wu, L. Y.; Nandi, S.; Benge, K.; Terashima, M.; Ralston, A. H.; Huntington J A, Read R J, Carrell R W. 2000. Structure of a serpin-protease complex shows inhibition by deformation. Nature 407 (6806):923-926.
19. Joo S. Y., Lee K. H., Lee Y. I., Kim D. I. (2006). Enhanced production of hGM-CSF by medium exchange in transgenic Oryza sativa L. suspension cultures. Enzyme and Microbial Technology 39(3):486-489.
20. Kolarich D, Weber A, Turecek P L, Schwarz H P, Altmann F. 2006. Comprehensive glyco-proteomic analysis of human alpha(1)-antitrypsin and its charge isoforms. Proteomics 6(11):3369-3380.
21. Ma J. K. C., Drake P. M. W. and Christou P. (2003) The production of recombinant pharmaceutical proteins in plants. Nat. Rev. Genet. 4, 794-805.
22. Manske U. and Schiemann J. (2005) Development and assessment of a Potato vrius X-based expression system with improved biosafety. Environ. Biosafety Res. 4, 45-57.
23. McBride K. E. and Summerfelt K. R. (1990) Improved binary vectors for Agrobacterium-mediated plant transformation. Plant Mol. Biol. 14, 269-276.
24. Moore, I.; Samalova, M.; Kurup, S. Transactivated and chemically inducible gene expression in plants. Plant J. 2006, 45, (4), 651-683.
25. Mori M., Fujihara N., Mise K. and Furusawa I. (2001) Inducible high-level mRNA amplification system by viral replicase in transgenic plants. Plant J. 27, 79-86.
26. Mori M., Kaido M., Okuno T. and Furusawa I. (1993) Messenger-RNA amplification system by viral replicase in transgenic plants. FEBS Lett. 336, 171-174.
27. Nykiforuk, C. L.; Boothe, J. G.; Murray, E. W.; Keon, R. G.; Goren, H. J.; Markley, N. A.; Moloney, M. M. Transgenic expression and recovery of biologically active recombinant human insulin from Arabidopsis thaliana seeds. Plant Biotechnol. J. 2006, 4, (1), 77-85.
28. Rabindran S. and Dawson W. O. (2001) Assessment of recombinants that arise from the use of a TMV-based transient expression vector. Virology 284, 182-189.
29. Schiermeyer A, Schinkel H, Apel S, Fischer R, Schillberg S. 2005. Production of Desmodus rotundas salivary plasminogen activator alpha 1 (DSPA alpha 1) in tobacco is hampered by proteolysis. Biotechnology and Bioengineering 89(7):848-858.
30. Shivprasad S., Pogue G. P., Lewandowski D. J., Hidalgo J., Donson J., Grill L. K. and Dawson W. O. (1999) Heterologous sequences greatly affect foreign gene expression in Tobacco Mosaic Virus-based vectors. Virology 255, 312-323.
31. Sun, J. Q.; Niu, Q. W.; Tarkowski, P.; Zheng, B. L.; Tarkowska, D.; Sandberg, G.; Chua, N. H.; Zuo, J. R. The Arabidopsis AtIPT8/PGA22 gene encodes an isopentenyl transferase that is involved in de novo cytokinin biosynthesis. Plant Physiol. 2003, 131, (1), 167-176.
32. Tavva S. V., Dinkins, D. R, Palli, R. S., Collins, B. G. Development of a methoxyfenozide-responsive gene switch for applications in plants. The Plant Journal, 45(3): 457-469.
33. Terashima M, Murai Y, Kawamura M, Nakanishi S, Stoltz T, Chen L, Drohan W, Rodriguez R L, Katoh S. 1999. Production of functional human alpha(1)-antitrypsin by plant cell culture. Applied Microbiology and Biotechnology 52(4):516-523.
34. Trexler M. M., McDonald K. A. and Jackman A. P. (2002) Bioreactor production of human al-antitrypsin using metabolically regulated plant cell cultures. Biotechnol. Prog. 18, 501-508.
35. Trexler M. M., McDonald K. A. and Jackman A. P. (2005) A cyclical semicontinuous process for production of human al-antitrypsin using metabolically induced plant cell suspension cultures. Biotechnol. Prog. 21, 321-328.
36. Turpen T. H., Turpen A. M., Weinzettl N., Kumagai M. H. and Dawson W. O. (1993) Transfection of whole plants from wounds inoculated with Agrobacterium-tumefaciens containing cDNA of Tobacco Mosaic-Virus. J. Virol. Meth. 42, 227-240.
37. Voinnet O., Rivas S., Mestre P. and Baulcombe D. (2003) An enhanced transient expression system in plants based on suppression of gene silencing by the p19 protein of tomato bushy stunt virus. Plant J. 33, 949-956.
38. Wilczynska M., Fa M., Karolin 3., Ohlsson P. I., Johansson L. B. A. and Ny T. (1997) Structural insights into serpin-protease complexes reveal the inhibitory mechanism of serpins. Nat. Struct. Biol. 4, 354-357.
39. Wilson C, Bellen H J, Gehring W J. 1990. POSITION EFFECTS ON EUKARYOTIC GENE EXPRESSION. Palade, G. E. p 679-714.

TABLE 1

| Primer | Sequence | Description |
|---|---|---|
| O14G10Pf SEQ ID NO: 1 | 5'-ACATGCAATGCATCTGATAGTTTAAACTGAAGGC-3' | Forward primer for G-10-90 promoter |

TABLE 1-continued

| Primer | Sequence | Description |
|---|---|---|
| O15NPeaTr SEQ ID NO: 2 | 5'-ACAGGATGCGGCCGCCAGTTTCCAAGCTTGTTTGG-3' | Reverse primer for G-10-90 promoter |
| O16NOpf SEQ ID NO: 3 | 5'-CATACCAATGCATTTACTTGCACAGCTTGG-3' | Forward primer for OlexA operator |
| O17XSOpr SEQ ID NO: 4 | 5'-CATATCTCGAGGCTAGAGTCGAC-3' | Reverse primer for OlexA Operator |
| OQCD3-1 SEQ ID NO: 5 | 5'-ACTTCTCGAGTGGCGCGCCGGTCAACATGGTGGAGC-3' | Forward primer for 35S promoter |
| OQCD3-2 SEQ ID NO: 6 | 5'-ACACGAATTCAGGCACACTGAGACGCA-3' | Reverse primer for CMV RNA3 |
| OQCD3-3 SEQ ID NO: 7 | 5'-AATGAAGCTTAATTCCTATCTCACGGATG-3' | Forward primer for CMV RNA3 |
| OQCD3-4 SEQ ID NO: 8 | 5'-ATCTGGATCCTGGTCTCCTTATGG-3' | Reverse primer for CMV RNA-3 |
| OQCD3-5 SEQ ID NO: 9 | 5'-ATACGGATCCATTCGGTACGCTGAAATC-3' | Forward primer for 35S-T in pQCD3 |
| OQCD3-6 SEQ ID NO: 10 | 5'-ATGTAGATCTGGCGCGCCGGATTTTAGTACTGGAT-3' | Reverse primer for 35S-T in pQCD3 |
| OSDAATPst SEQ ID NO: 11 | 5'-TCAACTGCAGAACAATGAAGAACACCTCCTCCCT-3' | Forward primer for SD-AAT |
| OSDAATCPst SEQ ID NO: 12 | 5'-ACATCTGCAGTCACTTCTGCGTGGGGT-3' | Reverse primer for SD-AAT |

Table 2 Comparison of *N. benthamiana* growth and rAAT production in bioreactors using different expression systems

| System | $X_0$ (g-DCW/L) | $X_{max}$ (g-DCW/L) | $\mu_{max}$ (day$^{-1}$) | Maximum Extracellular Protease Activity (U/L) | $OUR_{max}$ (mmol O2/ L-h) | Maximum Extracellular Total rAAT (μg/L) | Maximum Extracellular Functional rAAT (μg/L) | Maximum Extracellular Functional/ Total rAAT (%) |
|---|---|---|---|---|---|---|---|---|
| Wild type | 1.4 | 13.4 (d9)* | 0.26 | 981 (d10) | 1.62 (d8) | — | — | — |
| 35S | 0.9 | 12.2 (d22) | 0.14 | 1610 (d22) | 0.90 (d16) | 3500 (d22) | 5.9 (d22) | 0.17 (d22) |
| XVE | 1.2 | 12.3 (d10) | 0.24 | 2550 (d20) | 1.2 (d11) | 690 (d22) | 4.1 (d19) | 0.93 (d19) |
| CMViva | 1.5 | 12.7 (d10) | 0.26 | 3420 (d18) | 1.4 (d10) | 140 (d16) | 27.3 (d18) | 21.9 (d18) |

(day)*: day after inoculation. For XVE and CMViva system, rAAT was induced by adding inducer at day 11 after inoculation.

Table 3 Comparison of rAAT production in *N. benthamiana* with the CMViva system following induction

| System | Functional rAAT/TSP[a] (%) | Total rAAT/TSP (%) | Functional rAAT/Total rAAT (%) | Functional rAAT/DCW[b] (%) | Total rAAT/DCW (%) |
|---|---|---|---|---|---|
| Transgenic plant cell cultures in bioreactor, without p19 * | 0.019 | 0.086 | 22 | $2.4 \times 10^{-4}$ | $1.24 \times 10^{-3}$ |
| Transient expression in whole intact plant leaves, without p19 ** | 0.16 | 0.57 | 28 | $2.5 \times 10^{-2}$ | $9.1 \times 10^{-2}$ |
| Transient expression in whole intact plant leaves, with p19 ** | 1.2 | 1.7 | 71 | $1.6 \times 10^{-1}$ | $2.38 \times 10^{-1}$ |

[a]TSP = Total Soluble Protein
[b]DCW = Dry cell weight
* this example
** previous examples

TABLE 4

| System | Functional rAAT/TSP[a] (%) | Total rAAT/TSP (%) | Functional rAAT/Total rAAT (%) |
|---|---|---|---|
| CMViva, transient expression in whole plant leaves, w/induction, w/o p19 | 0.16 | 0.57 | 28.1 |
| CMViva, transient expression in whole plant leaves, w/induction, w/p19 | 1.2 | 1.7 | 70.5 |
| CMViva, transgenic plant cell cultures in bioreactor, w/induction, w/o p19, (extracellular rAAT yield) | 0.019 | 0.086 | 22.1 |
| CMViva, transgenic plant cell cultures in bioreactor, pH control, w/induction, w/o p19, (extracellular rAAT yield) | 0.066 | 0.137 | 48.2 |

We claim:

1. A method for producing a heterologous protein, said method comprising:
   a) providing a plant cell comprising a cucumber mosaic virus (CMV) estradiol-inducible viral amplicon expression system capable of facilitating estradiol-inducible expression of a heterologous protein;
   b) culturing the plant cell in a cell culture medium;
   c) contacting the cell culture medium with estradiol, wherein the estradiol is present in the cell culture medium at a final concentration in the range of 0.1 µM to 1 µM;
   d) incubating the plant cell in the cell culture medium for a time period sufficient to produce the heterologous protein; and
   e) harvesting the heterologous protein from the cell culture medium.

2. The method of claim 1, wherein the plant cell constitutively expresses a gene silencing suppressor.

3. The method of claim 2, wherein the gene silencing suppressor is p19.

4. The method of claim 1, wherein the heterologous protein is a blood protein.

5. The method of claim 1, wherein the heterologous protein is an enzyme capable of modifying, degrading, or decomposing plant cell walls.

6. The method of claim 2, wherein the p19 is from Tomato bushy stunt virus.

7. The method of claim 1, wherein the pH of the cell culture medium is in the range of 6.4 to 6.8.

* * * * *

SEQUENCE LISTING

```
<160> NUMBER OF SEQ ID NOS: 12

<210> SEQ ID NO 1
<211> LENGTH: 34
<212> TYPE: DNA
<213> ORGANISM: Artificial Sequence
<220> FEATURE:
<223> OTHER INFORMATION: Primer

<400> SEQUENCE: 1
acatgcaatg catctgatag tttaaactga aggc                              34

<210> SEQ ID NO 2
<211> LENGTH: 35
<212> TYPE: DNA
<213> ORGANISM: Artificial Sequence
<220> FEATURE:
<223> OTHER INFORMATION: Primer

<400> SEQUENCE: 2
acaggatgcg gccgccagtt tccaagcttg tttgg                             35

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
cataccaatg catttacttg cacagcttgg                                   30

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
catatctcga ggctagagtc gac                                          23

<210> SEQ ID NO 5
<211> LENGTH: 36
<212> TYPE: DNA
<213> ORGANISM: Artificial Sequence
<220> FEATURE:
<223> OTHER INFORMATION: Primer

<400> SEQUENCE: 5
acttctcgag tggcgcgccg gtcaacatgg tggagc                            36
```

```
<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
acacgaattc aggcacactg agacgca                                       27

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
aatgaagctt aattcctatc tcacggatg                                     29

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
atctggatcc tggtctcctt atgg                                          24

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
atacggatcc attcggtacg ctgaaatc                                      28

<210> SEQ ID NO 10
<211> LENGTH: 35
<212> TYPE: DNA
<213> ORGANISM: Artificial Sequence
<220> FEATURE:
<223> OTHER INFORMATION: Primer

<400> SEQUENCE: 10
atgtagatct ggcgcgccgg attttagtac tggat                              35

<210> SEQ ID NO 11
<211> LENGTH: 34
<212> TYPE: DNA
<213> ORGANISM: Artificial Sequence
<220> FEATURE:
<223> OTHER INFORMATION: Primer

<400> SEQUENCE: 11
tcaactgcag aacaatgaag aacacctcct ccct                               34

<210> SEQ ID NO 12
<211> LENGTH: 27
<212> TYPE: DNA
<213> ORGANISM: Artificial Sequence
<220> FEATURE:
```

```
<223> OTHER INFORMATION: Primer

<400> SEQUENCE: 12
acatctgcag tcacttctgc gtggggt                                              27
```